US009169315B2

(12) United States Patent
Kalle et al.

(10) Patent No.: US 9,169,315 B2
(45) Date of Patent: Oct. 27, 2015

(54) HEPARIN COFACTOR II FRAGMENTS WITH ANTI-INFLAMMATORY AND ANTI-COAGULANT ACTIVITY

(75) Inventors: Martina Kalle, Lund (SE); Gopinath Kasetty, Lund (SE); Nils Martin Malmsten, Täby (SE); Praveen Papareddy, Lund (SE); Artur Schmidtchen, Lund (SE); Björn Ulrik Walse, Lund (SE)

(73) Assignee: XIMMUNE AB, Lund (SE)

( * ) Notice: Subject to any disclaimer, the term of this patent is extended or adjusted under 35 U.S.C. 154(b) by 0 days.

(21) Appl. No.: 13/497,006

(22) PCT Filed: Sep. 21, 2010

(86) PCT No.: PCT/GB2010/001780
§ 371 (c)(1),
(2), (4) Date: Mar. 19, 2012

(87) PCT Pub. No.: WO2011/036444
PCT Pub. Date: Mar. 31, 2011

(65) Prior Publication Data
US 2012/0177715 A1 Jul. 12, 2012

(30) Foreign Application Priority Data
Sep. 22, 2009 (GB) .................... 0916578.8

(51) Int. Cl.
*A61K 38/17* (2006.01)
*C07K 14/435* (2006.01)
*A61P 29/00* (2006.01)
*A61K 9/00* (2006.01)
*A61K 9/70* (2006.01)
*A61P 7/02* (2006.01)
*A61K 38/10* (2006.01)
*C07K 7/08* (2006.01)
*C07K 14/81* (2006.01)
*A61K 45/06* (2006.01)
*A61K 31/55* (2006.01)
*A61K 38/00* (2006.01)

(52) U.S. Cl.
CPC ............ *C07K 14/8121* (2013.01); *A61K 31/55* (2013.01); *A61K 45/06* (2013.01); *A61K 38/00* (2013.01)

(58) Field of Classification Search
None
See application file for complete search history.

(56) References Cited

U.S. PATENT DOCUMENTS

| 4,235,871 A | 11/1980 | Papahadjopoulos et al. |
| 5,118,793 A * | 6/1992 | Tollefsen et al. ............ 530/350 |
| 5,643,872 A | 7/1997 | Ali et al. |
| 5,851,451 A | 12/1998 | Takechi et al. |
| 6,008,058 A | 12/1999 | Spatola et al. |
| 6,174,721 B1 | 1/2001 | Innis et al. |
| 2005/0261241 A1 * | 11/2005 | Cardin ............................ 514/54 |

FOREIGN PATENT DOCUMENTS

| EP | 0 213 303 A2 | 3/1987 |
| EP | 0 424 351 A2 | 4/1991 |
| EP | 0781558 A2 * | 12/1996 |
| EP | 0 781 558 A2 | 7/1997 |
| WO | WO-92/18139 A1 | 10/1992 |
| WO | WO-96/04378 A2 | 2/1996 |
| WO | WO-03/059973 A2 | 7/2003 |
| WO | WO-2005/007197 A2 | 1/2005 |
| WO | WO-2005/015206 A2 | 2/2005 |

OTHER PUBLICATIONS

Hortin et al. J Biol Chem. 264(24);13979-13982:1989.*
Sheffield et al. FEBS Letters. 365;189-192:1995.*
Parker et al. J Biol Chem. 260(6);3501-3505:1985.*
Physicians Desk Reference. Protamine Sulfate. Ver. 1:2012.*
Whinna et al. Letters in Peptide Science. 1;3-8:1994.*
UniProt. Serpin peptidase inhibitor clade D member 1. H9LB84_CERSI.*
Andersson, E., et al. (Mar. 2004). "Antimicrobial Activities of Heparin-Binding Peptides," *Eur. J. Biochem.* 271 (6):1219-1226.
Blondelle, S.E. et al. (2000)."Combinatorial Libraries: A Tool to Design Antimicrobial and Antifungal Peptide Analogues Having Lytic Specificities for Structure-Activity Relationship Studies," *Biopolymers* 55(1):74-87.
Bode, W. (Apr. 2006). "The Structure of Thrombin: A Janus-Headed Proteinase," *Semin. Thromb. Hemost.* 32(Suppl 1):16-31.
Bowen, S. et al. (Mar. 1999). "Relationship Between Molecular Mass and Duration of Activity of Polyethylene Glycol Conjugated Granulocyte Colony-Stimulating Factor Mutein," *Exp. Hematol.* 27(3): 425-432.
Bradford, M.M. (May 7, 1976). "A Rapid and Sensitive Method for the Quantitation of Microgram Quantities of Protein Utilizing the Principle of Protein-Dye Binding," *Anal. Biochem.* 72:248-254.

(Continued)

*Primary Examiner* — Amber D Steele
*Assistant Examiner* — Schuyler Milton
(74) *Attorney, Agent, or Firm* — Morrison & Foerster LLP

(57) ABSTRACT

The present invention provides polypeptides comprising or consisting of an amino acid sequence derived from a naturally occurring protein which modulates blood coagulation, or a fragment, variant, fusion or derivative thereof, or a fusion of said fragment, variant or derivative thereof, for use in the treatment or prevention of inflammation and/or excessive coagulation of the blood. Related aspects of the invention provide isolated polypeptides comprising or consisting of an amino acid sequence of SEQ ID NOS: 1 to 3, or a fragment, variant, fusion or derivative thereof, or a fusion of said fragment, variant or derivative thereof, which exhibit an anti-inflammatory activity, together with isolated nucleic acid molecules, vectors and host cells for making the same. Additionally provided are pharmaceutical compositions comprising a polypeptide of the invention, as well as methods of use of the same in the treatment and/or prevention of inflammation and/or excessive coagulation.

11 Claims, 41 Drawing Sheets

(56) References Cited

OTHER PUBLICATIONS

Figure 1:
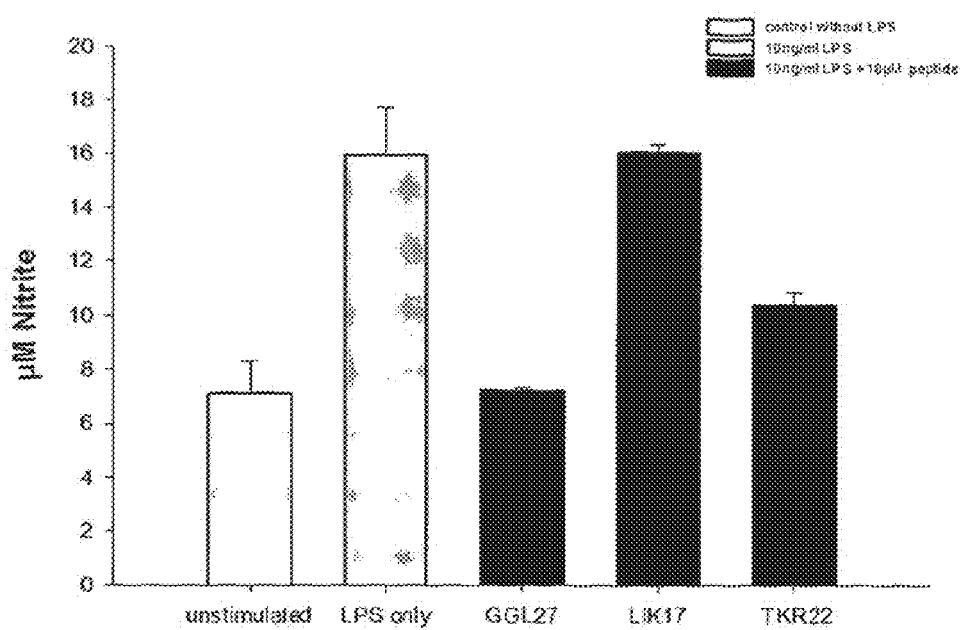

Brogden, K.A. (Mar. 2005). "Antimicrobial Peptides: Pore Formers or Metabolic Inhibitors in Bacteria?," *Nat. Rev. Microbiol.* 3(3):238-250.

Chapman, A.P. et al. (Aug. 1999). "Therapeutic Antibody Fragments with Prolonged in Vivo Half-Lives," *Nat. Biotechnol.* 17(8):780-783.

Chapman, A.P. (Jun. 17, 2002). "PEGylated Antibodies and Antibody Fragments for Improved Therapy: A Review," *Adv. Drug Deliv. Rev.* 54(4):531-545.

Cheng, F. et al. (Dec. 1992). "A New Method for Sequence Analysis of Glycosaminoglycans From Heavily Substituted Proteoglycans Reveals Non-Random Positioning of 4- and 6-O-Sulphated N-Acetylgalactosamine in Aggrecan-Derived Chondroitin Sulphate," *Glycobiology* 2(6):553-561.

Cole, A.M. et al. (Jul. 15, 2001). "Cutting Edge: IFN-Inducible ELR-CXC Chemokines Display Defensin-Like Antimicrobial Activity," *J. Immunol.* 167(2):623-627.

Crawley, J.T.B. et al. (Feb. 2008, e-pub. Oct. 19, 2007). "The Haemostatic Role of Tissue Factor Pathway Inhibitor," *Arterioscler Thromb. Vasc. Biol.* 28(2):233-242.

Cunningham, A.C. et al. (Oct. 15, 2002). "Structural and Functional Characterization of Tissue Factor Pathway Inhibitor Following Degradation by Matrix Metalloproteinase-8," *Biochem. J.* 367(Pt 2):451-458.

Davie, E.W. et al. (Apr. 2006). "An Overview of the Structure and Function of Thrombin," *Semin. Thromb. Hemost.* 32(Suppl 1):3-15.

Dinges, M.M. et al. (Nov. 2001). "Comparative Analysis of Lipopolysaccharide-Induced Tumor Necrosis Factor Alpha Activity in Serum and Lethality in Mice and Rabbits Pretreated With the *Staphylococcal* Superantigen Toxic Shock Syndrome Toxin 1," *Infect. Immun.* 69(11):7169-7172.

Elsbach, P. (Jun. 2003). "What is the real role of antimicrobial polypeptides that can mediate several other inflammatory responses?," *J. Clin. Invest.* 111(11):1643-1645.

Ettelaie, C. et al. (Dec. 17, 1999). "The role of the C-terminal domain in the inhibitory functions of tissue factor pathway inhibitor," *FEBS Letters* 463(3):341-344.

Fernandez-Lopez, S. et al. (Jul. 26, 2001). "Antibacterial Agents Based on the Cyclic D,L-α-Peptide Architecture," *Nature* 412(6845):452-455.

Frick, I.M. et al. (Nov. 29, 2006, e-pub. Nov. 9, 2006). "The Contact System—A Novel Branch of Innate Immunity Generating Antibacterial Peptides," *The EMBO J.* 25(23):5569-5578.

Ganz, T. (Sep. 2003). "Defensins: Antimicrobial Peptides of Innate Immunity," *Nat. Rev. Immunol.* 3(9):710-720.

GenBank Accession No. AAW06887, last updated Mar. 18, 1997, located at http://www.ebi.ac.uk/Tools/es/cgi-bin/epo/epofetch.cgi?AAW06887, last visited on Jan. 26, 2011, one page.

Girard, T.J. et al. (Apr. 6, 1989). "Functional Significance of the Kunitz-Type Inhibitory Domains of Lipoprotein-Associated Coagulation Inhibitor," *Nature* 338(6215):518-520.

Greenfield, N. et al. (Oct. 1969). "Computed Circular Dichroism Spectra for the Evaluation of Protein Conformation," *Biochemistry* 8(10):4108-4116.

Hancock, R.E.W. et al. (Dec. 2006). "Antimicrobial and Host-Defense Peptides as New Anti-Infective Therapeutic Strategies," *Nat. Biotechnol.* 24(12):1551-1557.

Harder, J. et al. (2007). "Human Antimicrobial Proteins—Effectors of Innate Immunity," *J. Endotoxin Res.* 13(6):317-338.

Haupt, H. et al. (Jul. 1972). "Human Serum Proteins With High Affinity for Carboxymethylcellulose. I. Isolation of Lysozyme, C1q and 2 Hitherto Unknown Globulins," *Hoppe Seylers Z Physiol Chem.* 353(7):1125-1132. (With English Summary Translation).

Hembrough, T.A. et al. (May 1, 2004, e-pub. Jan. 22, 2004). "Identification and Characterization of a Very Low Density Lipoprotein Receptor-Binding Peptide From Tissue Factor Pathway Inhibitor That Has Antitumor and Antiangiogenic Activity," *Blood* 103(9):3374-3380.

Hilpert, K. et al. (Aug. 2005, e-pub. Jul. 24, 2005). "High-Throughput Generation of Small Antibacterial Peptides With Improved Activity," *Nat. Biotechnol.* 23(8):1008-1012.

Hoffman, M. et al. (Aug. 1990). "Characteristics of the Chemotactic Activity of Heparin Cofactor II Proteolysis Products," *J. Leukoc. Biol.* 48(2):156-162.

Hoffman, M. et al. (Oct. 2003). "Localization of Heparin Cofactor II in Injured Human Skin: A Potential Role in Wound Healing," *Exp. Mol. Pathol.* 75(2):109-118.

Hubbell, J.A. (Jun. 1995). "Biomaterials in Tissue Engineering," *Biotechnology* 13(6):565-576.

Jenssen, H. et al. (Aug. 2007). "Evaluating Different Descriptors for Model Design of Antimicrobial Peptides With Enhanced Activity Toward *P. Aeruginosa*," *Chem. Biol. Drug Des.* 70(2):134-142.

Jones, A.L et al. (Apr. 2005). "Histidine-Rich Glycoprotein: A Novel Adaptor Protein in Plasma That Modulates the Immune, Vascular and Coagulation Systems," *Immunol Cell Biol.* 83(2):106-118.

Kalle, M. et al. (Jun. 15, 2013, e-pub. May 8, 2013). "Proteolytic Activation Transforms Heparin Cofactor II into a Host Defense Molecule," *J. Immunol.* 190(12):6303-6310.

Karima, R. et al. (Mar. 1999). "The Molecular Pathogenesis of Endotoxic Shock and Organ Failure," *Mol. Med. Today* 5(3):123-132.

Kichler, A. et al. (Feb. 18, 2003). "Histidine-Rich Amphipathic Peptide Antibiotics Promote Efficient Delivery of DNA Into Mammalian Cells," *PNAS* 100(4):1564-1568.

Kirikae, T. et al. (May 1998). "Protective Effects of a Human 18-Kilodalton Cationic Antimicrobial Protein (CAP18)-Derived Peptide Against Murine Endotoxemia," *Infect. Immun.* 66(5):1861-1868.

Kowalska, K. et al. (Jul. 5, 2002). "Direct Antimicrobial Properties of Substance P," *Life Sci.* 71(7):747-750.

Lehrer, R.I. et al. (Jan. 2002). "Cathelicidins: A Family of Endogenous Antimicrobial Peptides," *Curr. Opin. Hematol.* 9(1):18-22.

Lehrer, R.I. et al. (Mar. 21, 1991). "Ultrasensitive Assays for Endogenous Antimicrobial Polypeptides," *J. Immunol. Methods* 137(2): 167-173.

Li, A. et al. (Sep. 1998). "Proteolysis of Tissue Factor Pathway Inhibitor (TFPI) by Plasmin: Effect on TFPI Activity," *Thromb. Haemost.* 80(3):423-427.

Lu, Y.C. et al (May 2008). "LPS/TLR4 Signal Transduction Pathway," *Cytokine* 42(2):145-151.

Lwaleed, B.A. et al. (Feb. 2006, e-pub. Nov. 2005). "Tissue Factor Pathway Inhibitor: Structure, Biology and Involvement in Disease," *J. Pathol.* 208(3):327-339.

Malmsten, M. et al. (Jul. 2006). "Bacterial Killing by Heparin-Binding Peptides from PRELP and Thrombospondin," *Matrix Biol.* 25(5): 294-300.

Malmsten, M. et al. (Feb. 2007). "Antimicrobial Peptides Derived from Growth Factors," *Growth Factors* 25(1):60-70.

Marr, A.K. et al. (Oct. 2006). "Antibacterial Peptides for Therapeutic Use: Obstacles and Realistic Outlook," *Curr. Opin. Pharmacol.* 6(5):468-472.

Meziere, C. et al. (Oct. 1, 1997). "In Vivo T Helper Cell Response to Retro-Inverso Peptidomimetics," *J. Immunol.* 159(7):3230-3237.

Michie, H.R. et al. (Jun. 9, 1988). "Detection of Circulating Tumor Necrosis Factor After Endotoxin Administration," *N. Engl. J. Med.* 318(23):1481-1486.

Mine, S. et al. (Jan. 8, 2002). "Structural Mechanism for Heparin-Binding of the Third Kunitz Domain of Human Tissue Factor Pathway Inhibitor," *Biochemistry* 41(1):78-85.

Mor, A. et al. (May 31, 1994). "Structure, Synthesis, and Activity of Dermaseptin b, a Novel Vertebrate Defensive Peptide from Frog Skin: Relationship with Adenoregulin," *Biochemistry* 33(21):6642-6650.

Nakatomi, K. et al. (Aug. 1998). "Neutrophils Responded to Immobilized Lipopolysaccharide in the Absence of Lipopolysaccharide-Binding Protein," *J. Leukoc. Biol.* 64(2):177-184.

Noda, A. et al. (Jul. 2002). "Plasma Levels of Heparin Cofactor II (HCII) and Thrombin-HCII Complex in Patients with Disseminated Intravascular Coagulation," *Clin. Appl. Thromb. Hemost.* 8(3):265-271.

(56) References Cited

OTHER PUBLICATIONS

Nordahl, E.A. et al. (Oct. 14, 2005). "Domain 5 of High Molecular Weight Kininogen is Antibacterial," *J. Biol. Chem.* 280(41):34832-34839.
Nordahl, E.A. et al. (Nov. 30, 2004). "Activation of the Complement System Generates Antibacterial Peptides," *PNAS* 101(48):16879-16884.
Ohkura, N. et al. (Sep. 1, 1997). "A Novel Degradation Pathway of Tissue Factor Pathway Inhibitor: Incorporation into Fibrin Clot and Degradation by Thrombin," *Blood* 90(5):1883-1892.
Olsson, A.K. et al. (Jan. 2004). "A Fragment of Histidine-Rich Glycoprotein is a Potent Inhibitor of Tumor Vascularization," *Cancer Res.* 64(2):599-605.
Opal, S.M. (Sep. 2007). "The Host Response to Endotoxin, Antilipopolysaccharide Strategies, and the Management of Severe Sepsis," *Int. J. Med. Microbiol.* 297(5):365-377.
Papareddy, P. et al. (Apr. 22, 2010). "Proteolysis of Human Thrombin Generates Novel Host Defense Peptides," *PLoS Pathog* 6(4):e1000857, 15 pages Total.
Park, C.T. et al (Jun. 15, 1997). Tissue Factor Pathway Inhibitor Blocks Cellular Effects of Endotoxin by Binding to Endotoxin and Interfering with Transfer to CD14, *Blood* 89(12):4268-4274.
Park, E. et al. (Aug. 1993). "Taurine Chloramine Inhibits the Synthesis of Nitric Oxide and the Release of Tumor Necrosis Factor in Activated RAW 264.7 Cells," *J. Leukoc. Biol.* 54(2):119-124.
Pasupuleti, M. et al. (Jan. 26, 2007). "Preservation of Antimicrobial Properties of Complement Peptide C3a, from Invertebrates to Humans," *J. Biol. Chem.* 282(4):2520-2528.
Pasupuleti, M. et al. (2008). "Rational Design of Antimicrobial C3a Analogues with Enhanced Effects Against *Staphylococci* Using an Integrated Structure and Function-Based Approach," *Biochemistry* 47(35):9057-9070.
Pollock, J.S. et al. (Dec. 1, 1991). Purification and Characterization of Particulate Endothelium-Derived Relaxing Factor Synthase from Cultured and Native Bovine Aortic Endothelial Cells, *PNAS* 88(23):10480-10484.
Rau, J.C. et al. (Jul. 2007). "Serpins in Thrombosis, Hemostasis and Fibrinolysis," *J. Thromb. Haemost.* 5(Suppl 1):102-115.
Rydengard, V. et al. (Aug. 1, 2008). "Histidine-Rich Glycoprotein Protects from Systemic *Candida* Infection," *PLoS Pathog* 4(8):e1000116, 12 Pages Total.
Rydengard, V. et al. (Jan. 2007). "Histidine-Rich Glycoprotein Exerts Antibacterial Activity," *FEBS J.* 274(2):377-389.
Rydengard, V. et al. (Jun. 2006). "Zinc Potentiates the Antibacterial Effects of Histidine-Rich Peptides Against *Enterococcus Faecalis*," *FEBS J.* 273(11):2399-2406.
Sajjan, U.S. et al. (Dec. 2001). "P-113D, an Antimicrobial Peptide Active Against *Pseudomonas Aeruginosa*, Retains Activity in the Presence of Sputum from Cystic Fibrosis Patients," *Antimicrob. Agents Chemother.* 45(12):3437-3444.
Sato, H. (Jun. 17, 2002). "Enzymatic Procedure for Site-Specific Pegylation of Proteins," *Adv. Drug Deliv. Rev.* 54(4):487-504.
Sauter, C. Et al. (Oct. 18, 1980). "Interferon in Human Serum After Injection of Endotoxin," *Lancet* 2(8199):852-853.
Schirm, S. et al (Jun. 15, 2009). "Fragmented tissue factor pathway inhibitor (TFPI) and TFPI C-terminal peptides eliminate serum-resistant *Escherichia coli* from blood cultures," *Journal of Infectious Diseases* 199(12):1807-1815.
Schmidtchen, A. et al. (Jan. 2003). "Elastase-Producing *Pseudomonas Aeruginosa* Degrade Plasma Proteins and Extracellular Products of Human Skin and Fibroblasts, and Inhibit Fibroblast Growth," *Microb. Pathog.* 34(1):47-55.
Schwartz, D. et al. (May 1999). "Nitric Oxide, Sepsis, and the Kidney," *Semin. Nephrol.* 19(3):272-276.
Sheffield, W.P. et al. (May 29, 1995). "Deletion Mutagenesis of Heparin Cofactor II: Defining the Minimum Size of a Thrombin Inhibiting Serpin," *FEBS Letters* 365(2-3):189-192.
Singh, S. et al. (Jun. 24, 2013). "Importance of Lipopolysaccharide Aggregate Disruption for the Anti-Endotoxic Effects of Heparin Cofactor II Peptides," *Biochem. Biophys. Acta.*, pp. 1-11.

Sjögren, H. et al. (Jun. 1, 2005). "Comparison of the Helix-Coil Transition of a Titrating Polypeptide in Aqueous Solutions and at the Air-Water Interface," *Biophys. Chem.* 116(1):11-21.
Strömstedt, A.A. et al, (Feb. 2009, e-pub. Nov. 24, 2008). "Evaluation of Strategies for Improving Proteolytic Resistance of Antimicrobial Peptides by Using Variants of EFK17, an Internal Segment of LL-37," *Antimicrobial Agents Chemother.* 53(2):593-602.
Taboureau, O. et al. (Jul. 2006). "Design of Novispirin Antimicrobial Peptides by Quantitative Structure-Activity Relationship," *Chem. Biol. Drug Des.* 68(1):48-57.
Thompson, J.D. et al. (Nov. 11, 1994). "Clustal W: Improving the Sensitivity of Progressive Multiple Sequence Alignment Through Sequence Weighting, Position-Specific Gap Penalties and Weight Matrix Choice," *Nuc. Acid Res.* 22(22):4673-4680.
Thorsett, E.D. et al. (Feb. 28, 1983). "Dipeptide Mimics. Conformationally Restricted Inhibitors of Angiotensin-Converting Enzyme," *Biochem. Biophys. Res. Comm.* 111(1):166-171.
Tollefsen, D.M. (Nov. 1995). Insight into the Mechanism of Action of Heparin Cofactor II, *Thromb. Haemost.* 74(5):1209-1214.
Tossi, A. et al. (2000). "Amphipathic, α-helical Antimicrobial Peptides," *Biopolymers* 55(1):4-30.
Tsuchida-Straeten, N. et al. (May 2005). "Enhanced Blood Coagulation and Fibrinolysis in Mice Lacking Histidine-Rich Glycoprotein (HRG)," *J. Thromb. Haemost.* 3(5):865-872.
Ulevitch, R.J. (Mar. 1978). "The Preparation and Characterization of a Radioiodinated Bacterial Lipopolysaccharide," *Immunochemistry* 15(3):157-164.
Veber, D.F. et al. (Jun. 1978). Conformationally Restricted Bicyclic Analogs of Somatostatin, *PNAS* 75(6):2636-2640.
Veronese, F.M. et al. (Jun. 17, 2002). "Introduction and Overview of Peptide and Protein Pegylation," *Adv. Drug Deliv. Rev.* 54(4):453-456.
Veronese, F.M. et al. (Nov. 1, 2005). "PEGylation, Successful Approach to Drug Delivery," *Drug Discov. Today* 10(21):1451-1458.
Wang, Y.S. et al. (Jun. 17, 2002). "Structural and Biological Characterization of Pegylated Recombinant Interferon α-2b and its Therapeutic Implications," *Adv. Drug Deliv. Rev.* 54(4):547-570.
Wei, X.Q. et al., (Jun. 1, 1995). "Altered Immune Responses in Mice Lacking Inducible Nitric Oxide Synthase," *Nature* 375(6530):408-411.
Werthen, M. et al. (Oct. 2004). "*Pseudomonas Aeruginosa*—Induced Infection and Degradation of Human Wound Fluid and Skin Proteins Ex Vivo are Eradicated by a Synthetic Cationic Polymer," *J. Antimicrob. Chemother.* 54(4):772-779.
Wesselschmidt, R. et al. (1Apr. 1, 1992). "Tissue Factor Pathway Inhibitor: The Carboxy-Terminus is Required for Optimal Inhibition of Factor Xa," *Blood* 79(8):2004-2010.
Wiegand, I. et al (2008). "Agar and Broth Dilution Methods to Determine the Minimal Inhibitory Concentration (MIC) of Antimicrobial Substances," Nat. Protoc. 3(2):163-175.
Wurfel, M.M. et al. (Dec. 15, 1997). "Targeted Deletion of the Lipopolysaccharide (LPS)-Binding Protein Gene Leads to Profound Suppression of LPS Responses Ex Vivo, Whereas in Vivo Responses Remain Intact," *J. Exp. Med.* 186(12):2051-2056.
Yount, N.Y. et al. (2006). "Advances in Antimicrobial Peptide Immunobiology," *Biopolymers* 84(5):435-458.
Zanetti, M. (Jan. 2004). "Cathelicidins, Multifunctional Peptides of the Innate Immunity," *J. Leukoc. Biol.* 75(1):39-48.
Zasloff, M. (Jan. 24, 2002). "Antimicrobial Peptides of Multicellular Organisms," *Nature* 415(6870):389-395.
Baglin, T. et al. (2002). "Crystal structures of native and thrombin-complexed heparin cofactor II reveal a multistep allosteric mechanism," *PNAS* 99(17):11079-11084.
Bauman, S. et al. (1999). "Enhancement of Heparin Cofactor II Anticoagulant Activity," *J. Biol. Chem.* 274:49(34556-34565).
Church, F. et al. (1991). "Leukocyte Chemoattractant Peptides from the Serpin Heparin Cofactor II," *J. Biol. Chem.* 266:2 (704-709).
Maekawa, H. et al. (2000). "Thrombin Inhibition by HCII in the Presence of Elastase-cleaved HCII and Thrombin-HCII Complex," *Thrombosis Research* 100:443-451.
Zhou, X. et al. (2012). "Phylogenomic Analysis Resolves the Interordinal Relationships and Rapid Diversification of the Laurasiatherian Mammals," *Syst. Biol.* 61(1):150-164.

\* cited by examiner

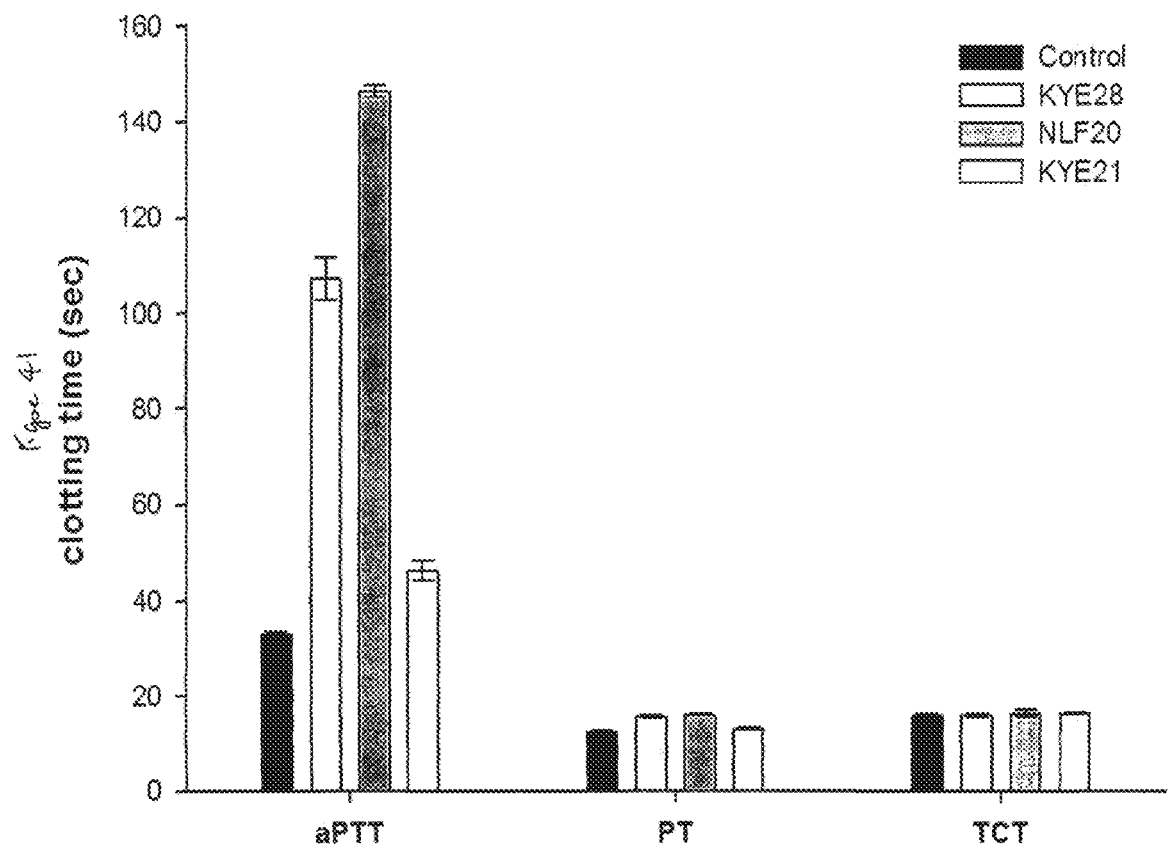

HEPARIN COFACTOR II FRAGMENTS WITH ANTI-INFLAMMATORY AND ANTI-COAGULANT ACTIVITY

CROSS-REFERENCE TO RELATED APPLICATIONS

This application is a National Phase application under 35 U.S.C. §371 of International Application No. PCT/GB2010/001780 filed Sep. 21, 2010 and claims the benefit of Great Britain Application No. 0916578.8 filed Sep. 22, 2009, the disclosures of which are incorporated herein by reference in their entirety.

FIELD OF THE INVENTION

The present invention relates to novel polypeptides derived from a naturally occurring protein which modulates blood coagulation, heparin cofactor II (HCII), and their use in the treatment and prevention of inflammation and/or excessive coagulation. In particular, the invention provides polypeptides comprising or consisting of an amino acid sequence of SEQ ID NO: 1 to 3, or a fragment, variant, fusion or derivative thereof, or a fusion of said fragment, variant or derivative thereof, for use in medicine, e.g. in the treatment or prevention of inflammation and/or excessive coagulation.

INTRODUCTION

Infectious and inflammatory diseases account for millions of deaths worldwide each year and incur tremendous health care costs. The disease spectrum is broad and includes acute disease, such as erysipelas, sepsis, pneumonia and numerous other infections, having a direct association to a given pathogen, as well as chronic diseases, where microbes often cause a long-standing inflammatory state. Sepsis is an infection-induced syndrome characterized by a generalized inflammatory state and represents a frequent complication in the surgical patient, in immunocompromized patients, or in relation to burns. Severe sepsis is a common, expensive and frequently fatal condition, having a documented worldwide incidence of 1.8 million each year, but this number is confounded by a low diagnostic rate and difficulties in tracking sepsis in many countries. It is estimated that with an incidence of 3 in 1000 the true number of cases each year reaches 18 million, and with a mortality rate of almost 30% it becomes a leading cause of death worldwide. Sepsis costs on average US$22 000 per patient, and its treatment therefore has a great impact on hospitals' financial resources, with US$16.7 billion each year being spent in the USA alone. The cost of treating an ICU patient with sepsis is six times greater than that of treating a patient without sepsis. In other settings, harmful inflammatory cascades are initiated by other mechanisms than bacterial, such as during trauma, surgery, extracorporeal circulation, ischemia, burns, drug reactions, hemorrhagic shock, toxic epidermal necrolysis, transfusion reactions, leading to ARDS or SIRS. Chronic obstructive pulmonary disorder (COPD) refers to a range of chronic disorders in the airways characterized by irreversible and progressing decline in airflow to the lung capillaries. Although several factors contribute to the development of COPD, smoking and recurring infections are the most important causes. COPD predominantly develops in long-term smokers from their late-30s and progressively develops in an irreversible fashion. According to 2007 estimates by WHO, there are currently 210 million patients with COPD, and 3 million people died of COPD in 2005. WHO also predicts that COPD will become the fourth leading cause of death worldwide by 2030. Several factors are expected to contribute to this increase, including increased diagnosis rates, lack of treatments that reverse the inflammatory disease progression, and a globally ageing population burden. Microbes cause, and/or aggravate, a spectrum of diseases including bacterial conjunctivitis and keratitis, otitis, postoperative and burn wound infections, chronic leg ulcers, pneumonia, and cystic fibrosis.

New agents addressing infection are therefore needed, and there is significant interest in the potential use of AMPs as novel treatment modalities (Marr, A. K., W. J. Gooderham, et al. (2006). *Curr Opin Pharmacol* 6(5): 468-472). Considering the increasing resistance problems against conventional antibiotics, antimicrobial peptides have recently emerged as potential therapeutic candidates. AMPs provides a first line of defense against invading microbes in almost all organisms (Tossi, A., L. Sandri, et al. (2000). *Biopolymers* 55(1): 4-30; Lehrer, R. I. and T. Ganz (2002). *Curr Opin Hematol* 9(1): 18-22; Zasloff, M. (2002). *Nature* 415(6870): 389-95; Yount, N. Y., A. S. Bayer, et al. (2006). *Biopolymers* 84: 435-458; Harder, J., R. Glaser, et al. (2007). *J Endotoxin Res* 13(6): 317-38). Ideally, AMP should display high bactericidal potency, but low toxicity against (human) eukaryotic cells. Various strategies, such as use of combinational library approaches (Blondelle, S. E. and K. Lohner (2000). *Biopolymers* 55(1): 74-87), stereoisomers composed of D-amino acids (Sajjan, U. S., L. T. Tran, et al. (2001). *Antimicrob Agents Chemother* 45(12): 3437-44) or cyclic D,L-α-peptides (Fernandez-Lopez, S., H. S. Kim, et al. (2001). *Nature* 412(6845): 452-5), high-throughput based screening assays (Hilpert, K., R. Volkmer-Engert, et al. (2005). *Nat Biotechnol* 23(8): 1008-12; Taboureau, O., O. H. Olsen, et al. (2006). *Chem Biol Drug Des* 68(1): 48-57), quantitative structure-activity relationship (QSAR) approaches (Hilpert, K., R. Volkmer-Engert, et al. (2005). *Nat Biotechnol* 23(8): 1008-12; Marr, A. K., W. J. Gooderham, et al. (2006). *Curr Opin Pharmacol* 6(5): 468-472; Jenssen, H., T. Lejon, et al. (2007). *Chem Biol Drug Des* 70(2): 134-42; Pasupuleti, M., B. Walse, et al. (2008). *Biochemistry* 47(35): 9057-70), and identification of endogenous peptides (Papareddy, P., V. Rydengard, et al. *PLoS Pathoq* 6(4): e1000857; Nordahl, E. A., V. Rydengard, et al. (2005). *J Biol Chem* 280(41): 34832-9; Malmsten, M., M. Davoudi, et al. (2006). *Matrix Biol* 25(5): 294-300; Malmsten, M., M. Davoudi, et al. (2007). *Growth Factors* 25(1): 60-70; Pasupuleti, M., B. Walse, et al. (2007). *J Biol Chem* 282(4): 2520-8) are currently employed for identifying selective and therapeutically interesting AMPs (Hancock, R. E. and H. G. Sahl (2006). *Nat Biotechnol* 24(12): 1551-7; Marr, A. K., W. J. Gooderham, et al. (2006). *Curr Opin Pharmacol* 6(5): 468-472). Despite the potential of these approaches, naturally occurring peptide epitopes may show advantages in a therapeutic setting considering low immunogenecity as well as inherent additional biological functions.

The coagulation cascade also represents a fundamental system activated in response to injury and infection (Davie, E. W. and J. D. Kulman, Semin Thromb Hemost, 2006. 32 Suppl 1: p. 3-15; Bode, W., Semin Thromb Hemost, 2006. 32 Suppl 1: p. 16-31). Through a series of cascade-like proteinase activation steps, thrombin is formed, leading to fibrinogen degradation and clot formation. The coagulation cascade is controlled by various regulatory proteins, such as heparin cofactor II (HCII), antithrombin III (ATIII) (two serine proteinase inhibitors, serpins), protein C inhibitor, and tissue factor proteinase inhibitor (TFPI) Furthermore, histidine-rich glycoprotein may modulate coagulation by interacting with fibrinogen as well as plasminogen.

Heparin cofactor II is a 66.5 kDa, 480 amino acid glycoprotein present in plasma at ~80 ug/ml. However, although HCII blocks free and clot-associated thrombin, its exact physiological role is not fully understood. Similar to antithrombin III, the inhibition of thrombin by HCII is accelerated by glycosaminoglycans, such as heparin (Tollefsen, 1995 *Thromb Haemost*. 74(5): 1209-14.). While ATIII deficiency is clearly linked to thrombosis, HCII homozygous deficient mice do not suffer from thrombophilia under normal conditions. Plasma concentrations of HCII are significantly decreased during inflammation and infection (Noda et al. (2002), *Clin. Appl. Thromb. Hemost.*, 8(3): 265-271). Indeed, recent evidence suggest that the primary physiological function of HCII is to inhibit thrombin's non-hemostatic roles such as in the development of atherosclerosis (Rau, J. C., L. M. Beaulieu, et al. (2007). *J Thromb Haemost* 5 Suppl 1: 102-15). It has also been shown that HCII could function as an extravascular thrombin inhibitor and may play a role in the regulation of wound healing (Hoffman, Loh et al. 2003), and furthermore, chemotactic products have been described upon proteoloysis of HCII (Hoffman, M., C. W. Pratt, et al. (1990). *J Leukoc Biol* 48(2): 156-62), further illustrating the potential latent biological activities of this antiproteinase. Structural studies on HCII have revealed that the molecule undergoes an unusual conformational change, termed the Stressed to Relaxed (S to R) transition. The inventors have made the unexpected discovery that a series of peptides derived from HCII have antiinflammatory and anticoagulative functions, thus representing a previously unknown property of HCII derived peptides.

The present invention seeks to provide new polypeptide agents, derived from heparin cofactor II, for use in medicine, for example in the treatment or prevention of inflammation and/or excessive coagulation of the blood.

SUMMARY OF THE INVENTION

A first aspect of the invention provides a polypeptide comprising or consisting of an amino acid sequence derived from a naturally occurring protein which modulates blood coagulation, namely heparin cofactor II, or a fragment, variant, fusion or derivative thereof, or a fusion of said fragment, variant or derivative thereof, for use in the treatment or prevention of inflammation and/or excessive coagulation, wherein the fragment, variant, fusion or derivative exhibits an anti-inflammatory and/or anticoagulant activity.

The invention derives from the unexpected discovery by the inventors that naturally occurring proteins which modulate blood coagulation (such as heparin cofactor II) comprise "cryptic peptides" within their internal regions, which exhibit anti-inflammatory activity. It is believed that such peptides may be 'released' by cleavage of the parent antiproteinase holoprotein in response to wounding and other physiological challenges, or that they represent an active epitope in the holoprotein which is activated during proteolysis and formation of the R form. Thus, the polypeptides of the invention constitute a novel and previously undisclosed class of host defense peptides (HDPs), which have therapeutic potential against disorders and conditions associated with inflammation.

By "naturally occurring protein which modulates blood coagulation" we include all naturally occurring proteins which modulates blood coagulation which modulate, either positively or negatively, the blood coagulation process. Such modulatory activity may be determined by methods well known in the art, for example using the activated partial thromboplastin time (aPTT) test, the prothrombin time (PT) test, or the thrombin clotting time (TCT) test. Furthermore, specific measurements of prekallikrein activation or the activity of Factor X and other coagulation factors may be performed. It will be appreciated by persons skilled in the art that the naturally occurring protein may modulate blood coagulation directly or indirectly.

By an amino acid sequence "derived from" a naturally occurring protein which modulates blood coagulation, we mean that the amino acid sequence is found within the amino acid sequence of the naturally occurring protein. For example, in one embodiment the amino acid sequence may be from a region of a naturally occurring protein which modulates blood coagulation.

By "anti-inflammatory activity" we mean an ability to reduce or prevent one or more biological processes associated with inflammatory events. Such anti-inflammatory activity of polypeptides may be determined using methods well known in the art, for example by measuring LPS-induced release of pro-inflammatory cytokines from macrophages (e.g. TNFα, IL-6, IF-γ), or neutrophils (see Examples below). Other relevant assays comprise effects of lipoteichoic acid, zymosan, DNA, RNA, flagellin or peptidoglycan in the above systems as well as determination of regulation at the transcriptional level (e.g. Gene-array, qPCR etc). Furthermore, dendritic cell activation or activation of thrombocytes may also be used as a measure of anti-inflammatory activity.

By "anti-coagulant activity" we mean an ability to increase the prothrombin time (PT), the thrombin clotting time (TCT) and/or the activated partial thromboplastin time (aPTT). Alternatively, peripheral blood mononuclear cells (PB-MNC)s can be stimulated by *E. coli* LPS with or without the peptide and tissue factor and clot formation followed after addition of human plasma, or clotting times for whole blood can be measured.

It will be appreciated by persons skilled in the art that the invention encompasses polypeptides comprising or consisting of an amino acid sequence derived from heparin cofactor II, which modulates blood coagulation, as well as fragments, variants, fusions and derivatives of such amino acid sequence which retain an anti-inflammatory activity. Preferably, however, the polypeptide is not a naturally occurring protein, e.g. a holoprotein (although it will, of course, be appreciated that the polypeptide may constitute an incomplete portion or fragment of a naturally occurring protein).

In one embodiment of the polypeptides of the invention, the polypeptide comprises a heparin-binding domain. By "heparin-binding domain" we mean an amino acid sequence within the polypeptide which is capable of binding heparin under physiological conditions. Such sequences often comprise XBBXB and XBBBXXB (where B=basic residue and X=hydropathic or uncharged residue), or clusters of basic amino acids (XBX, XBBX, XBBBX). Spacing of such clusters with non-basic residues (BXB, BXXB) may also occur. Additionally, a distance of approximately 20 Å between basic amino acids constitutes a prerequisite for heparin-binding.

It will be appreciated by persons skilled in the art that the heparin cofactor II may be from a human or non-human source. For example, the heparin cofactor II may be derived (directly or indirectly) from a non-human mammal, such as an ape (e.g. chimpanzee, bonobo, gorilla, gibbon and orangutan), monkey (e.g. macaque, baboon and colobus), rodent (e.g. mouse, rat) or ungulates (e.g. pig, horse and cow).

In one preferred embodiment, the heparin cofactor II is human heparin cofactor II (for example, see Swiss Port Accession No. P05546.

For example, the polypeptide may comprise or consist of the amino acid sequence of any one of SEQ ID NOS:1 to 3:

"KYE28":
KYEITTIHNLFRKLTHRLFRRNFGYTLR [SEQ ID NO: 1]

"KYE21":
KYEITTIHNLFRKLTHRLFRR [SEQ ID NO: 2]

"NLF20":
NLFRKLTHRLFRRNFGYTLR [SEQ ID NO: 3]

or a fragment, variant, fusion or derivative thereof, or a fusion of said fragment, variant or derivative thereof, which retains an anti-inflammatory and/or anticoagulant activity of any one of SEQ ID NOS:1 to 3.

It will be appreciated by persons skilled in the art that the term 'amino acid', as used herein, includes the standard twenty genetically-encoded amino acids and their corresponding stereoisomers in the 'D' form (as compared to the natural 'L' form), omega-amino acids other naturally-occurring amino acids, unconventional amino acids (e.g., α,α-disubstituted amino acids, N-alkyl amino acids, etc.) and chemically derivatised amino acids (see below).

When an amino acid is being specifically enumerated, such as 'alanine' or 'Ala' or 'A', the term refers to both L-alanine and D-alanine unless explicitly stated otherwise. Other unconventional amino acids may also be suitable components for polypeptides of the present invention, as long as the desired functional property is retained by the polypeptide. For the peptides shown, each encoded amino acid residue, where appropriate, is represented by a single letter designation, corresponding to the trivial name of the conventional amino acid.

In one embodiment, the polypeptides of the invention comprise or consist of L-amino acids.

Where the polypeptide comprises an amino acid sequence according to a reference sequence (for example, SEQ ID NOs: 1 to 3), it may comprise additional amino acids at its N- and/or C-terminus beyond those of the reference sequence, for example, the polypeptide may comprise additional amino acids at its N-terminus. Likewise, where the polypeptide comprises a fragment, variant or derivative of an amino acid sequence according to a reference sequence, it may comprise additional amino acids at its N- and/or C-terminus.

In a further embodiment the polypeptide comprises or consists of a fragment of the amino acid sequence according to a reference sequence (for example, SEQ ID NOs: 1 to 3). Thus, the polypeptide may comprise or consist of at least 5 contiguous amino acid of the reference sequence, for example at least 6, 7, 8, 9, 10, 11, 12, 13, 14, 15, 16, 17, 18, 19, 20, 21, 22, 23, 24, 25, 26 or 27 contiguous amino acids, e.g. of SEQ ID NO: 1.

In one embodiment the polypeptide fragment commences at an amino acid residue selected from amino acid residues 1, 2, 3, 4, 5, 6, 7, 8, 9, 10, 11, 12, 13, 14, 15, 16, 17, 18, 19, 20, 21, 22 and 23 of SEQ ID NO:1. Alternatively/additionally, the polypeptide fragment may terminate at an amino acid residue selected from amino acid residues 5, 6, 7, 8, 9, 10, 11, 12, 13, 14, 15, 16, 17, 18, 19, 20, 21, 22, 23, 24, 25, 26 or 27 of SEQ ID NO:1.

For example, the polypeptide fragment may comprise or consist of amino acids 9 to 28 of SEQ ID NO: 1.

It will be appreciated by persons skilled in the art that the polypeptide of the invention may comprise or consist of a variant of the amino acid sequence according to a reference sequence (for example, SEQ ID NO: 1 to 3), or fragment of said variant. Such a variant may be non-naturally occurring.

By 'variants' of the polypeptide we include insertions, deletions and substitutions, either conservative or non-conservative. For example, conservative substitution refers to the substitution of an amino acid within the same general class (e.g. an acidic amino acid, a basic amino acid, a non-polar amino acid, a polar amino acid or an aromatic amino acid) by another amino acid within the same class. Thus, the meaning of a conservative amino acid substitution and non-conservative amino acid substitution is well known in the art. In particular we include variants of the polypeptide which exhibit an anti-inflammatory activity.

In a further embodiment the variant has an amino acid sequence which has at least 50% identity with the amino acid sequence according to a reference sequence (for example, SEQ ID NO: 1 to 3) or a fragment thereof, for example at least 55%, 60%, 65%, 70%, 75%, 80%, 85%, 90%, 95%, 96%, 97%, 98% or at least 99% identity.

The percent sequence identity between two polypeptides may be determined using suitable computer programs, for example the GAP program of the University of Wisconsin Genetic Computing Group and it will be appreciated that percent identity is calculated in relation to polypeptides whose sequences have been aligned optimally.

The alignment may alternatively be carried out using the Clustal W program (as described in Thompson et al., 1994, Nuc. Acid Res. 22:4673-4680, which is incorporated herein by reference).

The parameters used may be as follows:
Fast pairwise alignment parameters: K-tuple (word) size; 1, window size; 5, gap penalty; 3, number of top diagonals; 5. Scoring method: x percent.
Multiple alignment parameters: gap open penalty; 10, gap extension penalty; 0.05.
Scoring matrix: BLOSUM.

Alternatively, the BESTFIT program may be used to determine local sequence alignments.

In one embodiment, amino acids from the above reference sequences may be mutated in order to reduce proteolytic degradation of the polypeptide, for example by I, F to W modifications (see Strömstedt et al, *Antimicrobial Agents Chemother* 2009, 53, 593).

Variants may be made using the methods of protein engineering and site-directed mutagenesis well known in the art using the recombinant polynucleotides (see example, see *Molecular Cloning: a Laboratory Manual*, 3rd edition, Sambrook & Russell, 2000, Cold Spring Harbor Laboratory Press, which is incorporated herein by reference).

In one embodiment, the polypeptide comprises or consists of an amino acid which is a species homologue of any one of the above amino acid sequences (e.g. SEQ ID NOS: 1 to 3). By "species homologue" we include that the polypeptide corresponds to the same amino acid sequence within an equivalent protein from a non-human species, i.e. which polypeptide exhibits the maximum sequence identity with of any one of SEQ ID NOS: 1 to 3 (for example, as measured by a GAP or BLAST sequence comparison). Typically, the species homologue polypeptide will be the same length as the human reference sequence (i.e. SEQ ID NOS: 1 to 3).

In a still further embodiment, the polypeptide comprises or consists of a fusion protein.

By 'fusion' of a polypeptide we include an amino acid sequence corresponding to a reference sequence (for example, SEQ ID NO: 1 to 3, or a fragment or variant thereof) fused to any other polypeptide. For example, the said polypeptide may be fused to a polypeptide such as glutathione-S-transferase (GST) or protein A in order to facilitate purification of said polypeptide. Examples of such fusions are well known to those skilled in the art. Similarly, the said polypeptide may be fused to an oligo-histidine tag such as His6 or to an epitope recognised by an antibody such as the well-known Myc tag epitope. In addition, fusions comprising a hydrophobic oligopeptide end-tag may be used. Fusions to any variant or derivative of said polypeptide are also included in the scope of the invention. It will be appreciated that fusions (or variants or derivatives thereof) which retain desirable properties, such as an anti-inflammatory activity, are preferred.

The fusion may comprise a further portion which confers a desirable feature on the said polypeptide of the invention; for example, the portion may be useful in detecting or isolating the polypeptide, or promoting cellular uptake of the polypeptide. The portion may be, for example, a biotin moiety, a streptavidin moiety, a radioactive moiety, a fluorescent moiety, for example a small fluorophore or a green fluorescent protein (GFP) fluorophore, as well known to those skilled in the art. The moiety may be an immunogenic tag, for example a Myc tag, as known to those skilled in the art or may be a lipophilic molecule or polypeptide domain that is capable of promoting cellular uptake of the polypeptide, as known to those skilled in the art.

It will be appreciated by persons skilled in the art that the polypeptide of the invention may comprise one or more amino acids that are modified or derivatised, for example by PEGylation, amidation, esterification, acylation, acetylation and/or alkylation.

As appreciated in the art, pegylated proteins may exhibit a decreased renal clearance and proteolysis, reduced toxicity, reduced immunogenicity and an increased solubility [Veronese, F. M. and J. M. Harris, Adv Drug Deliv Rev, 2002. 54(4): p. 453-6., Chapman, A. P., Adv Drug Deliv Rev, 2002. 54(4): p. 531-45.]. Pegylation has been employed for several protein-based drugs including the first pegylated molecules asparaginase and adenosine deaminase [Veronese, F. M. and J. M. Harris, Adv Drug Deliv Rev, 2002. 54(4): p. 453-6., Veronese, F. M. and G. Pasut, Drug Discov Today, 2005. 10(21): p. 1451-8.].

In order to obtain a successfully pegylated protein, with a maximally increased half-life and retained biological activity, several parameters that may affect the outcome are of importance and should be taken into consideration. The PEG molecules may differ, and PEG variants that have been used for pegylation of proteins include PEG and monomethoxy-PEG. In addition, they can be either linear or branched [Wang, Y. S., et al., Adv Drug Deliv Rev, 2002. 54(4): p. 547-70]. The size of the PEG molecules used may vary and PEG moieties ranging in size between 1 and 40 kDa have been linked to proteins [Wang, Y. S., et al., Adv Drug Deliv Rev, 2002. 54(4): p. 547-70., Sato, H., Adv Drug Deliv Rev, 2002. 54(4): p. 487-504, Bowen, S., et al., Exp Hematol, 1999. 27(3): p. 425-32, Chapman, A. P., et al., Nat Biotechnol, 1999. 17(8): p. 780-3]. In addition, the number of PEG moieties attached to the protein may vary, and examples of between one and six PEG units being attached to proteins have been reported [Wang, Y. S., et al., Adv Drug Deliv Rev, 2002. 54(4): p. 547-70., Bowen, S., et al., Exp Hematol, 1999. 27(3): p. 425-32]. Furthermore, the presence or absence of a linker between PEG as well as various reactive groups for conjugation have been utilised. Thus, PEG may be linked to N-terminal amino groups, or to amino acid residues with reactive amino or hydroxyl groups (Lys, His, Ser, Thr and Tyr) directly or by using γ-amino butyric acid as a linker. In addition, PEG may be coupled to carboxyl (Asp, Glu, C-terminal) or sulfhydryl (Cys) groups. Finally, Gln residues may be specifically pegylated using the enzyme transglutaminase and alkylamine derivatives of PEG has been described [Sato, H., Adv Drug Deliv Rev, 2002. 54(4): p. 487-504].

It has been shown that increasing the extent of pegylation results in an increased in vivo half-life. However, it will be appreciated by persons skilled in the art that the pegylation process will need to be optimised for a particular protein on an individual basis.

PEG may be coupled at naturally occurring disulphide bonds as described in WO 2005/007197. Disulfide bonds can be stabilised through the addition of a chemical bridge which does not compromise the tertiary structure of the protein. This allows the conjugating thiol selectivity of the two sulphurs comprising a disulfide bond to be utilised to create a bridge for the site-specific attachment of PEG. Thereby, the need to engineer residues into a peptide for attachment of to target molecules is circumvented.

A variety of alternative block copolymers may also be covalently conjugated as described in WO 2003/059973. Therapeutic polymeric conjugates can exhibit improved thermal properties, crystallisation, adhesion, swelling, coating, pH dependent conformation and biodistribution. Furthermore, they can achieve prolonged circulation, release of the bioactive in the proteolytic and acidic environment of the secondary lysosome after cellular uptake of the conjugate by pinocytosis and more favourable physicochemical properties due to the characteristics of large molecules (e.g. increased drug solubility in biological fluids), block copolymers, comprising hydrophilic and hydrophobic blocks, form polymeric micelles in solution. Upon micelle disassociation, the individual block copolymer molecules are safely excreted.

Chemical derivatives of one or more amino acids may also be achieved by reaction with a functional side group. Such derivatised molecules include, for example, those molecules in which free amino groups have been derivatised to form amine hydrochlorides, p-toluene sulphonyl groups, carboxybenzoxy groups, t-butyloxycarbonyl groups, chloroacetyl groups or formyl groups. Free carboxyl groups may be derivatised to form salts, methyl and ethyl esters or other types of esters and hydrazides. Free hydroxyl groups may be derivatised to form O-acyl or O-alkyl derivatives. Also included as chemical derivatives are those peptides which contain naturally occurring amino acid derivatives of the twenty standard amino acids. For example: 4-hydroxyproline may be substituted for proline; 5-hydroxylysine may be substituted for lysine; 3-methylhistidine may be substituted for histidine; homoserine may be substituted for serine and ornithine for lysine. Derivatives also include peptides containing one or more additions or deletions as long as the requisite activity is maintained. Other included modifications are amidation, amino terminal acylation (e.g. acetylation or thioglycolic acid amidation), terminal carboxylamidation (e.g. with ammonia or methylamine), and the like terminal modifications.

It will be further appreciated by persons skilled in the art that peptidomimetic compounds may also be useful. Thus, by 'polypeptide' we include peptidomimetic compounds which have an anti-inflammatory activity. The term 'peptidomimetic' refers to a compound that mimics the conformation and desirable features of a particular peptide as a therapeutic agent.

For example, the polypeptides of the invention include not only molecules in which amino acid residues are joined by peptide (—CO—NH—) linkages but also molecules in which the peptide bond is reversed. Such retro-inverso peptidomimetics may be made using methods known in the art, for example such as those described in Meziere et al. (1997) J.

*Immunol* 159, 3230-3237, which is incorporated herein by reference. This approach involves making pseudopeptides containing changes involving the backbone, and not the orientation of side chains. Retro-inverse peptides, which contain NH—CO bonds instead of CO—NH peptide bonds, are much more resistant to proteolysis. Alternatively, the polypeptide of the invention may be a peptidomimetic compound wherein one or more of the amino acid residues are linked by a -y($CH_2NH$)— bond in place of the conventional amide linkage.

In a further alternative, the peptide bond may be dispensed with altogether provided that an appropriate linker moiety which retains the spacing between the carbon atoms of the amino acid residues is used; it may be advantageous for the linker moiety to have substantially the same charge distribution and substantially the same planarity as a peptide bond.

It will be appreciated that the polypeptide may conveniently be blocked at its N- or C-terminal region so as to help reduce susceptibility to exoproteolytic digestion.

A variety of uncoded or modified amino acids such as D-amino acids and N-methyl amino acids have also been used to modify mammalian peptides. In addition, a presumed bioactive conformation may be stabilised by a covalent modification, such as cyclisation or by incorporation of lactam or other types of bridges, for example see Veber at al., 1978, *Proc. Natl. Acad. Sci. USA* 75:2636 and Thursell et al., 1983, *Biochem. Biophys. Res. Comm.* 111:166, which are incorporated herein by reference.

A common theme among many of the synthetic strategies has been the introduction of some cyclic moiety into a peptide-based framework. The cyclic moiety restricts the conformational space of the peptide structure and this frequently results in an increased specificity of the peptide for a particular biological receptor. An added advantage of this strategy is that the introduction of a cyclic moiety into a peptide may also result in the peptide having a diminished sensitivity to cellular peptidases.

Thus, exemplary polypeptides of the invention comprise terminal cysteine amino acids. Such a polypeptide may exist in a heterodetic cyclic form by disulphide bond formation of the mercaptide groups in the terminal cysteine amino acids or in a homodetic form by amide peptide bond formation between the terminal amino acids. As indicated above, cyclising small peptides through disulphide or amide bonds between the N- and C-terminal region cysteines may circumvent problems of specificity and half-life sometime observed with linear peptides, by decreasing proteolysis and also increasing the rigidity of the structure, which may yield higher specificity compounds. Polypeptides cyclised by disulphide bonds have free amino and carboxy-termini which still may be susceptible to proteolytic degradation, while peptides cyclised by formation of an amide bond between the N-terminal amine and C-terminal carboxyl and hence no longer contain free amino or carboxy termini. Thus, the peptides of the present invention can be linked either by a C—N linkage or a disulphide linkage.

The present invention is not limited in any way by the method of cyclisation of peptides, but encompasses peptides whose cyclic structure may be achieved by any suitable method of synthesis. Thus, heterodetic linkages may include, but are not limited to formation via disulphide, alkylene or sulphide bridges. Methods of synthesis of cyclic homodetic peptides and cyclic heterodetic peptides, including disulphide, sulphide and alkylene bridges, are disclosed in U.S. Pat. No. 5,643,872, which is incorporated herein by reference. Other examples of cyclisation methods includes cyclization through click chemistry, epoxides, aldehyde-amine reactions, as well as and the methods disclosed in U.S. Pat. No. 6,008,058, which is incorporated herein by reference.

A further approach to the synthesis of cyclic stabilised peptidomimetic compounds is ring-closing metathesis (RCM). This method involves steps of synthesising a peptide precursor and contacting it with an RCM catalyst to yield a conformationally restricted peptide. Suitable peptide precursors may contain two or more unsaturated C—C bonds. The method may be carried out using solid-phase-peptide-synthesis techniques. In this embodiment, the precursor, which is anchored to a solid support, is contacted with a RCM catalyst and the product is then cleaved from the solid support to yield a conformationally restricted peptide.

Another approach, disclosed by D. H. Rich in *Protease Inhibitors*, Barrett and Selveson, eds., Elsevier (1986), which is incorporated herein by reference, has been to design peptide mimics through the application of the transition state analogue concept in enzyme inhibitor design. For example, it is known that the secondary alcohol of staline mimics the tetrahedral transition state of the scissile amide bond of the pepsin substrate.

In summary, terminal modifications are useful, as is well known, to reduce susceptibility by proteinase digestion and therefore to prolong the half-life of the peptides in solutions, particularly in biological fluids where proteases may be present. Polypeptide cyclisation is also a useful modification because of the stable structures formed by cyclisation and in view of the biological activities observed for cyclic peptides.

Thus, in one embodiment the polypeptide of the first aspect of the invention is linear. However, in an alternative embodiment, the polypeptide is cyclic.

It will be appreciated by persons skilled in the art that the polypeptides of the invention may be of various lengths. Typically, however, the polypeptide is between 10 and 200 amino acids in length, for example between 10 and 150, 15 and 100, 15 and 50, 15 and 30, 17 and 30, or 17 and 28 amino acids in length. For example, the polypeptide may be at least 20 amino acids in length.

As stated at the outset, anti-inflammatory activity is a feature common to the polypeptides of the invention. In one embodiment, the polypeptides are capable of inhibiting the release of one or more pro-inflammatory cytokines from human monocyte-derived macrophages, such as monocyte-derived macrophages, including macrophage inhibitory factor, TNF-alpha, HMGB1, C5a, IL-17, IL-8, MCP-1, IFN-gamma, Il-6, IL-1b, IL-12. Antiinflammatory IL-10 may be unaffected or transiently increased.

Other markers may also be affected: These include tissue factor on monocytes and endothelial cells, procalcitonin, CRP, reactive oxygen species, bradykinin, nitric oxide, PGE1, platelet activating factor, arachidonic acid metabolites, MAP kinase activation.

In particular, the polypeptide may exhibit anti-inflammatory activity in one or more of the following models:
 (i) in vitro macrophage models using LPS, LTA, zymosan, flagellin, dust mites, viral or bacterial DNA or RNA, or peptidoglycan as stimulants;
 (ii) in vivo mouse models of endotoxin shock; and/or
 (iii) in vivo infection models, either in combination with antimicrobial therapy, or given alone.

In a further embodiment of the invention, the polypeptide exhibits anticoagulant activity.

By "anti-coagulant activity" we mean an ability to reduce or prevent coagulation (i.e. the clotting of blood) or an associated signal or effect. Such activity may be determined by methods well known in the art, for example using the activated partial thromboplastin time (aPTT) test, prothrombin time (PT) test or the thrombin clotting time (TCT) test. Furthermore, specific measurements of prekallikrein activation or the activity of Factor X and other coagulation factors may be performed. It will be appreciated by skilled persons that the polypeptide may inhibit the extrinsic coagulation pathway and/or the intrinsic coagulation pathway. However, in a preferred embodiment, the polypeptide inhibits (at least in part) the intrinsic coagulation pathway.

In a still further embodiment of the invention, the polypeptide exhibits Toll-like receptor (TLR) blocking activity. Such receptor blocking activity can be measured using methods well known in the art, for example by analysis of suitable down-stream effectors, such as iNOS, nuclear factor kappa B and cytokines.

By virtue of possessing an anti-inflammatory activity, the polypeptides of the first aspect of the invention are intended for use in the treatment or prevention of inflammation.

By "treatment or prevention of inflammation" we mean that the polypeptide of the invention is capable of preventing or inhibiting (at least in part) one or more symptom, signal or effect constituting or associated with inflammation.

It will be appreciated by persons skilled in the art that inhibition of inflammation may be in whole or in part. In a preferred embodiment, the polypeptide is capable of inhibiting one or more markers of inflammation by 20% or more compared to cells or individuals which have not been exposed to the polypeptide, for example by at least 30%, 40%, 50%, 60%, 70%, 80%, 90% or more.

Advantageously, the polypeptides of the invention are capable of treating or preventing inflammation selectively.

By 'selectively' we mean that the polypeptide inhibits or prevents inflammation to a greater extent than it modulates other biological functions. Preferably, the polypeptide or fragment, variant, fusion or derivative thereof inhibits or prevents inflammation only.

However, in a further embodiment, the polypeptide also (or alternatively) inhibits or prevents coagulation of the blood. As above, it will be appreciated by persons skilled in the art that inhibition of coagulation may be in whole or in part. In a preferred embodiment, the polypeptide is capable of inhibiting one or more measures and or markers of coagulation by 20% or more compared to cells or individuals which have not been exposed to the polypeptide, for example by at least 30%, 40%, 50%, 60%, 70%, 80%, 90% or more.

In one embodiment, the polypeptides are for use in the treatment or prevention of inflammation associated with (i.e. caused by or merely co-presenting with) an infection.

In preferred but non-limiting embodiments of the invention, the polypeptides are for use in the treatment or prevention of a disease, condition or indication selected from the following:

i) Acute systemic inflammatory disease, with or without an infective component, such as systemic inflammatory response syndrome (SIRS), ARDS, sepsis, severe sepsis, and septic shock. Other generalized or localized invasive infective and inflammatory disease, including erysipelas, meningitis, arthritis, toxic shock syndrome, diverticulitis, appendicitis, pancreatitis, cholecystitis, colitis, cellulitis, burn wound infections, pneumonia, urinary tract infections, postoperative infections, and peritonitis.

ii) Chronic inflammatory and or infective diseases, including cystic fibrosis, COPD and other pulmonary diseases, gastrointestinal disease including chronic skin and stomach ulcerations, other epithelial inflammatory and or infective disease such as atopic dermatitis, oral ulcerations (aphtous ulcers), genital ulcerations and inflammatory changes, parodontitis, eye inflammations including conjunctivitis and keratitis, external otitis, mediaotitis, genitourinary inflammations.

iii) Postoperative inflammation. Inflammatory and coagulative disorders including thrombosis, DIC, postoperative coagulation disorders, and coagulative disorders related to contact with foreign material, including extracorporeal circulation, and use of biomaterials. Furthermore, vasculitis related inflammatory disease, as well as allergy, including allergic rhinitis and asthma.

iv) Excessive contact activation and/or coagulation in relation to, but not limited to, stroke.

v) Excessive inflammation in combination with antimicrobial treatment. The antimicrobial agents used may be administred by various routes; intravenous (iv), intraarterial, intravitreal, subcutaneous (sc), intramuscular (im), intraperitoneal (ip), intravesical, intratechal, epidural, enteral (including oral, rectal, gastric, and other enteral routes), or topically, (including dermal, nasal application, application in the eye or ear, eg by drops, and pulmonary inhalation). Examples of agents are penicillins, cephalosporins, carbacephems, cephamycins, carbapenems, monobactams, aminoglycosides, glycopeptides, quinolones, tetracyclines, macrolides, and fluoroquinolones. Antiseptic agents include iodine, silver, copper, clorhexidine, polyhexanide and other biguanides, chitosan, acetic acid, and hydrogen peroxide.

For example, the polypeptides may be for use in the treatment or prevention of an acute inflammation, sepsis, acute respiratory distress syndrome (ARDS), chronic obstructive pulmonary disease (COPD), cystic fibrosis, wounds, asthma, allergic and other types of rhinitis, cutaneous and systemic vasculitis, thrombosis and/or disseminated intravascular coagulation (DIC).

In one embodiment, the polypeptide exhibits both anti-inflammatory and anti-coagulant activity and may be used in the concomitant treatment or prevention of inflammation and coagulation. Such polypeptides may be particularly suited to the treatment and prevention of conditions where the combined inhibition of both inflammatory and coagulant processes is desirable, such as sepsis, chronic obstructive pulmonary disorder (COPD), thrombosis, DIC and acute respiratory distress syndrome (ARDS). Furthermore, other diseases associated with excessive inflammation and coagulation changes may benefit from treatment by the to polypeptides, such as cystic fibrosis, asthma, allergic and other types of rhinitis, cutaneous and systemic vasculitis.

In a further embodiment, the polypeptides of the invention are for use in combination with one or more additional therapeutic agent. For example, the polypeptides of the invention may be administered in combination with antibiotic agents, anti-inflammatory agents, immunosuppressive agents and/or antiseptic agents, as well as vasoactive agents and/or receptor-blockers or receptor agonists. The antimicrobial agents used may be applied iv, sc, im, intratechal, per os, or topically. Examples of agents are penicillins, cephalosporins, carbacephems, cephamycins, carbapenems, monobactams, aminoglycosides, glycopeptides, quinolones, tetracyclines, macrolides, and fluoroquinolones. Antiseptic agents include iodine, silver, copper, clorhexidine, polyhexanide and other biguanides, chitosan, acetic acid, and hydrogen peroxide. For example, the peptides of the invention may serve as adjuvants to antiseptic treatments, for example silver/PHMB treatment of wounds to quench LPS effects.

Thus, the peptides of the invention may serve as adjuvants (for blocking inflammation) to complement antibiotic, antiseptic and/or antifungal treatments of internal and external infections (such as erysipelas, lung infections including fungal infections, sepsis, COPD, wounds, and other epithelial infections). Likewise, the peptides of the invention may serve as adjuvants to antiseptic treatments, for example silver/PHMB treatment of wounds to quench LPS effects.

In one embodiment, the polypeptides of the invention are for use in combination with a steroid, for example a glucocorticoid (such as dexamethasone).

A second, related aspect of the invention provides an isolated polypeptide comprising or consisting of an amino acid sequence derived from a naturally occurring protein which modulates blood coagulation, namely heparin cofactor II, or a fragment, variant, fusion or derivative thereof, or a fusion of said fragment, variant or derivative thereof, which polypeptide exhibits an anti-inflammatory and/or anti-microbial and/or anti-coagulant activity, with the proviso that the polypeptide is not a naturally occurring protein (e.g. holoprotein).

By "naturally occurring protein" in this context we mean that the polypeptide is synthesized de novo. However, fragments of such naturally occurring holoproteins generated in vivo are not excluded.

It will be appreciated by persons skilled in the art that terms such as fragment, variant, fusion or derivative should be construed as discussed above in relation to the first aspect of the invention.

In one embodiment, the polypeptide comprises or consists of an amino acid sequence selected from the group consisting of SEQ ID NOS: 1 to 3, or a fragment, variant, fusion or derivative of said sequence, or a fusion of said fragment, variant or derivative thereof. For example, the polypeptide may comprise or consist of an amino acid sequence selected from the group consisting of SEQ ID NOS: 1 to 3.

It will be appreciated by persons skilled in the art that the optional features discussed above in relation to the polypeptides of the first aspect of the invention are also of relevance to the related polypeptides of the second aspect of the invention.

For example, in one preferred embodiment the polypeptide is capable of inhibiting the release of one or more pro-inflammatory cytokines from human monocyte-derived macrophages (such as IL-6, IFN-gamma, TNF-alpha, IL-12, IL-1 and/or IL-18).

In another preferred embodiment, the polypeptide exhibits anticoagulant activity.

The present invention also includes pharmaceutically acceptable acid or base addition salts of the above described polypeptides. The acids which are used to prepare the pharmaceutically acceptable acid addition salts of the aforementioned base compounds useful in this invention are those which form non-toxic acid addition salts, i.e. salts containing pharmacologically acceptable anions, such as the hydrochloride, hydrobromide, hydroiodide, nitrate, sulphate, bisulphate, phosphate, acid phosphate, acetate, lactate, citrate, acid citrate, tartrate, bitartrate, succinate, maleate, fumarate, gluconate, saccharate, benzoate, methanesulphonate, ethanesulphonate, benzenesulphonate, p-toluenesulphonate and pamoate [i.e. 1,1'-methylene-bis-(2-hydroxy-3 naphthoate)] salts, among others.

Pharmaceutically acceptable base addition salts may also be used to produce pharmaceutically acceptable salt forms of the polypeptides. The chemical bases that may be used as reagents to prepare pharmaceutically acceptable base salts of the present compounds that are acidic in nature are those that form non-toxic base salts with such compounds. Such non-toxic base salts include, but are not limited to those derived from such pharmacologically acceptable cations such as alkali metal cations (e.g. potassium and sodium) and alkaline earth metal cations (e.g. calcium and magnesium), ammonium or water-soluble amine addition salts such as N-methylglucamine-(meglumine), and the lower alkanolammonium and other base salts of pharmaceutically acceptable organic amines, among others.

It will be appreciated that the polypeptides of the invention may be lyophilised for storage and reconstituted in a suitable carrier prior to use, e.g. through freeze drying, spray drying, spray cooling, or through use of particle formation (precipitation) from supercritical carbon dioxide. Any suitable lyophilisation method (e.g. freeze-drying, spray drying, cake drying) and/or reconstitution techniques can be employed. It will be appreciated by those skilled in the art that lyophilisation and reconstitution can lead to varying degrees of activity loss and that use levels may have to be adjusted upward to compensate. Preferably, the lyophilised (freeze dried) polypeptide loses no more than about 1% of its activity (prior to lyophilisation) when rehydrated, or no more than about 5%, 10%, 20%, 25%, 30%, 35%, 40%, 45%, or no more than about 50% of its activity (prior to lyophilisation) when rehydrated.

Methods for the production of polypeptides of the invention are well known in the art.

Conveniently, the polypeptide is or comprises a recombinant polypeptide. Suitable methods for the production of such recombinant polypeptides are well known in the art, such as expression in prokaryotic or eukaryotic hosts cells (for example, see Sambrook & Russell, 2000, *Molecular Cloning, A Laboratory Manual*, Third Edition, Cold Spring Harbor, N.Y., the relevant disclosures in which document are hereby incorporated by reference).

Polypeptides of the invention can also be produced using a commercially available in vitro translation system, such as rabbit reticulocyte lysate or wheatgerm lysate (available from Promega). Preferably, the translation system is rabbit reticulocyte lysate. Conveniently, the translation system may be coupled to a transcription system, such as the TNT transcription-translation system (Promega). This system has the advantage of producing suitable mRNA transcript from an encoding DNA polynucleotide in the same reaction as the translation.

It will be appreciated by persons skilled in the art that polypeptides of the invention may alternatively be synthesised artificially, for example using well known liquid-phase or solid phase synthesis techniques (such as t-Boc or Fmoc solid-phase peptide synthesis).

Thus, included within the scope of the present invention are the following:

(a) a third aspect of the invention provides an isolated nucleic acid molecule which encodes a polypeptide according to the second aspect of the invention;

(b) a fourth aspect of the invention provides a vector (such as an expression vector) comprising a nucleic acid molecule according to the third aspect of the invention;

(c) a fifth aspect of the invention provides a host cell comprising a nucleic acid molecule according to the third aspect of the invention or a vector according to the fourth aspect of the invention; and (d) a sixth aspect of the invention provides a method of making a polypeptide according to the second aspect of the invention comprising culturing a population of host cells according to the fifth aspect of the invention under conditions in which said polypeptide is expressed, and isolating the polypeptide therefrom.

A seventh aspect of the invention provides a pharmaceutical composition comprising a polypeptide according to the first aspect of the invention together with a pharmaceutically acceptable excipient, diluent or carrier.

As used herein, 'pharmaceutical composition' means a therapeutically effective formulation for use in the treatment or prevention of disorders and conditions associated with inflammation.

As used herein, 'pharmaceutical composition' means a therapeutically effective formulation for use in the treatment or prevention of disorders and conditions associated with inflammation.

Additional compounds may also be included in the pharmaceutical compositions, such as other peptides, low molecular weight immunomodulating agents, receptor agonists and antagonists, and antimicrobial agents. Other examples include chelating agents such as EDTA, citrate, EGTA or glutathione.

The pharmaceutical compositions may be prepared in a manner known in the art that is sufficiently storage stable and suitable for administration to humans and animals. The pharmaceutical compositions may be lyophilised, e.g. through freeze drying, spray drying, spray cooling, or through use of particle formation from supercritical particle formation.

By "pharmaceutically acceptable" we mean a non-toxic material that does not decrease the effectiveness of the biological activity of the active ingredients, i.e. the anti-inflammatory polypeptide(s). Such pharmaceutically acceptable buffers, carriers or excipients are well-known in the art (see Remington's Pharmaceutical Sciences, 18th edition, A. R Gennaro, Ed., Mack Publishing Company (1990) and handbook of Pharmaceutical Excipients, 3rd edition, A. Kibbe, Ed., Pharmaceutical Press (2000).

The term "buffer" is intended to mean an aqueous solution containing an acid-base mixture with the purpose of stabilising pH. Examples of buffers are Trizma, Bicine, Tricine, MOPS, MOPSO, MOBS, Tris, Hepes, HEPBS, MES, phosphate, carbonate, acetate, citrate, glycolate, lactate, borate, ACES, ADA, tartrate, AMP, AMPD, AMPSO, BES, CABS, cacodylate, CHES, DIPSO, EPPS, ethanolamine, glycine, HEPPSO, imidazole, imidazolelactic acid, PIPES, SSC, SSPE, POPSO, TAPS, TABS, TAPSO and TES.

The term "diluent" is intended to mean an aqueous or non-aqueous solution with the purpose of diluting the peptide in the pharmaceutical preparation. The diluent may be one or more of saline, water, polyethylene glycol, propylene glycol, ethanol or oils (such as safflower oil, corn oil, peanut oil, cottonseed oil or sesame oil).

The term "adjuvant" is intended to mean any compound added to the formulation to increase the biological effect of the peptide. The adjuvant may be one or more of colloidal silver, or zinc, copper or silver salts with different anions, for example, but not limited to fluoride, chloride, bromide, iodide, tiocyanate, sulfite, hydroxide, phosphate, carbonate, lactate, glycolate, citrate, borate, tartrate, and acetates of different acyl composition. The adjuvant may also be cationic polymers such as PHMB, cationic cellulose ethers, cationic cellulose esters, deacetylated hyaluronic acid, chitosan, cationic dendrimers, cationic synthetic polymers such as poly (vinyl imidazole), and cationic polypeptides such as polyhistidine, polylysine, polyarginine, and peptides containing these amino acids.

The excipient may be one or more of carbohydrates, polymers, lipids and minerals. Examples of carbohydrates include lactose, sucrose, mannitol, and cyclodextrines, which are added to the composition, e.g., for facilitating lyophilisation. Examples of polymers are starch, cellulose ethers, cellulose, carboxymethylcellulose, hydroxypropylmethyl cellulose, hydroxyethyl cellulose, ethylhydroxyethyl cellulose, ethyl cellulose, methyl cellulose, propyl cellulose, alginates, carageenans, hyaluronic acid and derivatives thereof, polyacrylic acid, polysulphonate, polyethylenglycol/polyethylene oxide, polyethyleneoxide/polypropylene oxide copolymers, polyvinylalcohol/polyvinylacetate of different degree of hydrolysis, polylactic acid), poly(glycholic acid) or copolymers thereof with various composition, and polyvinylpyrrolidone, all of different molecular weight, which are added to the composition, e.g. for viscosity control, for achieving bioadhesion, or for protecting the active ingredient (applies to A-C as well) from chemical and proteolytic degradation. Examples of lipids are fatty acids, phospholipids, mono-, di-, and triglycerides, ceramides, sphingolipids and glycolipids, all of different acyl chain length and saturation, egg lecithin, soy lecithin, hydrogenated egg and soy lecithin, which are added to the composition for reasons similar to those for polymers. Examples of minerals are talc, magnesium oxide, zinc oxide and titanium oxide, which are added to the composition to obtain benefits such as reduction of liquid accumulation or advantageous pigment properties.

The pharmaceutical composition may also contain one or more mono- or di-sacharides such as xylitol, sorbitol, mannitol, lactitiol, isomalt, maltitol or xylosides, and/or monoacylglycerols, such as monolaurin. The characteristics of the carrier are dependent on the route of administration. One route of administration is topical administration. For example, for topical administrations, a preferred carrier is an emulsified cream comprising the active peptide, but other common carriers such as certain petrolatum/mineral-based and vegetable-based ointments can be used, as well as polymer gels, liquid crystalline phases and microemulsions.

It will be appreciated that the pharmaceutical compositions may comprise one or more polypeptides of the invention, for example one, two, three or four different peptides. By using a combination of different peptides the anti-inflammatory effect may be increased.

As discussed above, the polypeptide may be provided as a salt, for example an acid adduct with inorganic acids, such as hydrochloric acid, sulfuric acid, nitric acid, hydrobromic acid, phosphoric acid, perchloric acid, thiocyanic acid, boric acid etc. or with organic acid such as formic acid, acetic acid, haloacetic acid, propionic acid, glycolic acid, citric acid, tartaric acid, succinic acid, gluconic acid, lactic acid, malonic acid, fumaric acid, anthranilic acid, benzoic acid, cinnamic acid, p-toluenesulfonic acid, naphthalenesulfonic acid, sulfanilic acid etc. Inorganic salts such as monovalent sodium, potassium or divalent zinc, magnesium, copper calcium, all with a corresponding anion, may be added to improve the biological activity of the antimicrobial composition.

The pharmaceutical compositions of the invention may also be in the form of a liposome, in which the polypeptide is combined, in addition to other pharmaceutically acceptable carriers, with amphipathic agents such as lipids, which exist in aggregated forms as micelles, insoluble monolayers and liquid crystals. Suitable lipids for liposomal formulation include, without limitation, monoglycerides, diglycerides, sulfatides, lysolecithin, phospholipids, saponin, bile acids, and the like. Suitable lipids also include the lipids above modified by poly(ethylene glycol) in the polar headgroup for prolonging bloodstream circulation time. Preparation of such liposomal formulations is can be found in for example U.S. Pat. No. 4,235,871.

The pharmaceutical compositions of the invention may also be in the form of biodegradable microspheres. Aliphatic polyesters, such as poly(lactic acid) (PLA), poly(glycolic acid) (PGA), copolymers of PLA and PGA (PLGA) or poly (carprolactone) (PCL), and polyanhydrides have been widely used as biodegradable polymers in the production of microshperes. Preparations of such microspheres can be found in U.S. Pat. No. 5,851,451 and in EP 213 303.

The pharmaceutical compositions of the invention may also be formulated with micellar systems formed by surfactants and block copolymers, preferably those containing poly (ethylene oxide) moieties for prolonging bloodstream circulation time.

The pharmaceutical compositions of the invention may also be in the form of polymer gels, where polymers such as starch, cellulose ethers, cellulose, carboxymethylcellulose, hydroxypropylmethyl cellulose, hydroxyethyl cellulose, ethylhydroxyethyl cellulose, ethyl cellulose, methyl cellulose, propyl cellulose, alginates, chitosan, carageenans, hyaluronic acid and derivatives thereof, polyacrylic acid, polyvinyl imidazole, polysulphonate, polyethylenglycol/polyethylene oxide, polyethylene-oxide/polypropylene oxide copolymers, polyvinylalcohol/polyvinylacetate of different degree of hydrolysis, and polyvinylpyrrolidone are used for thickening of the solution containing the peptide. The polymers may also comprise gelatin or collagen.

Alternatively, the polypeptides of the invention may be dissolved in saline, water, polyethylene glycol, propylene glycol, ethanol or oils (such as safflower oil, corn oil, peanut oil, cottonseed oil or sesame oil), tragacanth gum, and/or various buffers.

The pharmaceutical composition may also include ions and a defined pH for potentiation of action of anti-inflammatory polypeptides.

The compositions of the invention may be subjected to conventional pharmaceutical operations such as sterilisation and/or may contain conventional adjuvants such as preservatives, stabilisers, wetting agents, emulsifiers, buffers, fillers, etc., e.g., as disclosed elsewhere herein.

It will be appreciated by persons skilled in the art that the pharmaceutical compositions of the invention may be administered locally or systemically. Routes of administration include topical, ocular, nasal, pulmonary, buccal, parenteral (intravenous, subcutaneous, and intramuscular), oral, vaginal and rectal. Also administration from implants is possible. Suitable preparation forms are, for example granules, powders, tablets, coated tablets, (micro) capsules, suppositories, syrups, emulsions, microemulsions, defined as optically isotropic thermodynamically stable systems consisting of water, oil and surfactant, liquid crystalline phases, defined as systems characterised by long-range order but short-range disorder (examples include lamellar, hexagonal and cubic phases, either water- or oil continuous), or their dispersed counterparts, gels, ointments, dispersions, suspensions, creams, aerosols, droplets or injectable solution in ampoule form and also preparations with protracted release of active compounds, in whose preparation excipients, diluents, adjuvants or carriers are customarily used as described above. The pharmaceutical composition may also be provided in bandages, plasters or in sutures or the like.

In preferred embodiments, the pharmaceutical composition is suitable for parenteral administration or topical administration.

In alternative preferred embodiments, the pharmaceutical composition is suitable for pulmonary administration or nasal administration.

For example, the pharmaceutical compositions of the invention can be administered intranasally or by inhalation and are conveniently delivered in the form of a dry powder inhaler or an aerosol spray presentation from a pressurised container, pump, spray or nebuliser with the use of a suitable propellant, e.g. dichlorodifluoromethane, trichlorofluoromethane, dichlorotetrafluoro-ethane, a hydrofluoroalkane such as 1,1,1,2-tetrafluoroethane (HFA 134A3 or 1,1,1,2,3,3,3-heptafluoropropane (HFA 227EA3), carbon dioxide or other suitable gas. In the case of a pressurised aerosol, the dosage unit may be determined by providing a valve to deliver a metered amount. The pressurised container, pump, spray or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a polypeptide of the invention and a suitable powder base such as lactose or starch.

Aerosol or dry powder formulations are preferably arranged so that each metered dose or 'puff' contains at least 0.1 mg of a polypeptide of the invention for delivery to the patient. It will be appreciated that the overall daily dose with an aerosol will vary from patient to patient, and may be administered in a single dose or, more usually, in divided doses throughout the day.

The pharmaceutical compositions will be administered to a patient in a pharmaceutically effective dose. By "pharmaceutically effective dose" is meant a dose that is sufficient to produce the desired effects in relation to the condition for which it is administered. The exact dose is dependent on the, activity of the compound, manner of administration, nature and severity of the disorder, age and body weight of the patient different doses may be needed. The administration of the dose can be carried out both by single administration in the form of an individual dose unit or else several smaller dose units and also by multiple administrations of subdivided doses at specific intervals.

The pharmaceutical compositions of the invention may be administered alone or in combination with other therapeutic agents, such as additional antibiotic, anti-inflammatory, immunosuppressive, vasoactive and/or antiseptic agents (such as anti-bacterial agents, anti-fungicides, anti-viral agents, and anti-parasitic agents). Examples of suitable antibiotic agents include penicillins, cephalosporins, carbacephems, cephamycins, carbapenems, monobactams, aminoglycosides, glycopeptides, quinolones, tetracyclines, macrolides, and fluoroquinolones. Antiseptic agents include iodine, silver, copper, clorhexidine, polyhexanide and other biguanides, chitosan, acetic acid, and hydrogen peroxide. Likewise, the pharmaceutical compositions may also contain additional anti-inflammatory drugs, such as steroids and macrolactam derivatives.

In one embodiment, the pharmaceutical compositions of the invention are administered in combination with a steroid, for example a glucocorticoid (such as dexamethasone).

It will be appreciated by persons skilled in the art that the additional therapeutic agents may be incorporated as part of the same pharmaceutical composition or may be administered separately.

In one embodiment of the seventh aspect of the invention, the pharmaceutical composition is associated with a device or material to be used in medicine (either externally or internally). By 'associated with' we include a device or material which is coated, impregnated, covalently bound to or otherwise admixed with a pharmaceutical composition of the invention (or polypeptide thereof).

For example, the composition may be coated to a surface of a device that comes into contact with the human body or component thereof (e.g. blood), such as a device used in by-pass surgery, extracorporeal circulation, wound care and/ or dialysis. Thus, the composition may be coated, painted, sprayed or otherwise applied to or admixed with a suture, prosthesis, implant, wound dressing, catheter, lens, skin graft, skin substitute, fibrin glue or bandage, etc. In so doing, the composition may impart improved anti-inflammatory and/or anti-coagulant properties to the device or material.

Preferably, the device or material is coated with the pharmaceutical composition of the invention (or the polypeptide component thereof). By 'coated' we mean that the pharmaceutical composition is applied to the surface of the device or material. Thus, the device or material may be painted or sprayed with a solution comprising a pharmaceutical composition of the invention (or polypeptide thereof). Alternatively, the device or material may be dipped in a reservoir of a solution comprising a polypeptide of the invention.

Advantageously, the device or material is impregnated with a pharmaceutical composition of the invention (or polypeptide thereof). By 'impregnated' we mean that the pharmaceutical composition is incorporated or otherwise mixed with the device or material such that it is distributed throughout.

For example, the device or material may be incubated overnight at 4° C. in a solution comprising a polypeptide of the invention. Alternatively, a pharmaceutical composition of the invention (or polypeptide thereof) may be immobilised on the device or material surface by evaporation or by incubation at room temperature.

In an alternative embodiment, a polypeptide of the invention is covalently linked to the device or material, e.g. at the external surface of the device or material. Thus, a covalent bond is formed between an appropriate functional group on the polypeptide and a functional group on the device or material. For example, methods for covalent bonding of polypeptides to polymer supports include covalent linking via a diazonium intermediate, by formation of peptide links, by alkylation of phenolic, amine and sulphydryl groups on the binding protein, by using a poly functional intermediate e.g. glutardialdehyde, and other miscellaneous methods e.g. using silylated glass or quartz where the reaction of di- and trialkoxysilanes permits derivatisation of the glass surface with many different functional groups. For details, see Enzyme immobilisation by Griffin, M., Hammonds, E. J. and Leach, C. K. (1993) In *Technological Applications of Biocatalysts* (BIOTOL SERIES), pp. 75-118, Butterworth-Heinemann. See also the review article entitled 'Biomaterials in Tissue Engineering' by Hubbell, J. A. (1995) *Science* 13:565-576.

In a preferred embodiment, the device or material comprise or consists of a polymer. The polymer may be selected from the group consisting of polyesters (e.g. polylactic acid, polyglycolic acid or poly lactic acid-glycolic acid copolymers of various composition), polyorthoesters, polyacetals, polyureas, polycarbonates, polyurethanes, polyamides) and polysaccharide materials (e.g. cross-linked alginates, hyaluronic acid, carageenans, gelatines, starch, cellulose derivatives).

Alternatively, or in addition, the device or material may comprise or consists of metals (e.g. titanium, stainless steel, gold, titanium), metal oxides (silicon oxide, titanium oxide) and/or ceramics (apatite, hydroxyapatite).

Such materials may be in the form of macroscopic solids/monoliths, as chemically or physicochemically cross-linked gels, as porous materials, or as particles.

Thus, the present invention additionally provides devices and materials to be used in medicine, to which have been applied a polypeptide of the invention or pharmaceutical composition comprising the same.

Such devices and materials may be made using methods well known in the art.

An eighth aspect of the invention provides a polypeptide according to the second aspect of the invention or a pharmaceutical composition according to the seventh aspect of the invention for use in medicine.

In preferred embodiments, the polypeptide according to the second aspect of the invention or the pharmaceutical composition according to the seventh aspect of the invention are for use:
(a) the treatment and/or prevention of acute and/or chronic inflammation;
(b) the treatment and/prevention of microbial infection (e.g. bacterial infection);
(c) the modulation of blood coagulation; and/or
(d) the treatment of wounds.

In preferred embodiments, the polypeptide according to the second aspect of the invention or the pharmaceutical composition according to the seventh aspect of the invention are for use in the treatment and/prevention of a disease, condition or indication selected from the following:

i) Acute systemic inflammatory disease, with or without an infective component, such as systemic inflammatory response syndrome (SIRS), ARDS, sepsis, severe sepsis, and septic shock. Other generalized or localized invasive infective and inflammatory disease, including erysipelas, meningitis, arthritis, toxic shock syndrome, diverticulitis, appendicitis, pancreatitis, cholecystitis, colitis, cellulitis, burn wound infections, pneumonia, urinary tract infections, postoperative infections, and peritonitis.

ii) Chronic inflammatory and or infective diseases, including cystic fibrosis, COPD and other pulmonary diseases, gastrointestinal disease including chronic skin and stomach ulcerations, other epithelial inflammatory and or infective disease such as atopic dermatitis, oral ulcerations (aphtous ulcers), genital ulcerations and inflammatory changes, parodontitis, eye inflammations including conjunctivitis and keratitis, external otitis, mediaotitis, genitourinary inflammations.

iii) Postoperative inflammation. Inflammatory and coagulative disorders including thrombosis, DIC, postoperative coagulation disorders, and coagulative disorders related to contact with foreign material, including extracorporeal circulation, and use of biomaterials. Furthermore, vasculitis related inflammatory disease, as well as allergy, including allergic rhinitis and asthma.

iv) Excessive contact activation and/or coagulation in relation to, but not limited to, stroke.

v) Excessive inflammation in combination with antimicrobial treatment. The antimicrobial agents used may be administred by various routes; intravenous (iv), intraarterial, intravitreal, subcutaneous (sc), intramuscular (im), intraperitoneal (ip), intravesical, intratechal, epidural, enteral (including oral, rectal, gastric, and other enteral routes), or topically, (including dermal, nasal application, application in the eye or ear, eg by drops, and pulmonary inhalation). Examples of agents are penicillins, cephalosporins, carbacephems, cephamycins, carbapenems, monobactams, aminoglycosides, glycopeptides, quinolones, tetracyclines, macrolides, and fluoroquinolones. Antiseptic agents include iodine, silver, copper, clorhexidine, polyhexanide and other biguanides, chitosan, acetic acid, and hydrogen peroxide.

For example, the polypeptides may be for use in the treatment or prevention of an acute inflammation, sepsis, acute respiratory distress syndrome (ARDS), chronic obstructive pulmonary disease (COPD), cystic fibrosis, wounds, asthma, allergic and other types of rhinitis, cutaneous and systemic vasculitis, thrombosis and/or disseminated intravascular coagulation (DIC).

For example, polypeptides comprising or consisting of an amino acid sequence of SEQ ID NO:1 or 2, or a fragment, variant, fusion or derivative thereof, or a fusion of said fragment, variant or derivative thereof, may be used for the treatment and/or prevention of acute and/or chronic inflammation.

In a further example, polypeptides comprising or consisting of an amino acid sequence of SEQ ID NO:3, or a fragment, variant, fusion or derivative thereof, or a fusion of said fragment, variant or derivative thereof, may be used for the treatment and/or prevention of microbial infection (e.g. bacterial infection).

A related ninth aspect of the invention provides the use of a polypeptide according to the second aspect of the invention or a pharmaceutical composition according to the seventh aspect of the invention in the preparation of a medicament for the treatment or prevention of inflammation and/or excessive coagulation (as described above).

A tenth aspect of the invention provides a method for treating or preventing inflammation and/or excessive coagulation in a patient, the method comprising administering to the patient a therapeutically-effective amount of a polypeptide according to the second aspect of the invention or a pharmaceutical composition according to the seventh aspect of the invention (as described above). In preferred but non-limiting embodiments, the method is for the treatment or prevention of an acute inflammation, sepsis, acute respiratory distress syndrome (ARDS), chronic obstructive pulmonary disease (COPD), cystic fibrosis, asthma, allergic and other types of rhinitis, cutaneous and systemic vasculitis, thrombosis and/or disseminated intravascular coagulation (DIC).

Persons skilled in the art will further appreciate that the uses and methods of the present invention have utility in both the medical and veterinary fields. Thus, the polypeptide medicaments may be used in the treatment of both human and non-human animals (such as horses, dogs and cats). Advantageously, however, the patient is human.

Preferred aspects of the invention are described in the following non-limiting examples, with reference to the following figures:

FIG. 1: NO-blocking effects of C-terminal peptides of TFPI.

RAW 264.7 macrophages were stimulated with 10 ng/ml E. coli LPS, and 10 µM of the peptides GGL27, LIK17 and TKR22 were added. NO was measured using Griess reagent.

Figure 2:
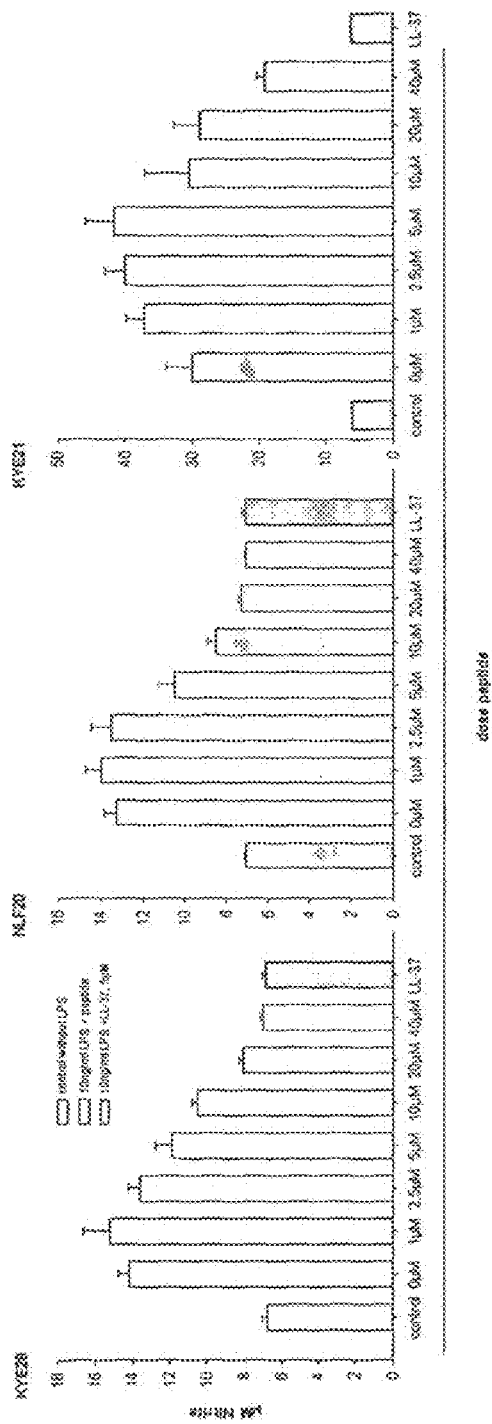

FIG. 2: NO-blocking effects of peptides of heparin cofactor II.

RAW macrophages were stimulated with 10 ng/ml E. coli LPS, and the peptides KYE28, NLF20, and KYE21, were added at the indicated doses. LL-37 is presented as positive control. NO was measured using Griess reagent.

Figure 3:
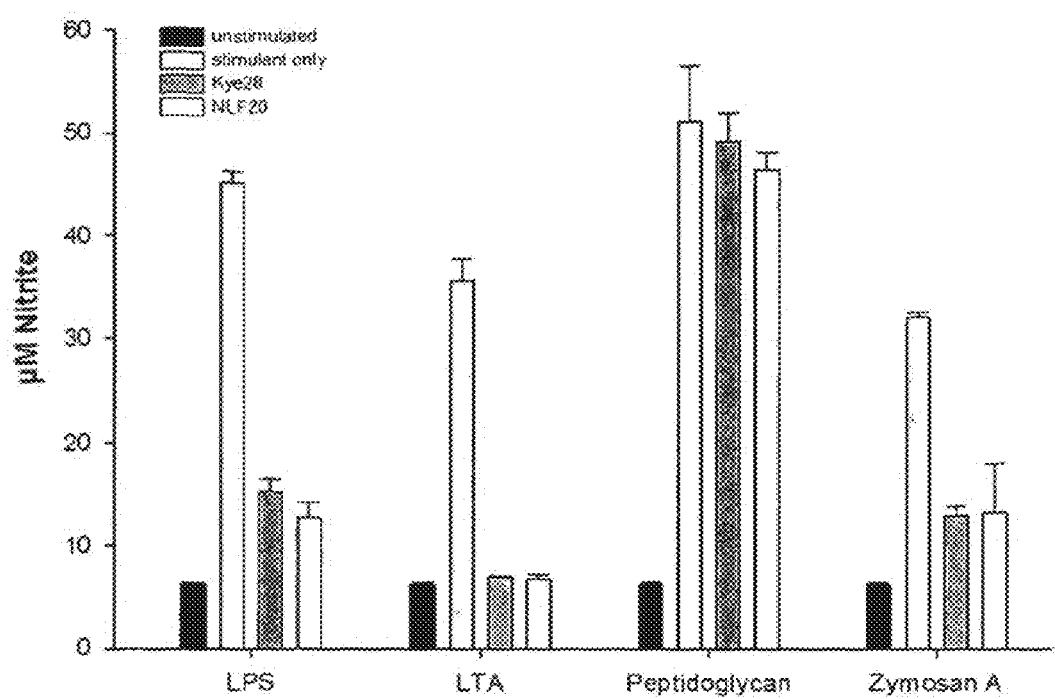

FIG. 3: Anti-inflammatory effects of peptides of heparin cofactor II.

KYE28, KYE21 and NLF20 blocks NO production of RAW264.7 macrophages stimulated with various microbial products. Cells were subjected to the indicated concentrations of E. coli LPS, lipoteichoic acid (LTA) and peptidoglycan (PGN) from S. aureus as well as zymosan A from Saccharomyces cerevisiae, NO production with or without 10 µM GKY25 was determined by using the Griess reagent.

Figure 4:
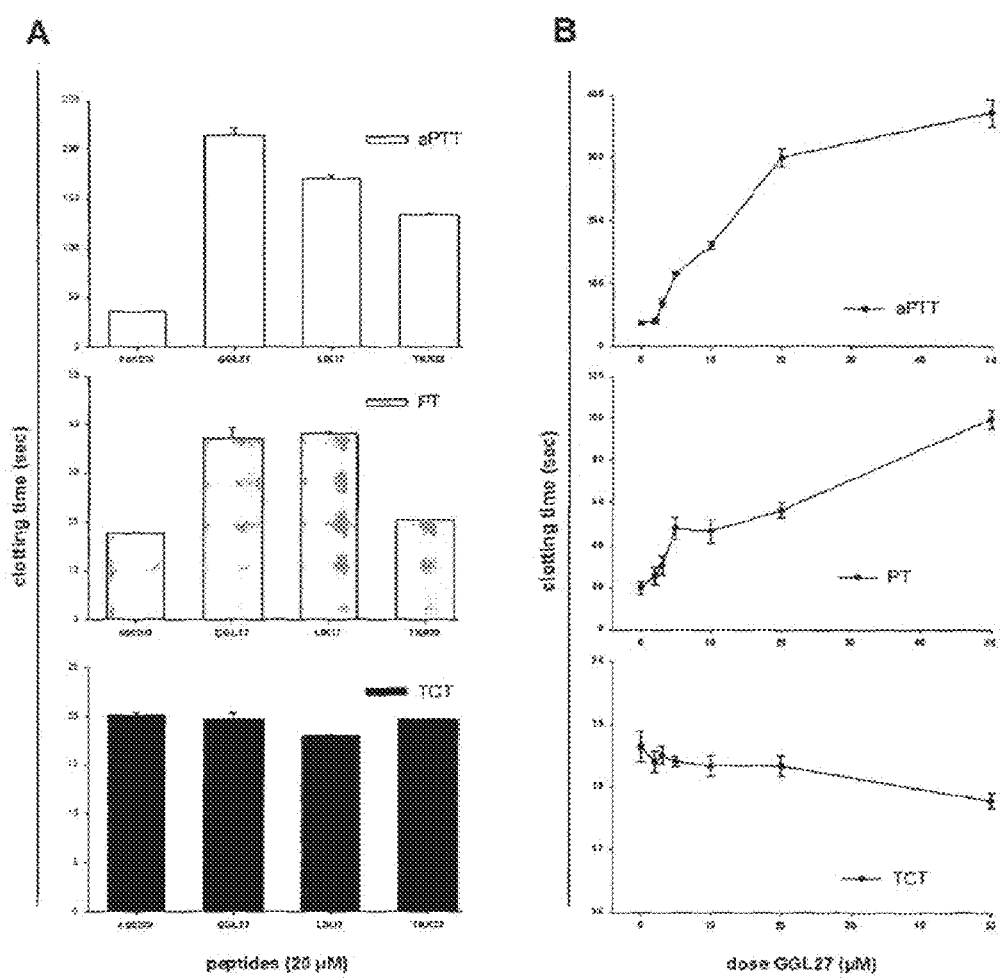

FIG. 4: C-terminal peptides of TFPI block coagulation.

(A) The C-terminal peptides of TFPI; GGL27, LIK17, as well as TKR22 impair the intrinsic pathway of coagulation in normal human plasma. This was determined by measuring the activated partial thromboplastin time (aPTT). GGL27 and LIK17 also affected prothrombin time (PT) monitoring the extrinsic pathway of coagulation. The thrombin clotting time (TCT), measuring thrombin induced fibrin network formation, were not significantly affected by the peptides (B) GGL-27 impairs coagulation in a dose dependent manner monitored by measuring the aPTT, PT and TCT in normal human plasma.

Figure 5:
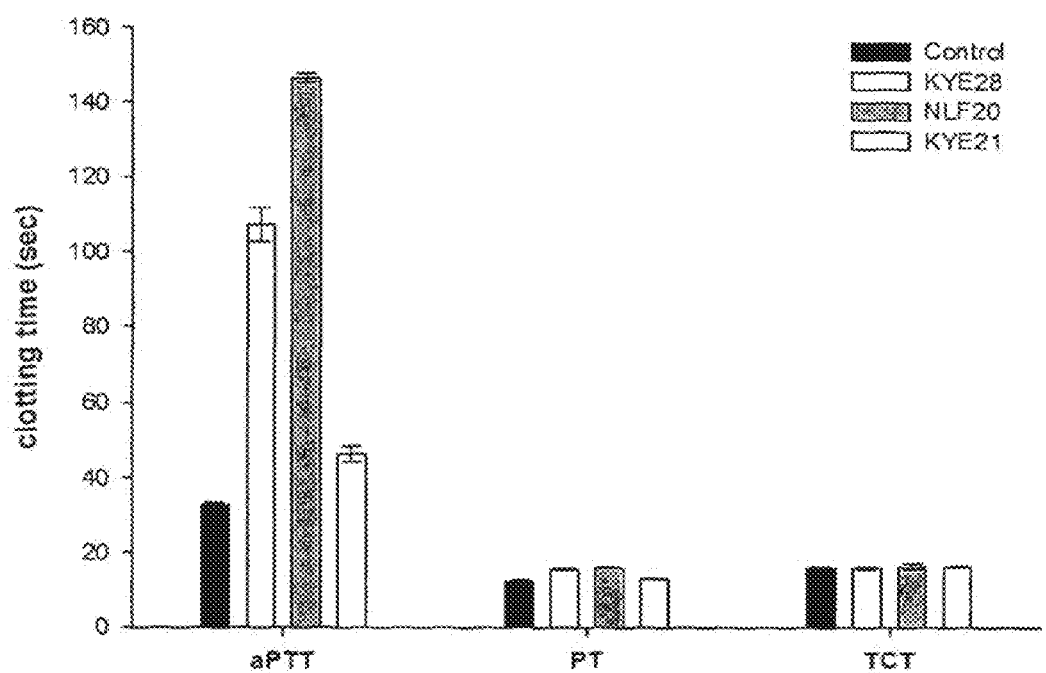

FIG. 5: Peptides of heparin-cofactor II block coagulation.

KYE28 and NLF20 impair the intrinsic pathway of coagulation in normal human plasma determined by measuring the activated partial thromboplastin time (aPTT). KYE21 shows only minor blocking of the aPTT. Other parts of the coagulation system, as judged by the prothrombin time (PT) monitoring the extrinsic pathway of coagulation, and the thrombin clotting time (TCT), measuring thrombin induced fibrin network formation, were not significantly affected.

Figure 6:
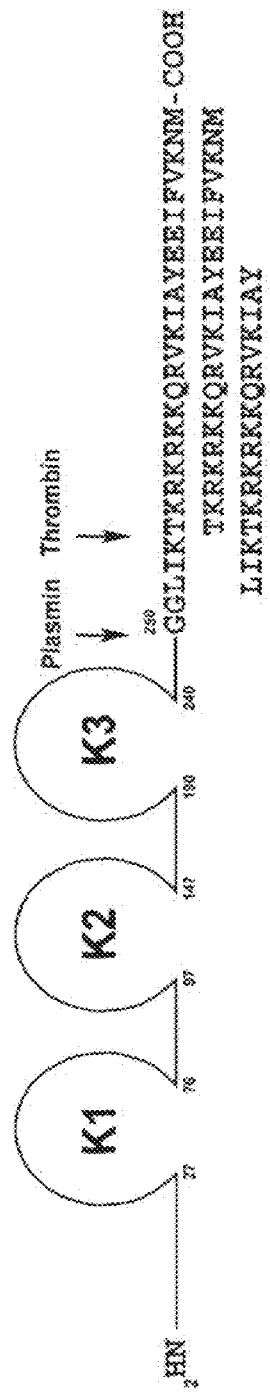

FIG. 6: Cartoon illustrating the structure of TFPI.

Cleavage points by enzymes are indicated. [SEQ ID NO:5, SEQ ID NO:6, AND SEQ IDS NO:7]

Figure 7:
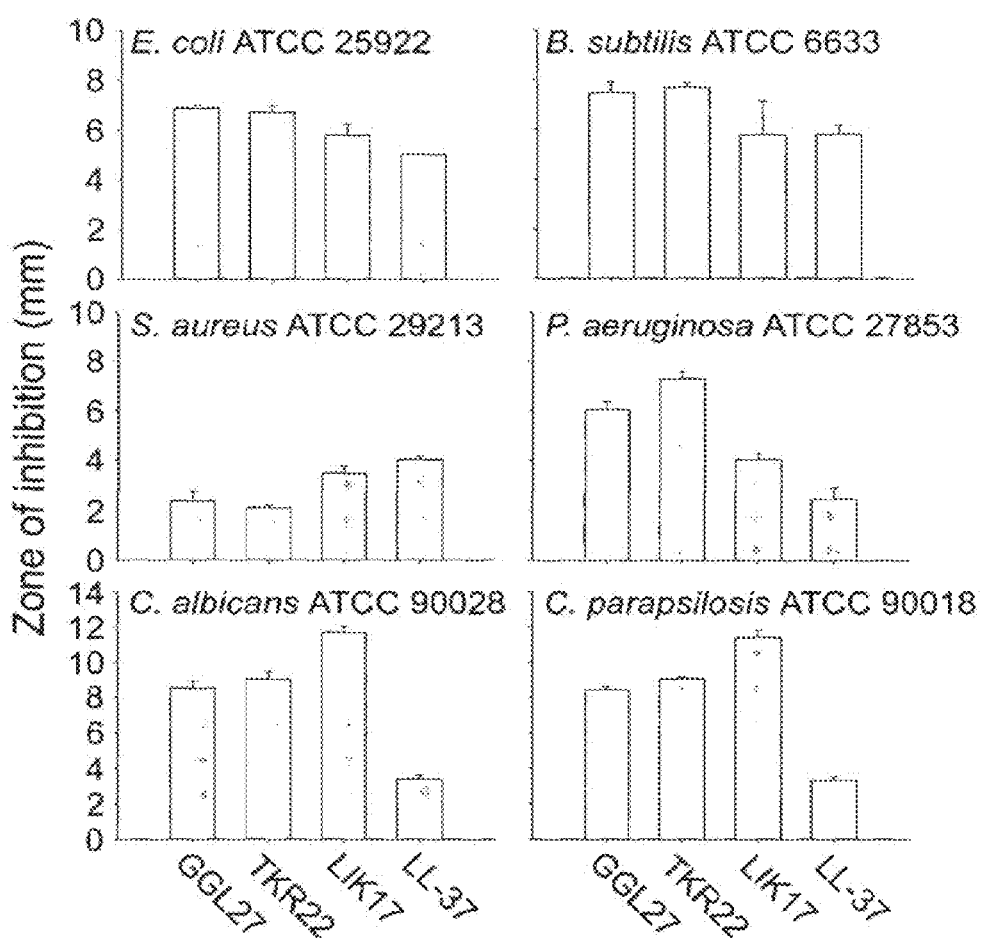

FIG. 7: Antimicrobial activities of TFPI-derived peptides.

Antimicrobial activity of selected peptides (at 100 µM in RDA) against the indicated microbes. For determination of antimicrobial activities, E. coli ATCC 25922, S. aureus ATCC 29213 isolates ($4\times10^6$ cfu) or C. parapsilosis ATCC 90018 ($1\times10^5$ cfu) was inoculated in 0.1% TSB agarose gel. Each 4 mm-diameter well was loaded with 6 µl of peptide. The zones of clearance correspond to the inhibitory effect of each peptide after incubation at 37° C. for 18-24 h (mean values are presented, n=3).

Figure 8:
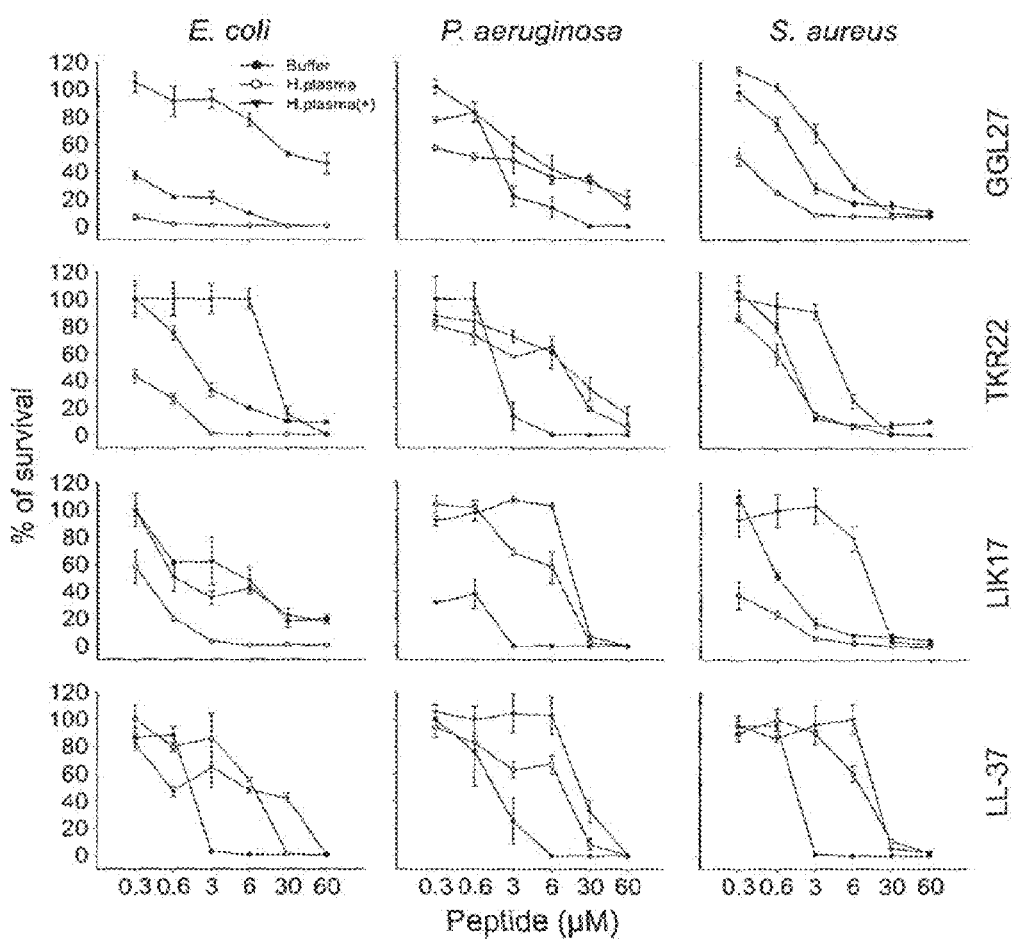

FIG. 8: Antibacterial effects of TFPI-derived peptides.

Effects of TFPI-derived peptides and LL-37 against E. coli in viable count assays. $2\times10^6$ cfu/ml of bacteria were incubated in 50 µl with peptides at the indicated concentrations in 10 mM Tris, pH 7.4 buffer (Tris), or in 0.15 m NaCl, 10 mM Tris, pH 7.4 containing normal or heat-inactivated 20% human plasma (n=3, SD is indicated).

Figure 9:
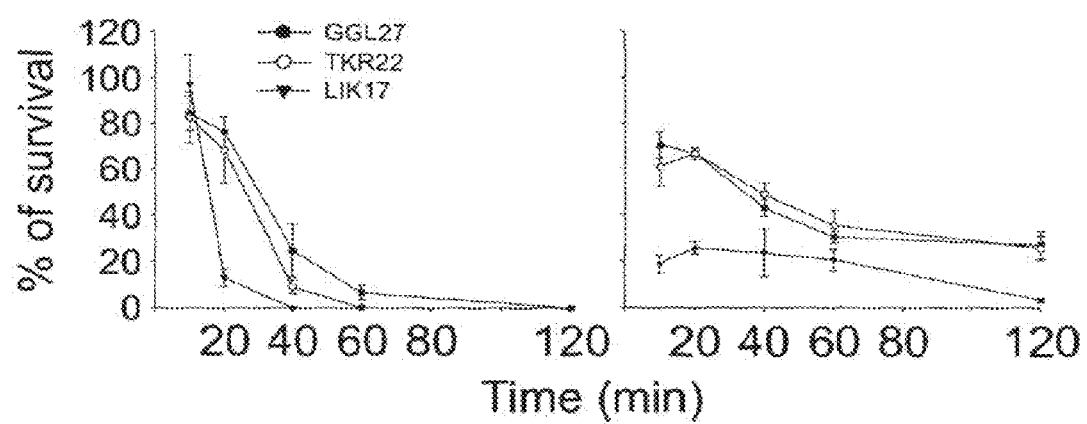

FIG. 9: Kinetic analysis.

The time-dependence of bacterial killing by TFPI-derived peptides (at 6 and 30 µM) in 0.15 m NaCl, 10 mM Tris, pH 7.4 containing 20% plasma was analyzed by viable count assays using E. coli.

Figure 10:
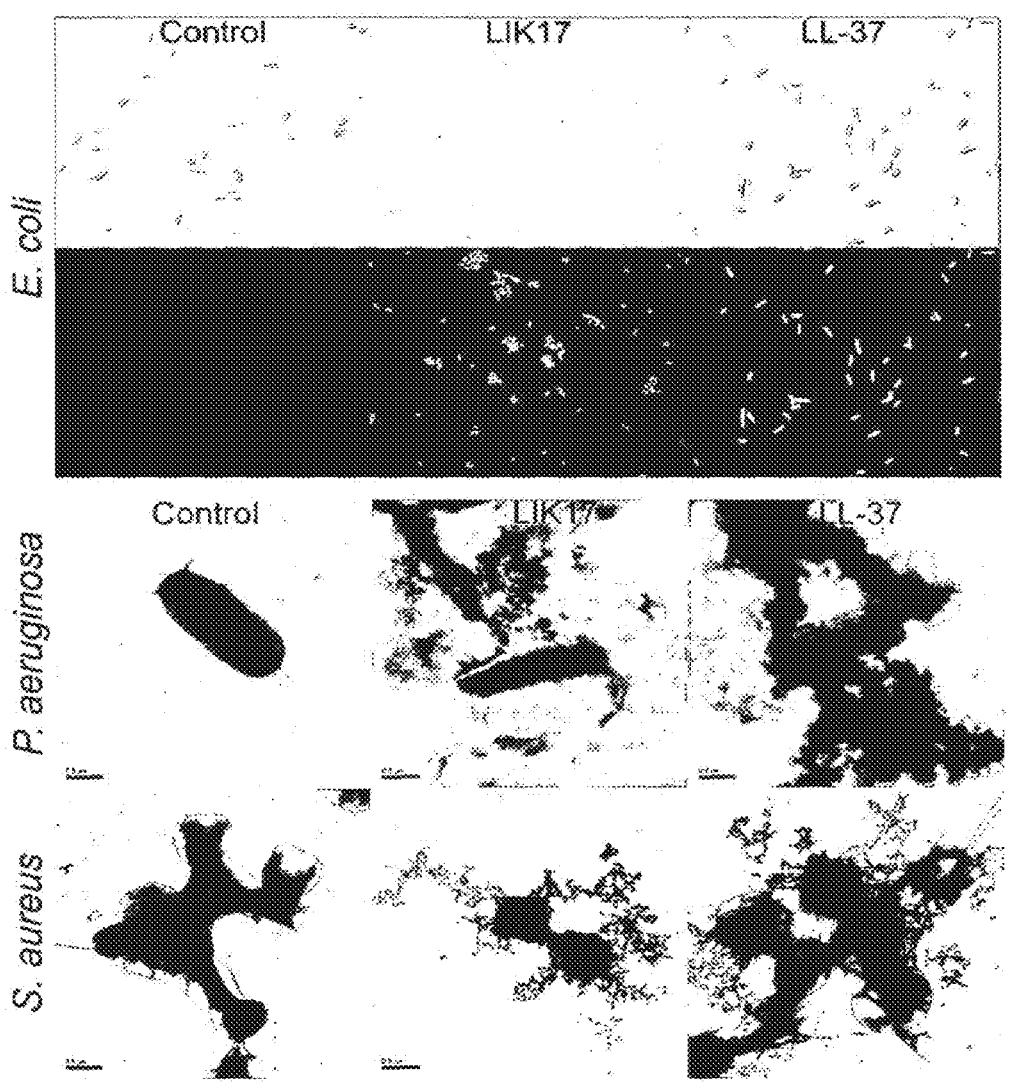

FIG. 10: Effects on bacterial membranes.

(A) Permeabilizing effects of peptides on P. aeruginosa and E. coli. (A) Bacteria were incubated with the indicated peptides and permeabilization was assessed using the impermeant probe FITC. (B) Electron microscopy analysis. P. aeruginosa and S. aureus bacteria was incubated for 2 h at 37° C. with 30 µM of GKY25 and LL-37 and analysed with electron microscopy. Scale bar represents 1 µm. Control; Buffer control.

Figure 11:
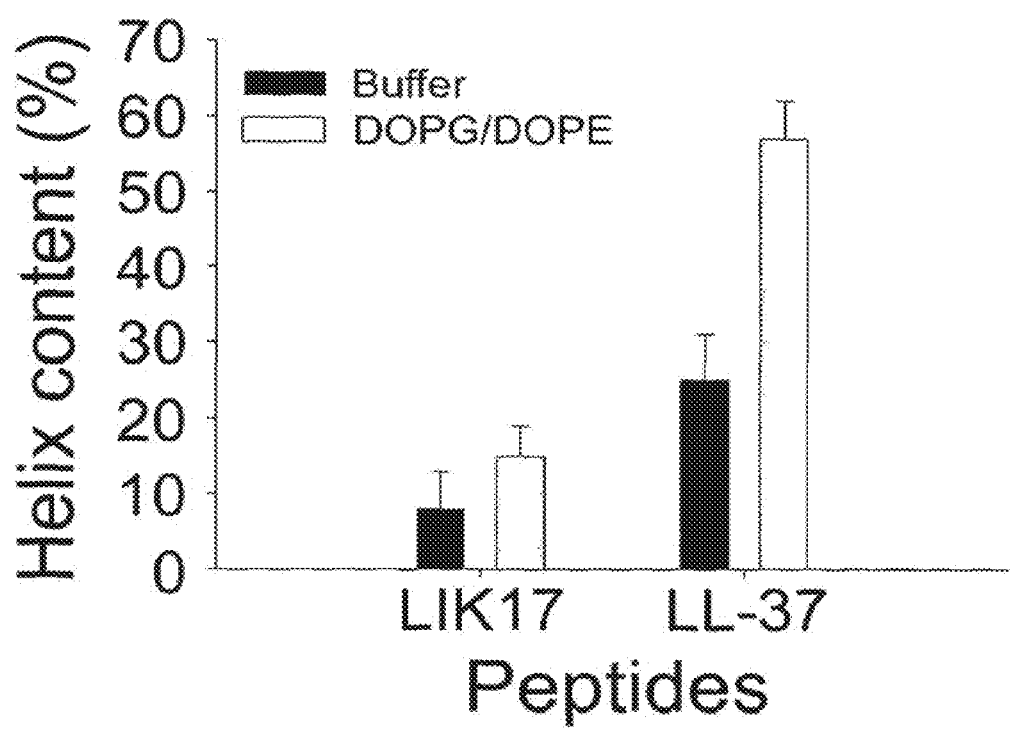

FIG. 11: Structure of TFPI peptide LIK17.

Helical content of the TFPI-derived C-terminal peptide in presence of negatively charged liposomes (DOPE/DOPG). LIK17 structure was largely unaffected by the addition of liposomes.

Figure 12:
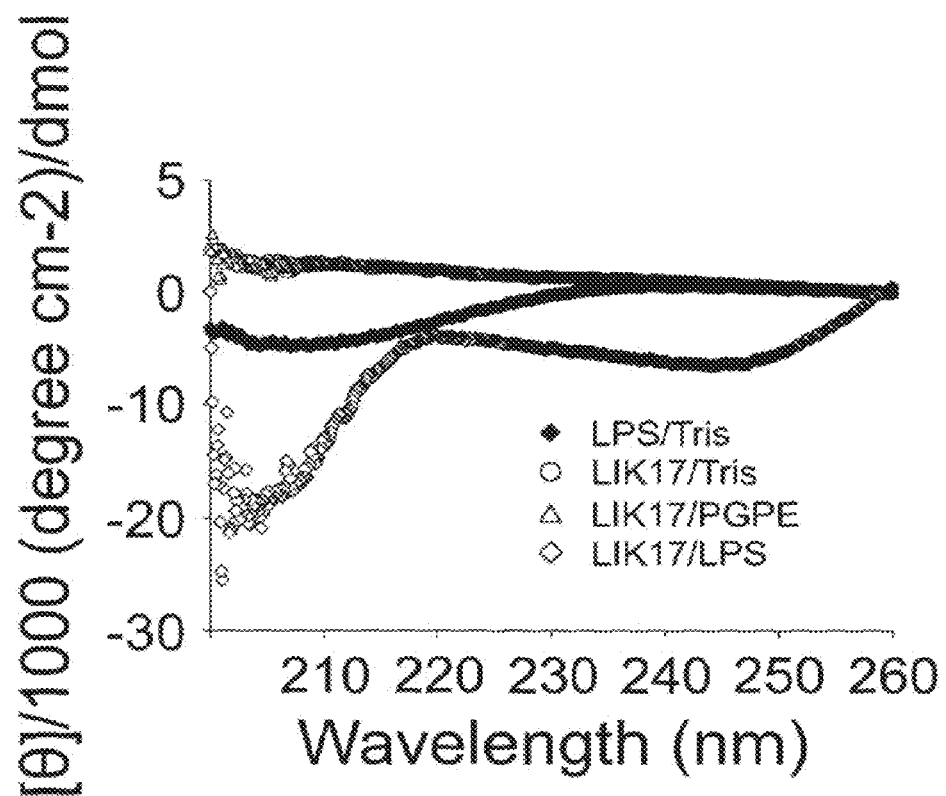

FIG. 12: CD spectra of LIK17 in Tris-buffer and in presence of LPS. For control, CD spectra for buffer and LPS alone are also presented.

Figure 13:
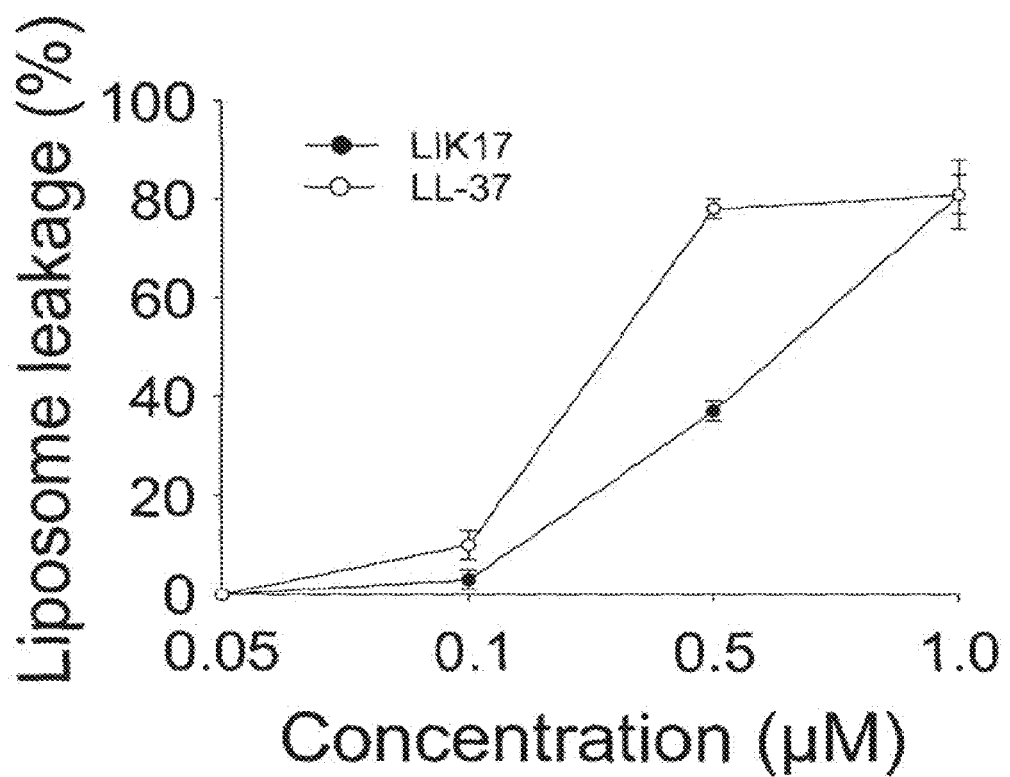

FIG. 13: Effects of the indicated peptides on liposome leakage.

The membrane permeabilizing effect was recorded by measuring fluorescence release of carboxyfluorescein from DOPE/DOPG (negatively charged) liposomes. The experiments were performed in 10 mM Tris-buffer, in absence and presence of 0.15 M NaCl. Values represents mean of triplicate samples.

Figure 14:
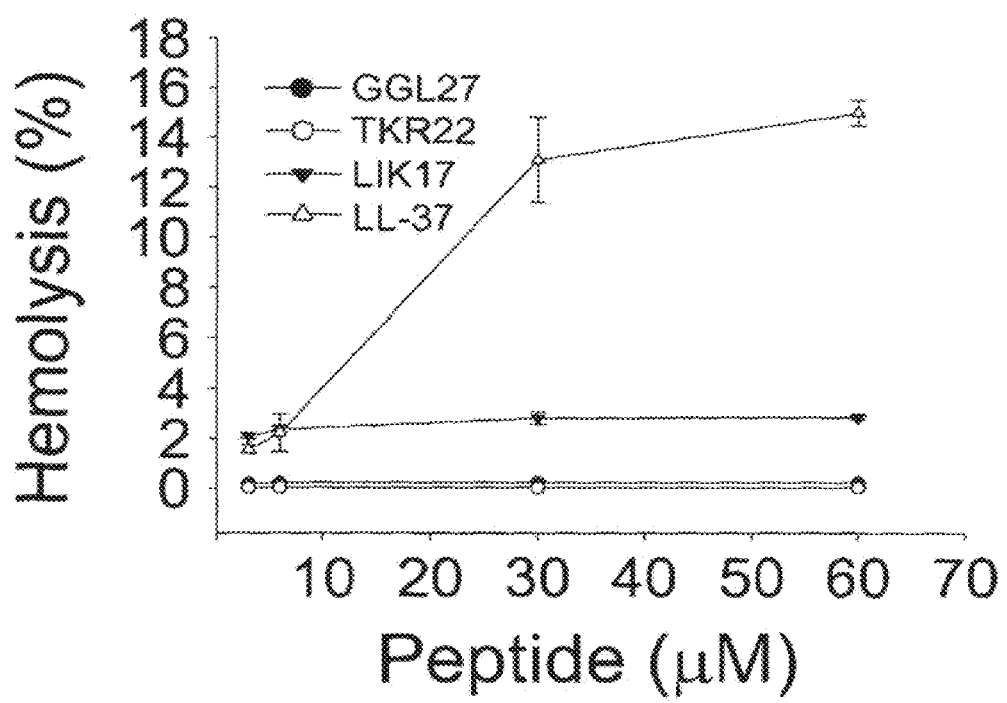

FIG. 14: Activities on eukaryotic cells

Hemolytic effects of the indicated peptides. The cells were incubated with different concentrations of the peptides, 2% Triton X-100 (Sigma-Aldrich) served as positive control. The absorbance of hemoglobin release was measured at λ 540 nm and is expressed as % of Triton X-100 induced hemolysis (note the scale of the y-axis). Effects of LL-37 are shown for comparison.

Figure 15:
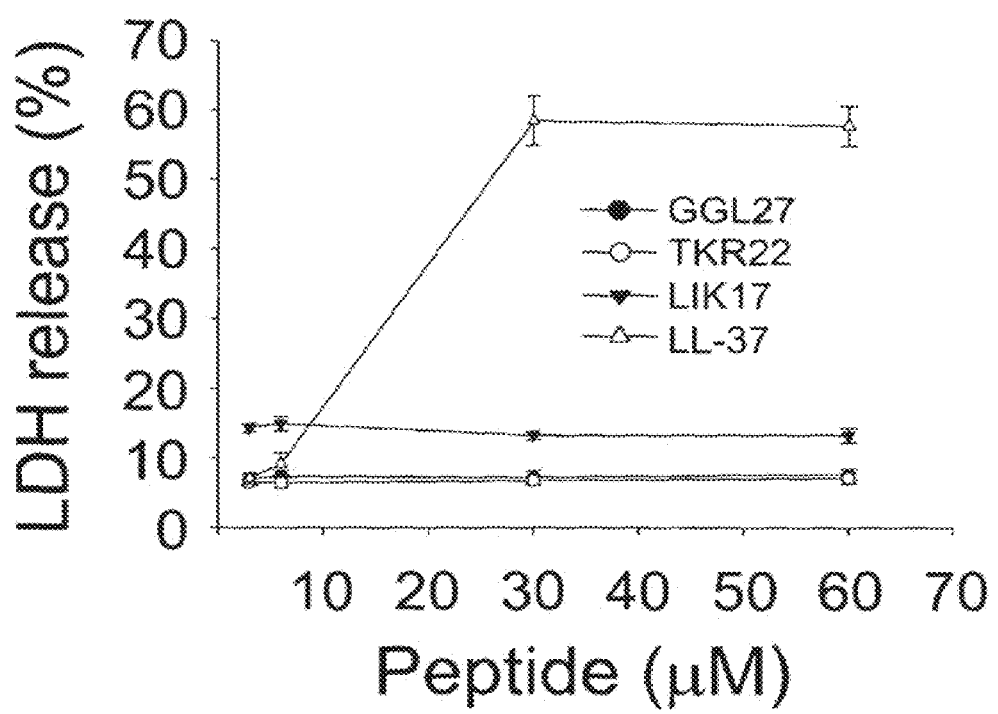

FIG. 15: HaCaT keratinocytes were subjected to the indicated TFPI-peptides as well as LL-37. Cell permeabilizing effects were measured by the LDH based TOX-7 kit. LDH release from the cells was monitored at λ 490 nm and was plotted as % of total LDH release.

Figure 16:
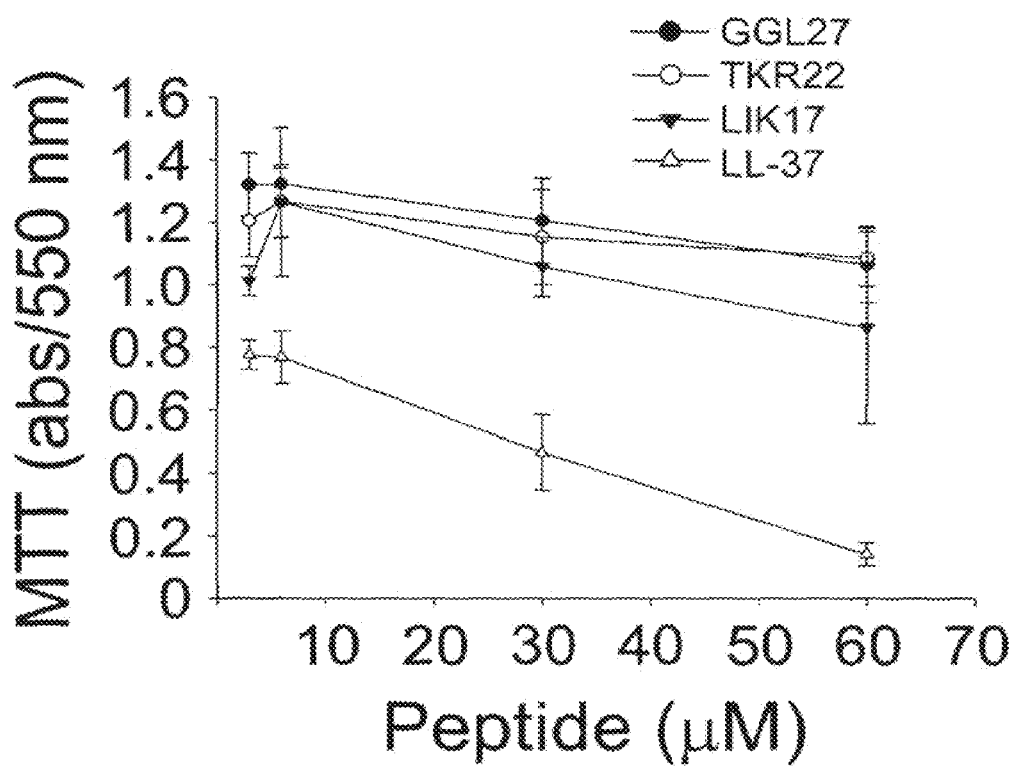

FIG. 16: The MTT-assay was used to measure viability of HaCaT keratinocytes in the presence of the indicated peptides (at 60 μM). In the assay, MTT is modified into a dye, blue formazan, by enzymes associated with metabolic activity. The absorbance of the dye was measured at λ 550 nm.

Figure 17:
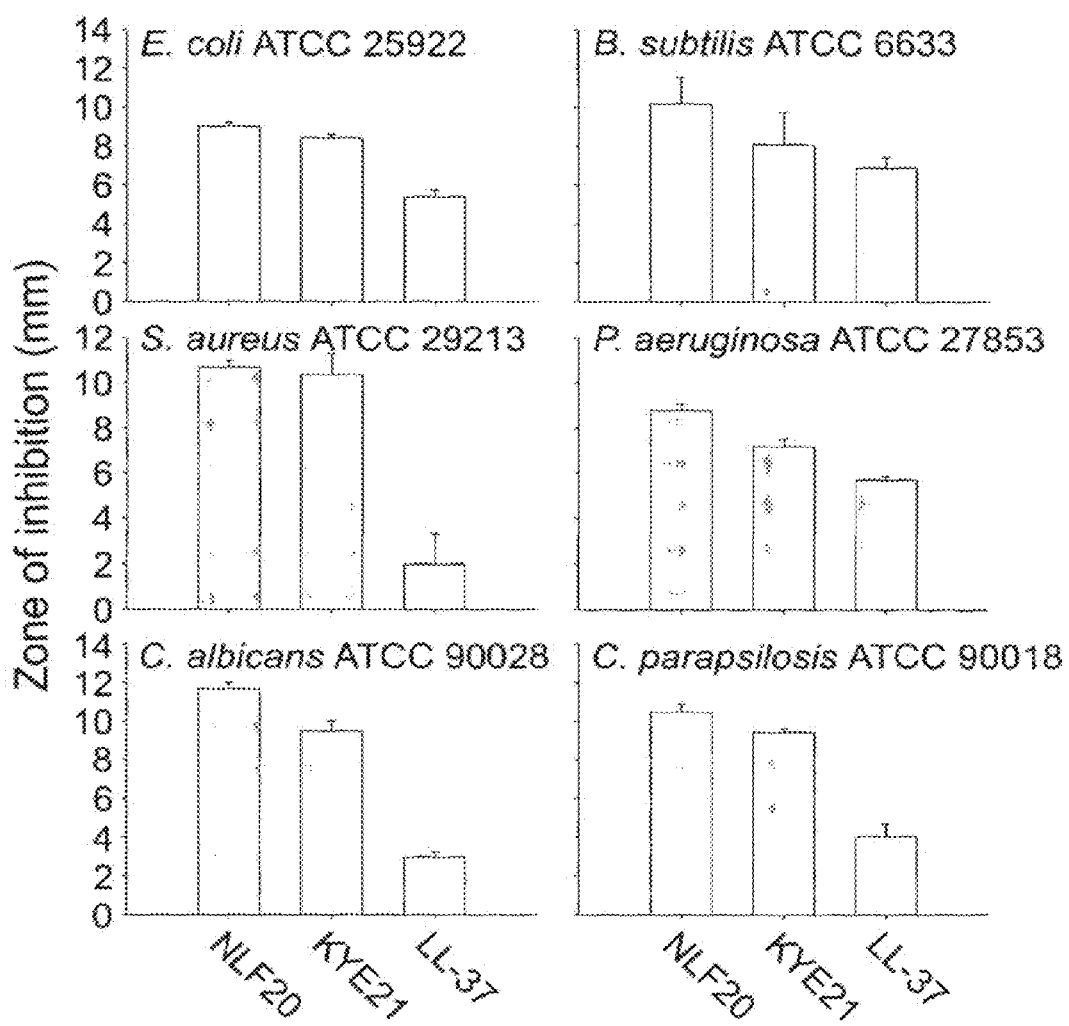

FIG. 17: Antimicrobial activities of heparin cofactor II-derived peptides.

Antimicrobial activity of selected peptides (at 100 μM) in RDA against the indicated microbes. For determination of antimicrobial activities, E. coli ATCC 25922, S. aureus ATCC 29213 isolates ($4 \times 10^6$ cfu) or C. parapsilosis ATCC 90018 ($1 \times 10^5$ cfu) was inoculated in 0.1% TSB agarose gel. Each 4 mm-diameter well was loaded with 6 μl of peptide. The zones of clearance correspond to the inhibitory effect of each peptide after incubation at 37° C. for 18-24 h (mean values are presented, n=3).

Figure 18:
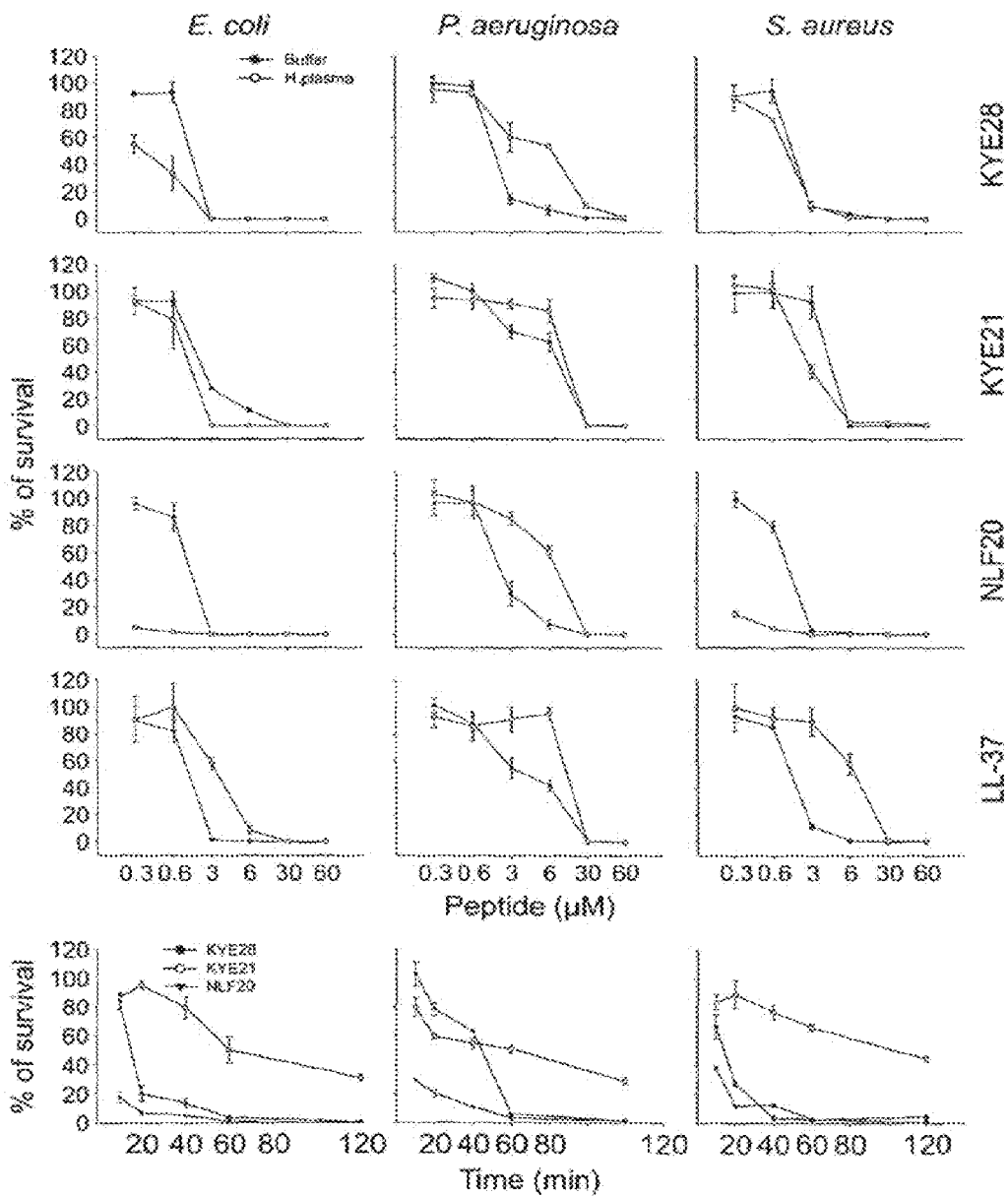

FIG. 18: (upper) Antibacterial effects of heparin cofactor II-derived peptides and LL-37 against E. coli, P. aeruginosa and S. aureus in viable count assays. $2 \times 10^6$ cfu/ml of bacteria were incubated in 50 μl with peptides at the indicated concentrations in 10 mM Tris, pH 7.4 buffer (Tris), or in 0.15 m NaCl, 10 mM Tris, pH 7.4 containing 20% human plasma (n=3, SD is indicated). (lower) The time-dependence of bacterial killing by GKR22 (at 6 and 30 μM) in 0.15 m NaCl, 10 mM Tris, pH 7.4 containing 20% plasma was analyzed by viable count assays using E. coli. LL-37 (30 μM) was used for comparison.

Figure 19:
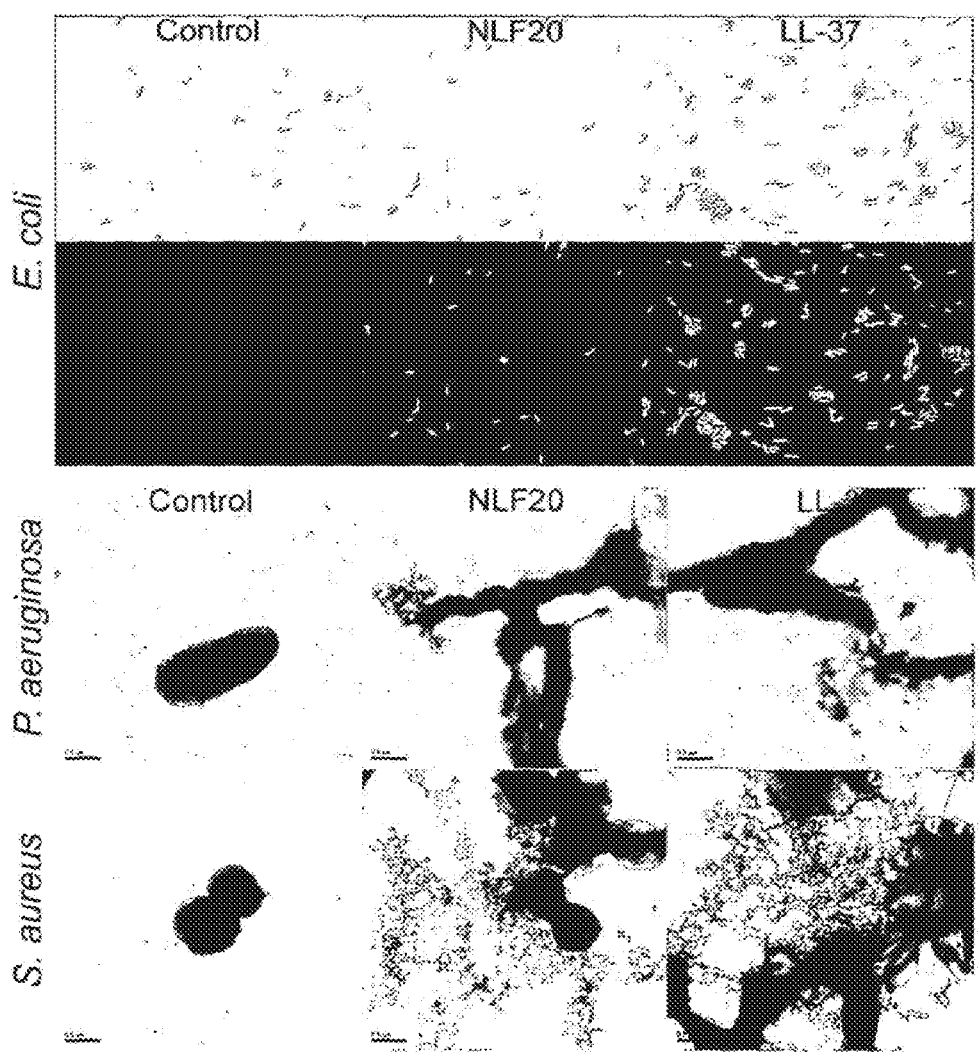

FIG. 19: Effects on bacterial membranes.

(A) Permeabilizing effects of peptides on P. aeruginosa and E. coli. (A) Bacteria were incubated with the indicated peptides and permeabilization was assessed using the impermeant probe FITC. (B) Electron microscopy analysis. P. aeruginosa and S. aureus bacteria was incubated for 2 h at 37° C. with 30 μM of NLF20 and LL-37 and analysed with electron microscopy. Scale bar represents 1 μm. Control; Buffer control.

Figure 20:
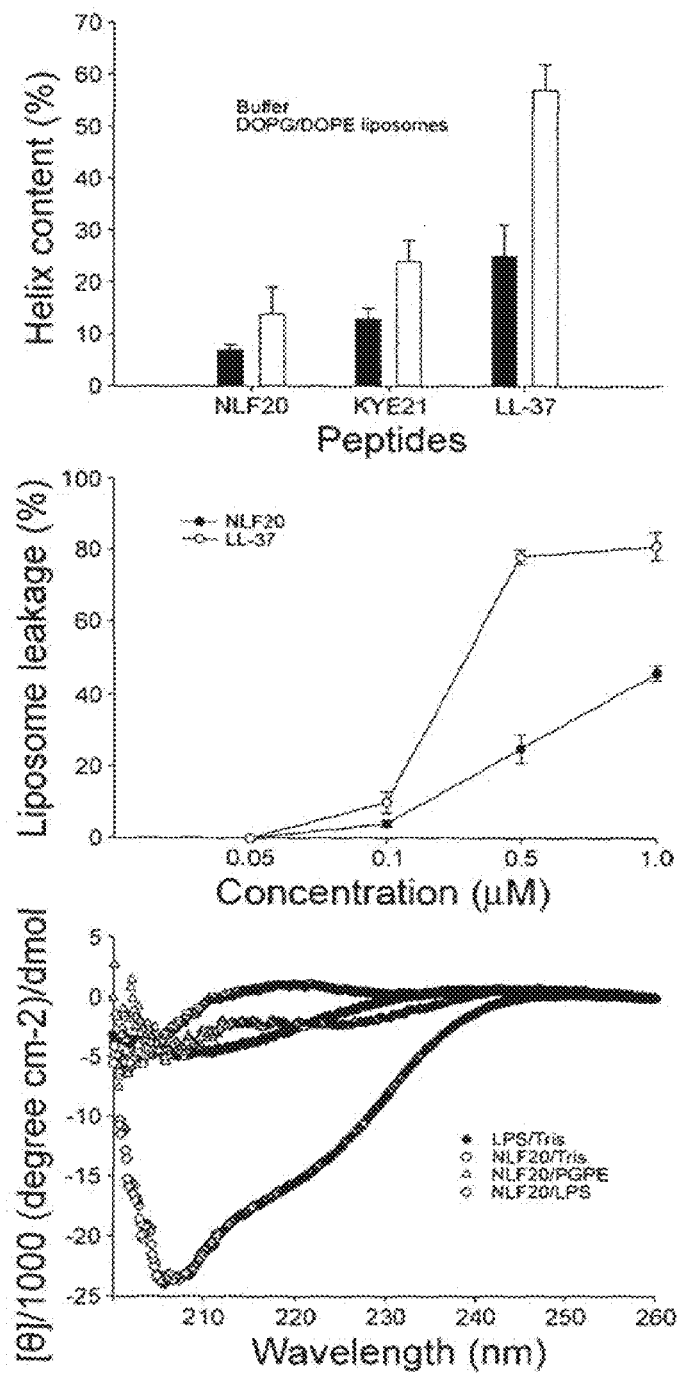

FIG. 20: Structure and effects on liposomes.

(A) Helical content of the heparin cofactor II-derived C-terminal peptides in presence of negatively charged liposomes (DOPE/DOPG). LIK17 structure was largely unaffected by the addition of liposomes. (B) CD spectra of NLF20 in Tris-buffer and in presence of LPS. For control, CD spectra for buffer and LPS alone are also presented. (C) Effects of NLF20 on liposome leakage. The membrane permeabilizing effect was recorded by measuring fluorescence release of carboxyfluorescein from DOPE/DOPG (negatively charged) liposomes. The experiments were performed in 10 mM Tris-buffer, in absence and presence of 0.15 M NaCl. Values represents mean of triplicate samples.

Figure 21:
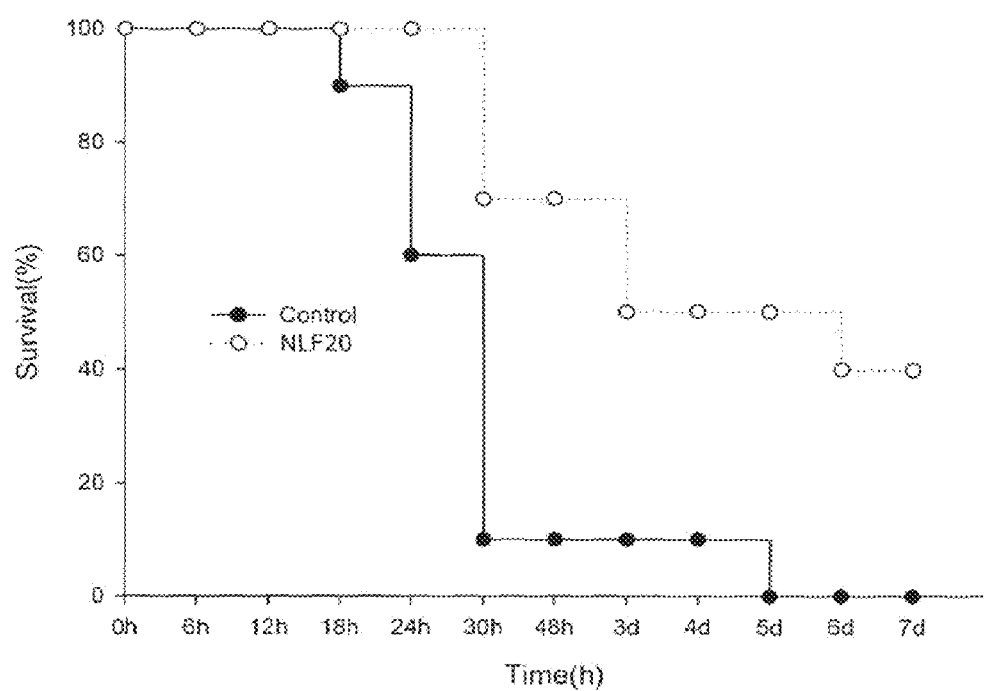

FIG. 21: Effects of NLF20 in an animal model of P. aeruginosa sepsis.

The thrombin HCII peptide NLF20 significantly increases survival. Mice were i.p. injected with P. aeruginosa bacteria, followed by subcutaneous injection of NLF20 or buffer only, after 1 h and then with intervals of 24 h for the three following days. Treatment with the peptide significantly increased survival.

Figure 22:
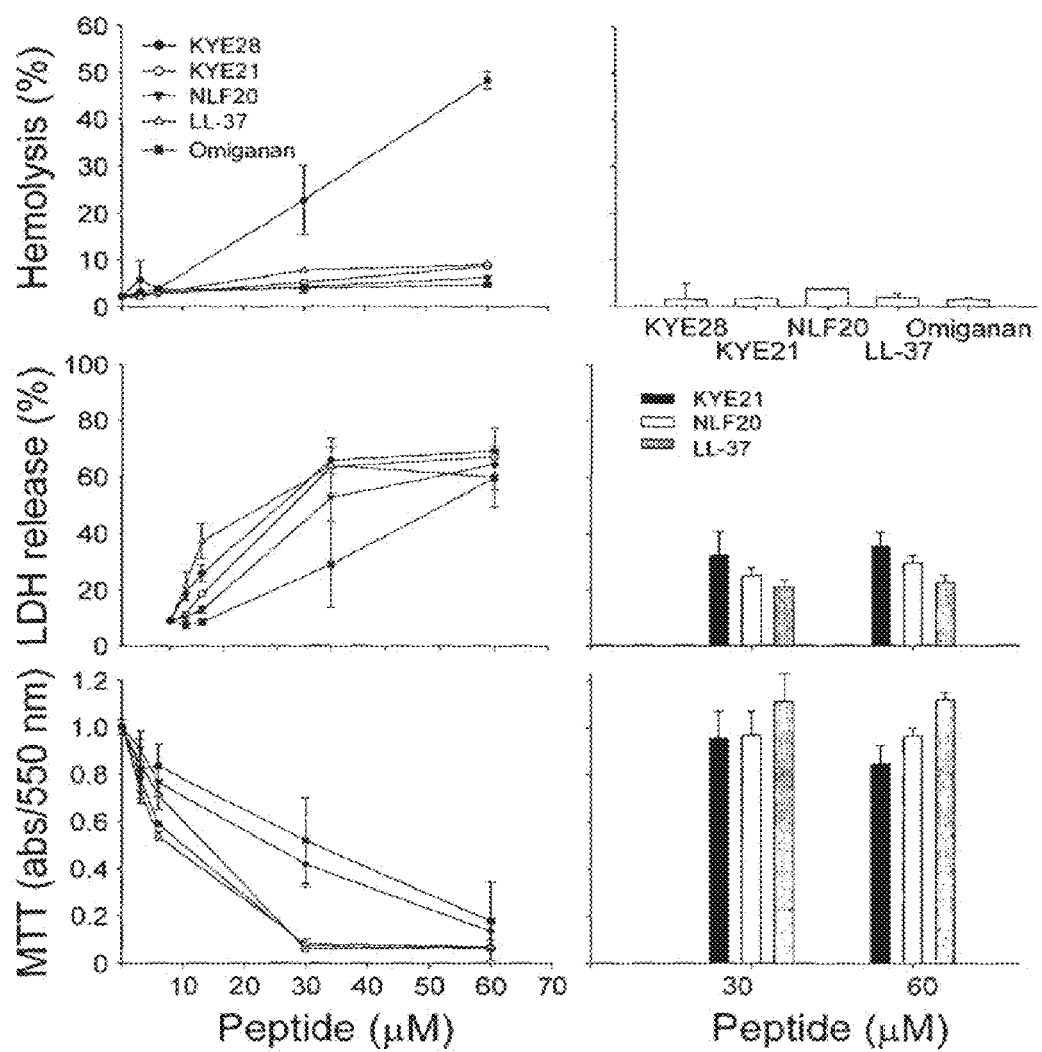

FIG. 22: Activities on eukaryotic cells (A) Hemolytic effects of the indicated peptides. The cells were incubated with different concentrations of the peptides, 2% Triton X-100 (Sigma-Aldrich) served as positive control. The absorbance of hemoglobin release was measured at λ 540 nm and is expressed as % of Triton X-100 induced hemolysis (note the scale of the y-axis). Effects of LL-37 are shown for comparison. (B) HaCaT keratinocytes were subjected to the indicated HCII-peptides as well as LL-37. Cell permeabilizing effects were measured by the LDH based TOX-7 kit. LDH release from the cells was monitored at λ 490 nm and was plotted as % of total LDH release. (C) The MTT-assay was used to measure viability of HaCaT keratinocytes in the presence of the indicated peptides (at 60 μM). In the assay, MTT is modified into a dye, blue formazan, by enzymes associated with metabolic activity. The absorbance of the dye was measured at λ 550 nm. Right panel shows results in presence of 20% plasma (hemolysis) or 20% serum (LDH and MTT).

Figure 23:
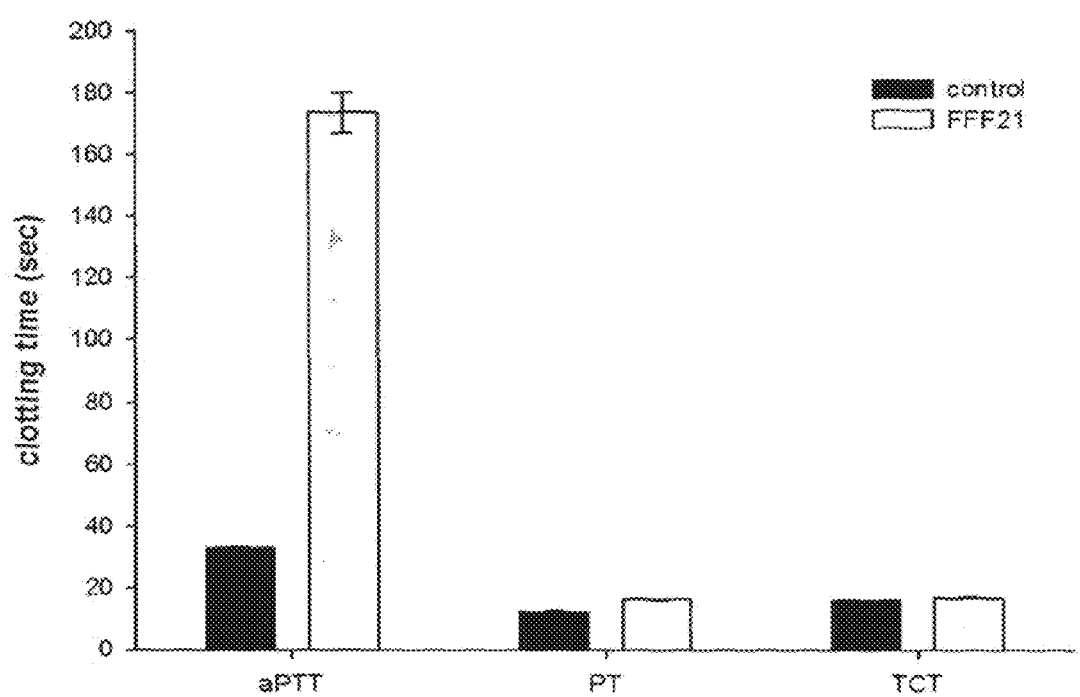

FIG. 23: Antithrombin III-derived peptide FFF21 blocks coagulation.

FFF21 impairs the intrinsic pathway of coagulation in normal human plasma determined by measuring the activated partial thromboplastin time (aPTT). Other parts of the coagulation system, as judged by the prothrombin time (PT) monitoring the extrinsic pathway of coagulation, and the thrombin clotting time (TCT), measuring thrombin induced fibrin network formation, were not significantly affected.

Figure 24:

FIG. 24. Structure of HCII

Cartoon illustrating HCII with KYE28 indicated.

Figure 25:
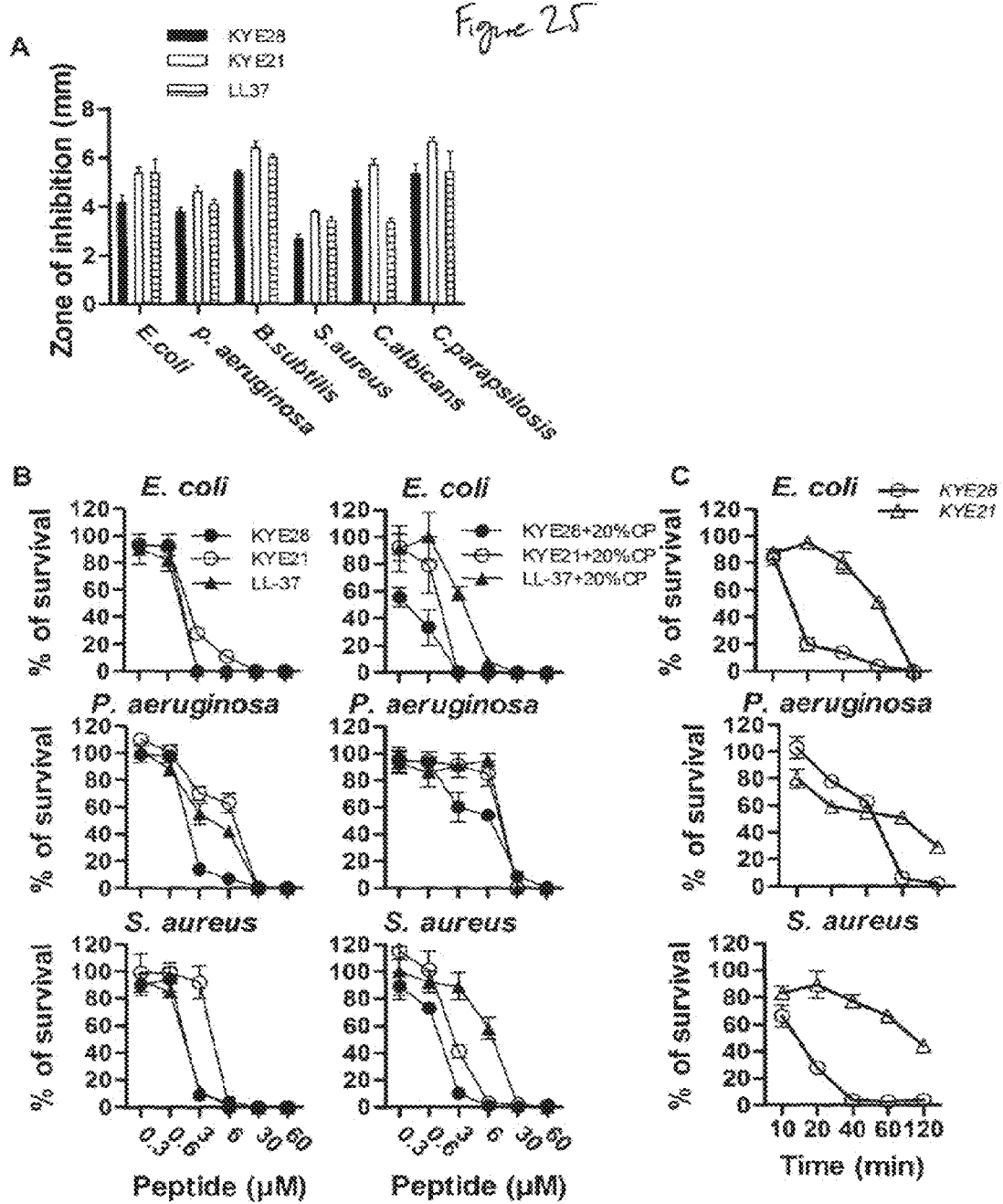

FIG. 25. Antimicrobial activities of HCII-derived peptides (A) Antimicrobial activity (using RDA of KYE28, KYE21, and LL-37 against the indicated microbes. For determination of antimicrobial activities, E. coli ATCC 25922, P. aeruginosa ATCC 27853, S. aureus ATCC 29213 or B. subtilis ATCC 6633 isolates ($4 \times 10^6$ cfu) or C. albicans ATCC 90028 and C. parapsilosis ATCC 90018 ($1 \times 10^5$ cfu) were inoculated in 0.1% TSB agarose gel. Each 4 mm-diameter well was loaded with 6 μl of peptide (at 100 μM). The zones of clearance correspond to the inhibitory effect of each peptide after incubation at 37° C. for 18-24 h (mean values are presented, n=3). (B) Antibacterial effects of KYE28, KYE21 and LL-37 against E. coli ATCC 25922, P. aeruginosa ATCC 27853, and S. aureus ATCC 29213 in viable count assays. $2 \times 10^6$ cfu/ml of bacteria were incubated in 50 μl with peptides at the indicated concentrations in $2 \times 10^6$ cfu/ml of bacteria were incubated in 50 μl with peptides at the indicated concentrations in 10 mM Tris, 0.15 M NaCl, pH 7.4 (buffer), or in 0.15 m NaCl, 10 mM Tris, pH 7.4 containing 20% human citrate plasma (CP) (n=3, SD is indicated), and the cfu were determined. (C) The time-dependence of bacterial killing by KYE29 and KYE21 (at 30 μM) in 0.15 M NaCl, 10 mM Tris, pH 7.4 containing 20% plasma was analyzed by viable count assays using the indicated bacteria.

Figure 26:
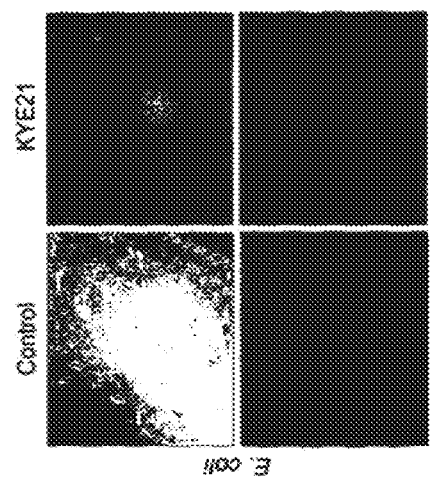

FIG. 26. Effects on bacterial membranes.

Permeabilizing effects of peptides on E. coli. Bacteria were incubated with the KYE21 and permeabilization was assessed using the impermeant probe FITC.

Figure 27:
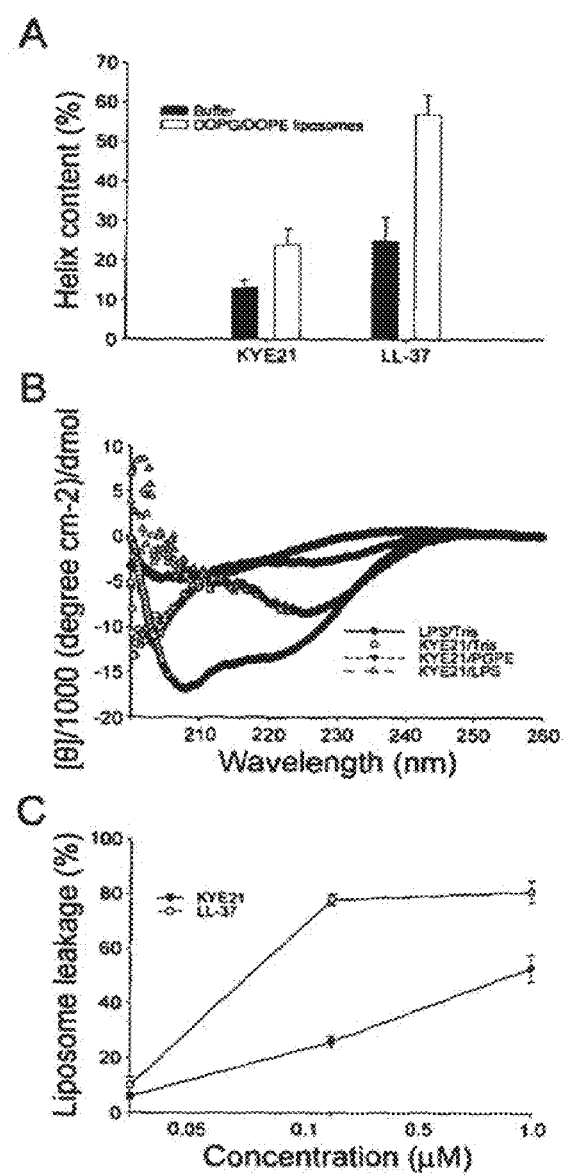

FIG. 27. Structure and effects on liposomes (A) Helical content of KYE21 in presence of negatively charged liposomes (DOPE/DOPG). The helical content was increased after the addition of liposomes. (B) CD spectra of KYE21 in Tris-buffer and in presence of LPS. Results with liposomes are shown for comparison. For control, CD spectra for buffer and LPS alone are also presented. (C) Effects of the KYE21 on liposome leakage. The membrane permeabilizing effect was recorded by measuring fluorescence release of carboxyfluorescein from DOPE/DOPG (negatively charged) liposomes. The experiments were performed in 10 mM Tris-buffer. Values represents mean of triplicate samples.

Figure 28:
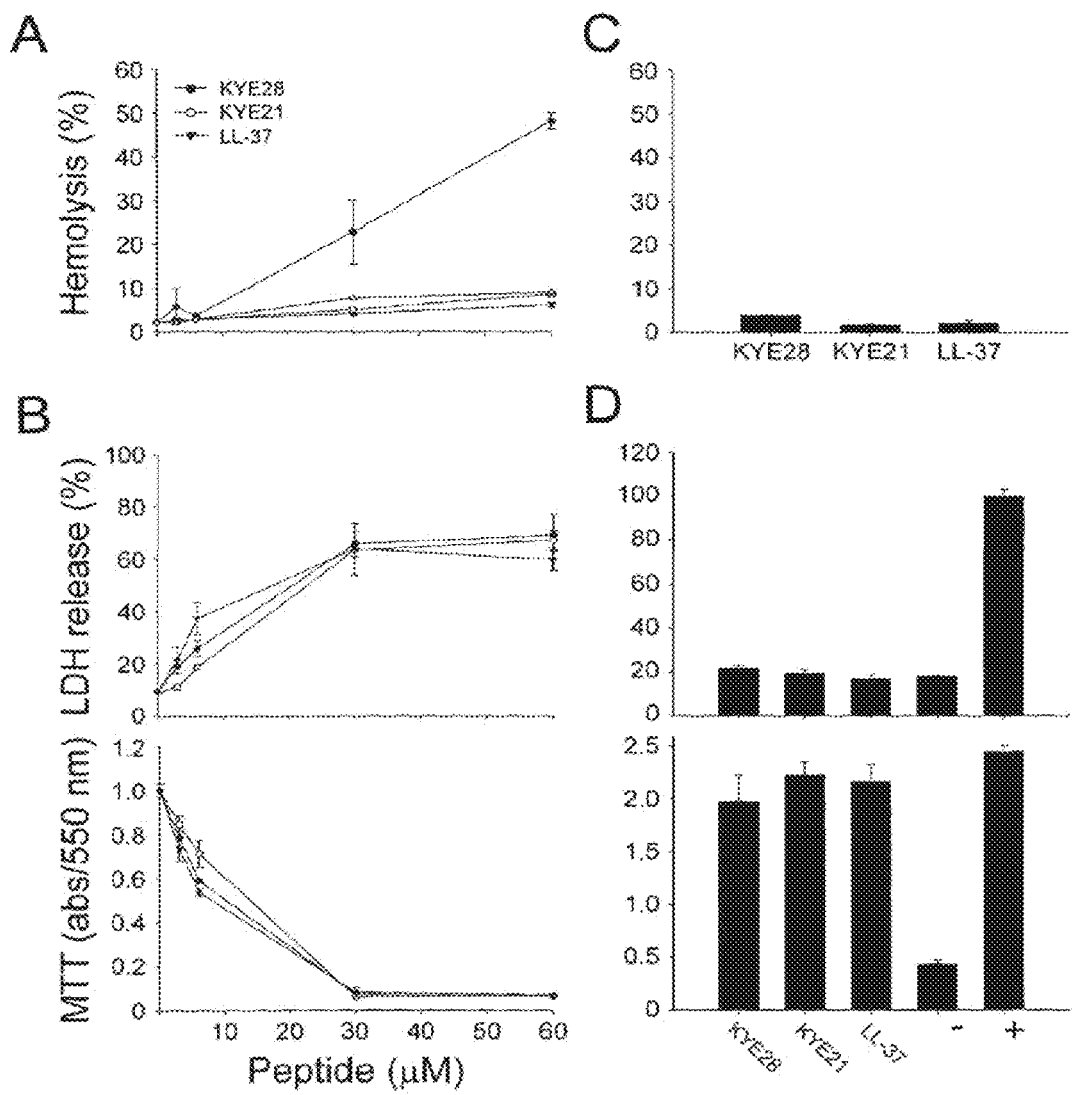

FIG. 28. Activities on eukaryotic cells (A) Hemolytic effects of the indicated peptides. The cells were incubated with different concentrations of the peptides, 2% Triton X-100 (Sigma-Aldrich) served as positive control. The absorbance of hemoglobin release was measured at λ 540 nm and is expressed as % of Triton X-100 induced hemolysis (note the scale of the y-axis). Effects of LL-37 are shown for comparison. (B) HaCaT keratinocytes were subjected to KYE28, KYE21, or LL-37. (Upper panel) Cell permeabilizing effects were measured by the LDH based TOX-7 kit. LDH release from the cells was monitored at λ 490 nm and was plotted as % of total LDH release. (Lower panel) The MTT-assay was used to measure viability of HaCaT keratinocytes in the presence of NLF20 or LL-37 (at 60 μM). In the assay, MTT is modified into a dye, blue formazan, by enzymes associated with metabolic activity. The absorbance of the dye was measured at λ 550 nm. (C) Hemolysis as above, but performed in 50% human blood diluted with PBS. (D) LDH release (upper panel) and MTT (lower panel) using HaCaT keratinocytes in presence of 20% human serum.

Figure 29:
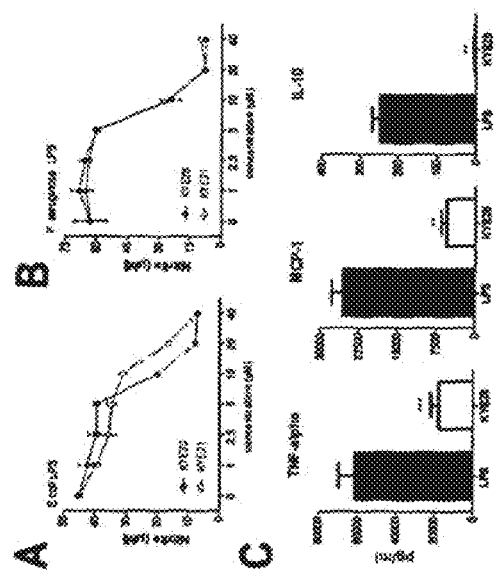
Figure 30:
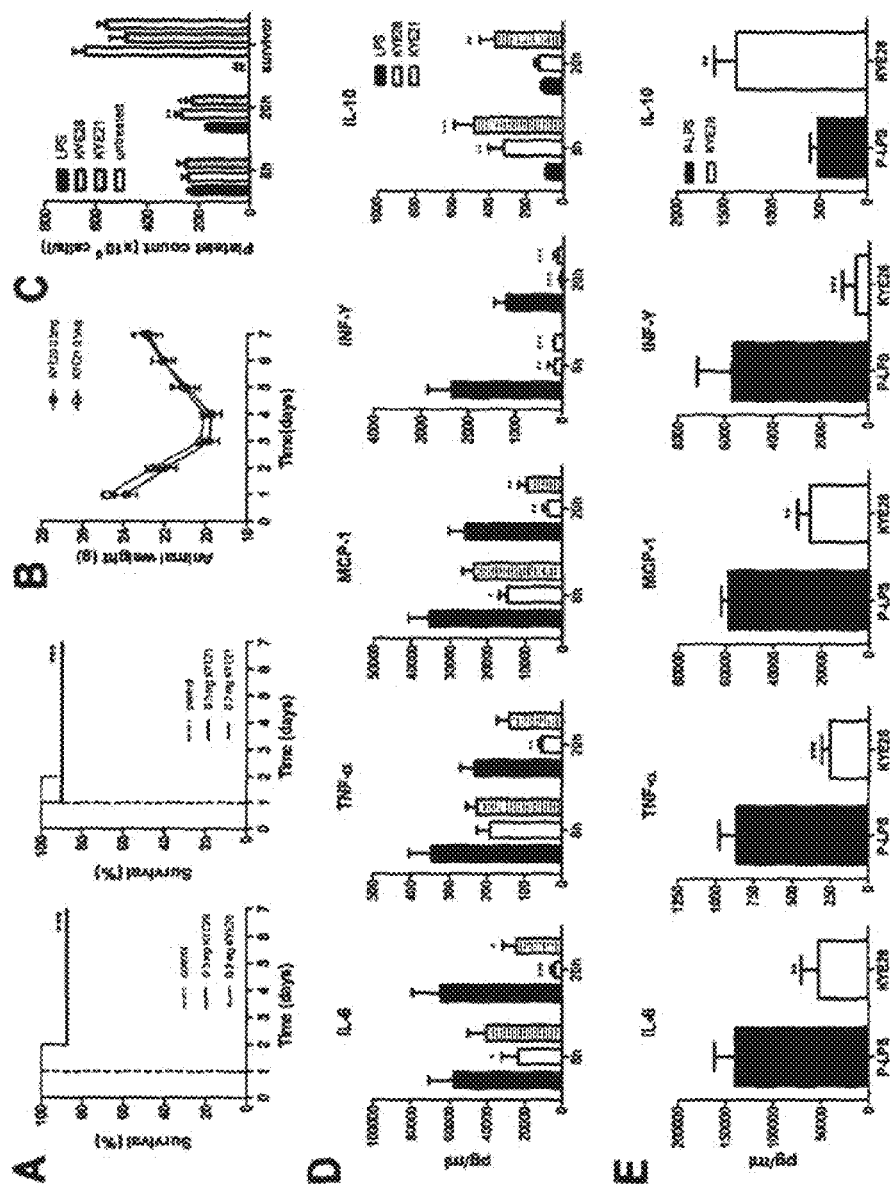

FIG. 29. HCII-derived peptides modulate the cytokine response to LPS in vitro (A) KYE28 and KYE21 significantly block nitrite production. RAW 264.7 macrophages were stimulated with 10 ng/ml E. coli LPS in combination with indicated concentrations of the two peptides. (B) Similar as above, but using P. aeruginosa LPS(C) KYE28 reduced TNF-α production, MCP-1 and IL-10 production in macrophages. RAW 264. 7 cells were stimulated with 10 ng/ml E. coli LPS and cytokines were analysed in the cell supernatants FIG. 30. Anti-inflammatory effects of HCII derived peptides in vivo Septic shock in C57BL6 mice was induced by intraperitoneal injection of 18 mg/kg E. coli LPS. Sixty minutes later KYE28 and KYE21 (0.2 and 0.5 mg; in PBS) or buffer only was administered. (A) Peptide treatment leads to significantly increased survival in LPS-induced shock compared to control mice (controls; n=, GKY25; n=, HVF; n=(p<0.001)). (B) Weight was followed for 7 days, and showed full recovery for treated mice. (C) Peptide treatment affects the number of platelets in the LPS-induced shock model. (D) In separate experiments mice were injected with LPS followed by administration of 0.5 mg of KYE28 or KYE21, or buffer. Animals were sacrificed at 8 h, 20 h, or after 7 days and the number of platelets in blood counted using the VetScanSystem. (D) Administration of KYE28 and KYE21 (0.5 mg) significantly attenuates the cytokine response compared to control mice. Cytokines were measured in blood from animals sacrificed at 8 or 20 h after LPS injection. (E) KYE28 decreases cytokine levels in P. aeruginosa LPS induced septic shock. C57BL6 were i.p. injected with 36 mg/kg LPS followed by 0.5 mg of KYE28 After 20 h mice were sacrificed and cytokine levels in blood were determined. (KYE28; n=10). All data are representative of two independent experiment.

FIG. 31. KYE28 and KYE21 prevent organ damage in a LPS model in vivo.

Lungs were analyzed by light microscopy after staining with hematoxylin-eosin, or analyzed by scanning electron microscopy 20 h after LPS injection i.p., followed by treatment with the indicated peptides (0.5 mg) or buffer. Treatment with the peptides KYE28 and KYE21 blocked leakage of proteins and erythrocytes (n=3 in both groups, and a representative lung section is shown).

Figure 32:
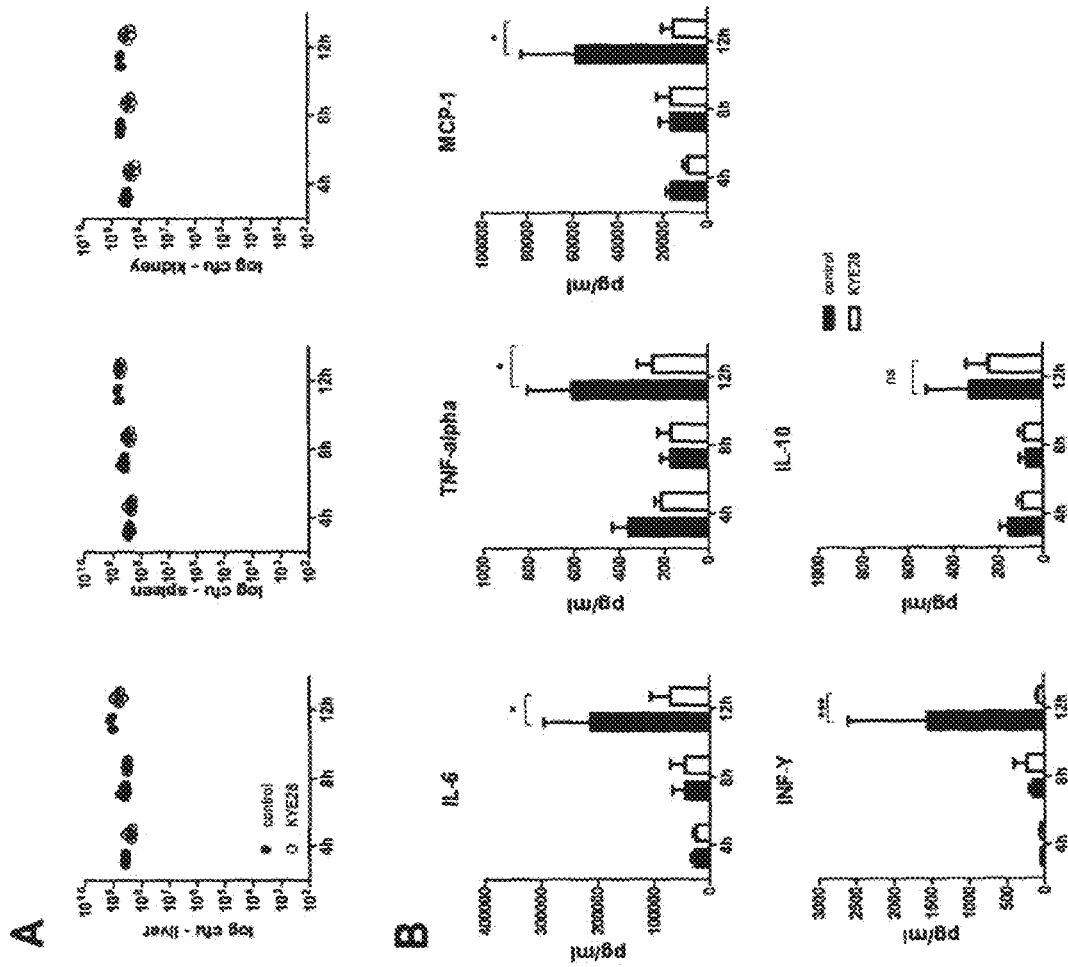

FIG. 32. Kinetics of P. aeruginosa infection in mice and effects on cytokines.

Mice were inoculated with P. aeruginosa and KYE28 (0.5 mg) was administered sc 1 h after infection. (A) Bacterial counts in the indicated organs were analyzed after a time period of 4, 8, and 12 h. (B) In parallel, the indicated cytokines were analyzed in blood.

Figure 33:
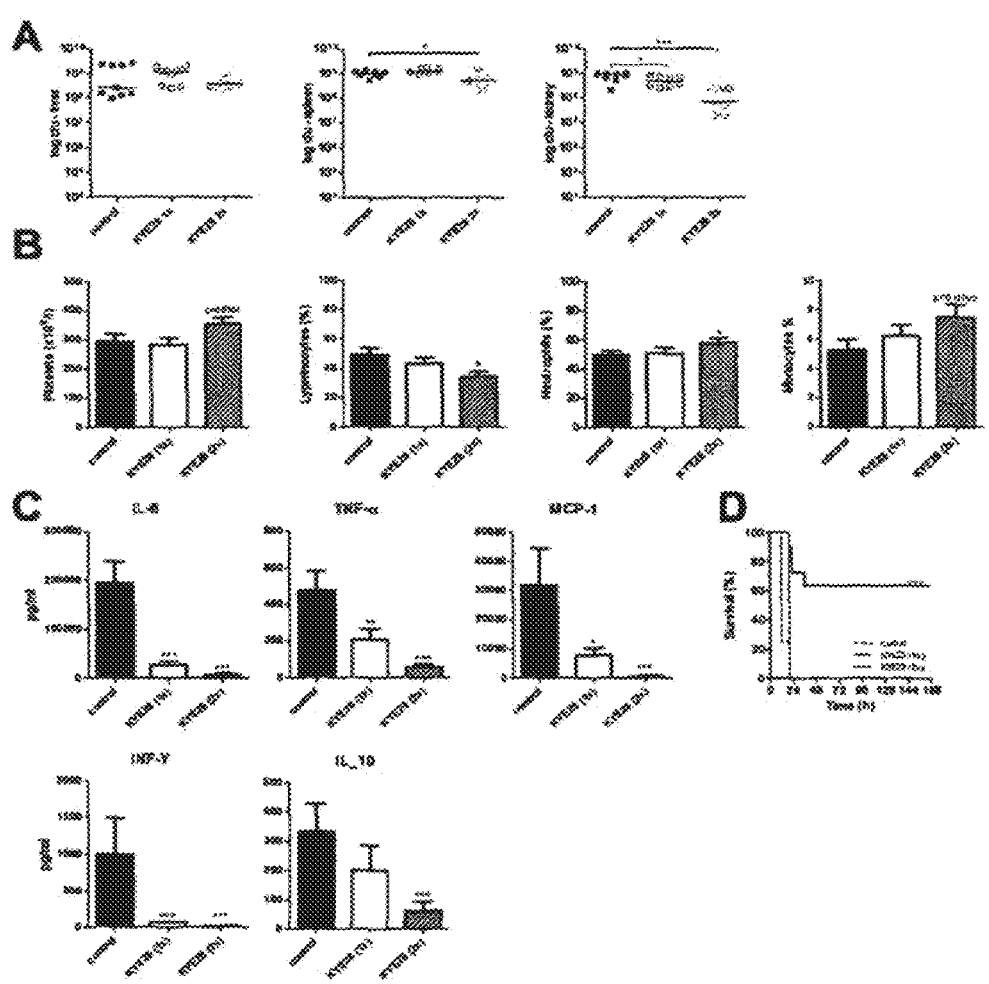

FIG. 33. Therapeutic efficiency of KYE28 in P. aeruginosa sepsis

Mice were inoculated with P. aeruginosa intraperitoneally and KYE28 was administered sc 1 h, or 1 and 7 h after inoculation with the bacteria. (A) Bacterial counts in the indicated organs were analyzed after a time period of 12 h. (B) Effects on platelets, lymphocytes, monocytes and neutrohils are shown. (C) In parallel, the indicated cytokines were analyzed in blood. (D) Mice were inoculated with P. aeruginosa and KYE28 was administered sc 1 h, or 1 and 7 h after inoculation with the bacteria, and survival of animals was registered. Administration of KYE28 twice (1 and 7 h after infection) significantly reduced mortality.

Figure 34:
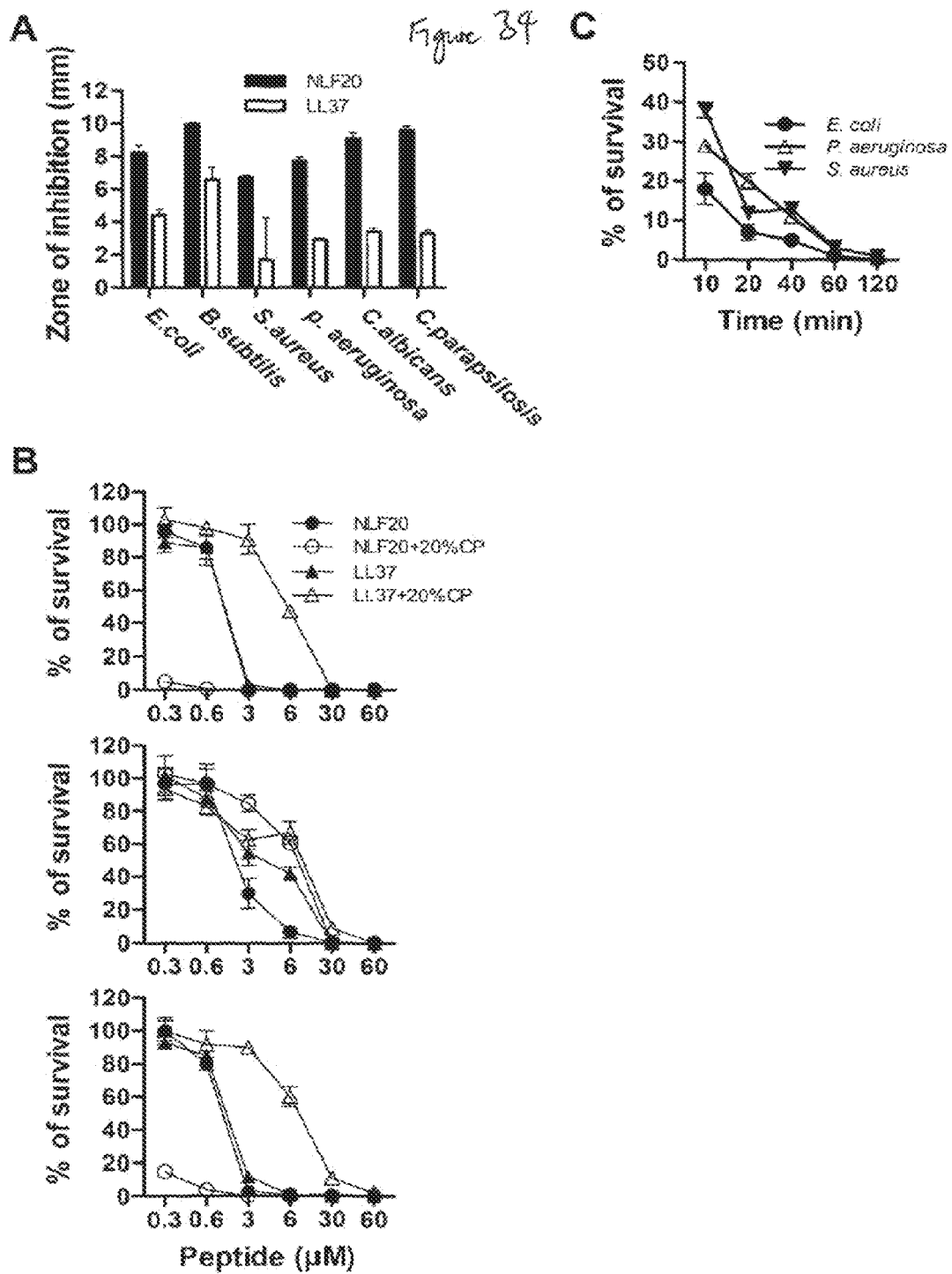

FIG. 34. Antimicrobial activities of NLF20

(A) Antimicrobial activity (using RDA of NLF20 against the indicated microbes. For determination of antimicrobial activities, E. coli ATCC 25922, P. aeruginosa ATCC 27853, S. aureus ATCC 29213 or B. subtilis ATCC 6633 isolates ($4 \times 10^6$ cfu) or C. albicans ATCC 90028 and C. parapsilosis ATCC 90018 ($1 \times 10^5$ cfu) were inoculated in 0.1% TSB agarose gel. Each 4 mm-diameter well was loaded with 6 μl of peptide (at 100 μM). The zones of clearance correspond to the inhibitory effect of each peptide after incubation at 37° C. for 18-24 h (mean values are presented, n=3). LL-37 is shown for comparison. (B) Antibacterial effects of NLF20 and LL-37 against E. coli ATCC 25922, P. aeruginosa ATCC 27853, and S. aureus ATCC 29213 in viable count assays. $2 \times 10^6$ cfu/ml of bacteria were incubated in 50 μl with peptides at the indicated concentrations in $2 \times 10^6$ cfu/ml of bacteria were incubated in 50 μl with peptides at the indicated concentrations in 10 mM Tris, 0.15 M NaCl, pH 7.4 (buffer), or in 0.15 m NaCl, 10 mM Tris, pH 7.4 containing 20% human citrate plasma (CP) (n=3, SD is indicated), and the cfu were determined. (C) The time-dependence of bacterial killing by NLF20 (at 30 μM) in 0.15 M NaCl, 10 mM Tris, pH 7.4 containing 20% plasma was analyzed by viable count assays using the indicated bacteria.

Figure 35:
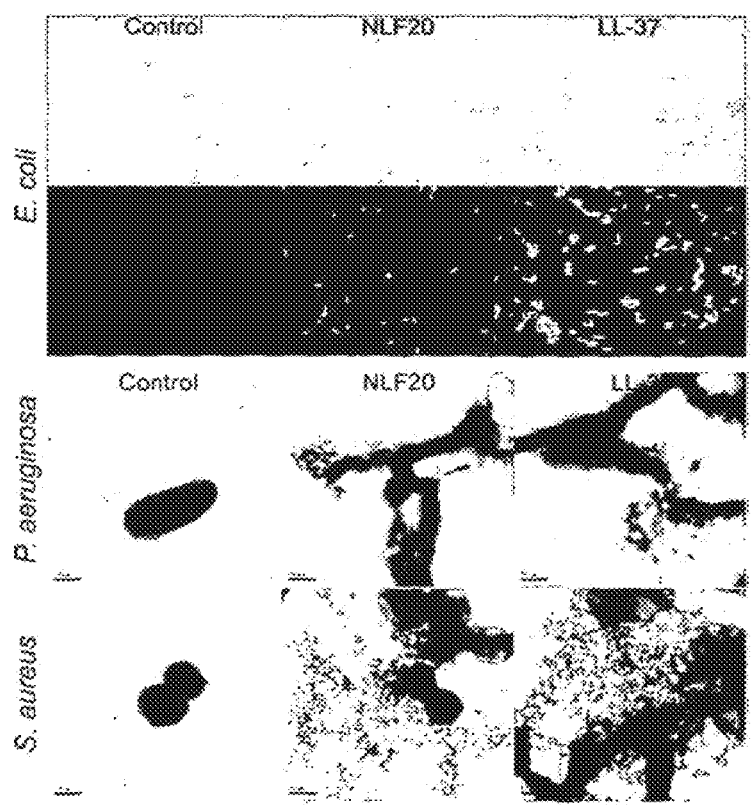

FIG. 35. Effects on bacterial membranes (A) Permeabilizing effects of peptides on E. coli. Bacteria were incubated with the NLF20 and permeabilization was assessed using the impermeant probe FITC. (B) Electron microscopy analysis. P. aeruginosa and S. aureus bacteria were incubated for 2 h at 37° C. with 30 μM of NLF20 and visualized by negative staining. LL-37 is shown for comparison. Scale bar represents 1 μm. Control; Buffer control.

Figure 36:
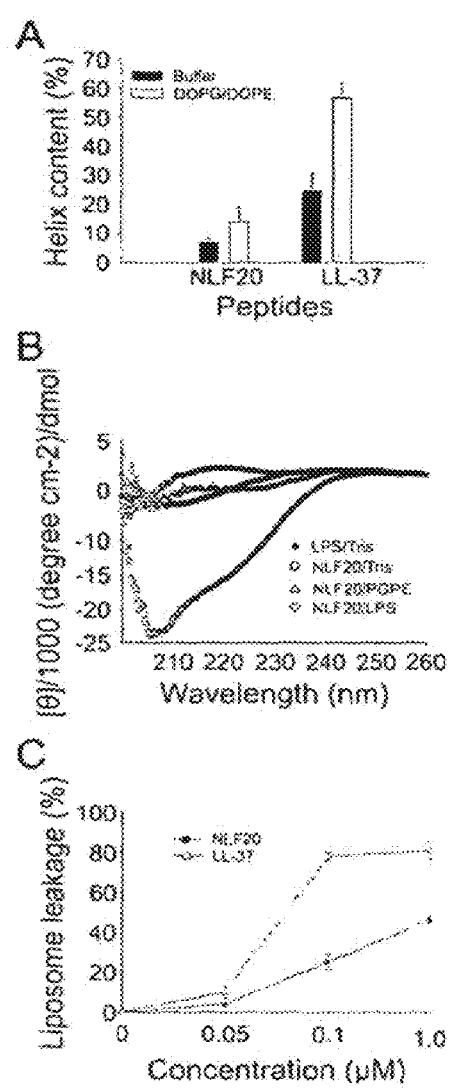
Figure 37:
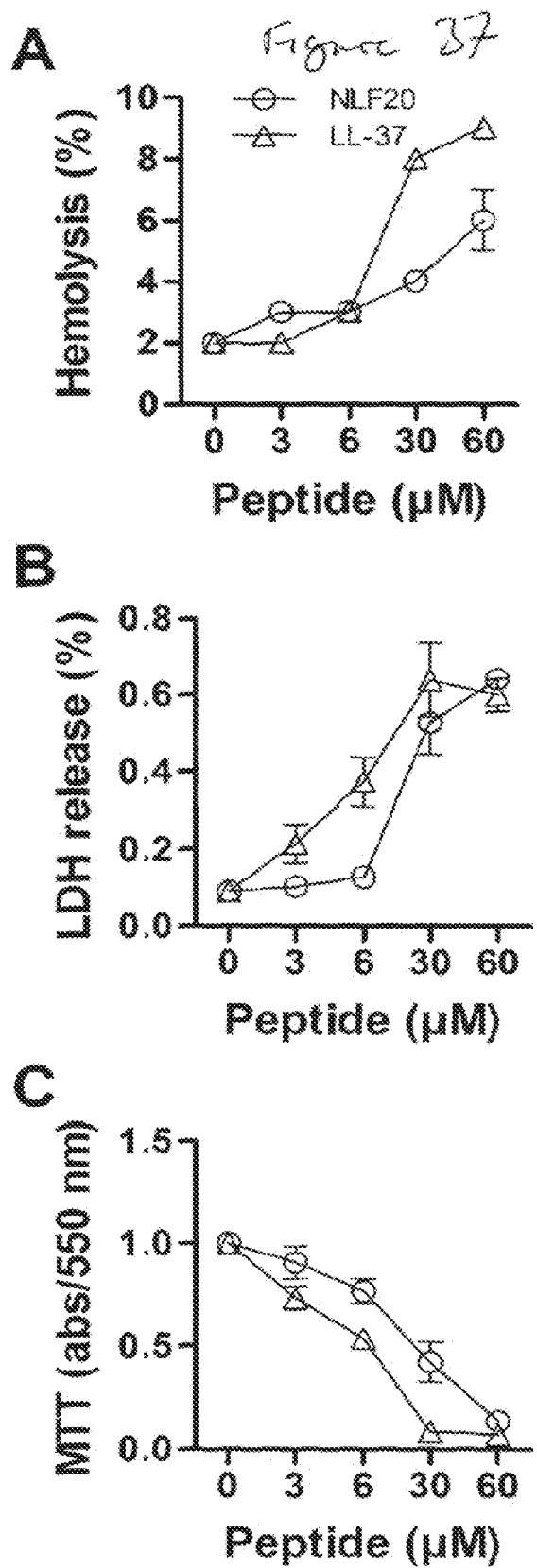

FIG. 36. Structure and effects on liposomes (A) Helical content of NLF20 in presence of negatively charged liposomes (DOPE/DOPG). The helical content was increased after the addition of liposomes. (B) CD spectra of NLF20 in Tris-buffer and in presence of LPS. Results with liposomes are shown for comparison. For control, CD spectra for buffer and LPS alone are also presented. (C) Effects of the indicated peptides on liposome leakage. The membrane permeabilizing effect was recorded by measuring fluorescence release of carboxyfluorescein from DOPE/DOPG (negatively charged) liposomes. The experiments were performed in 10 mM Tris-buffer. Values represents mean of triplicate samples.

Figure 37:
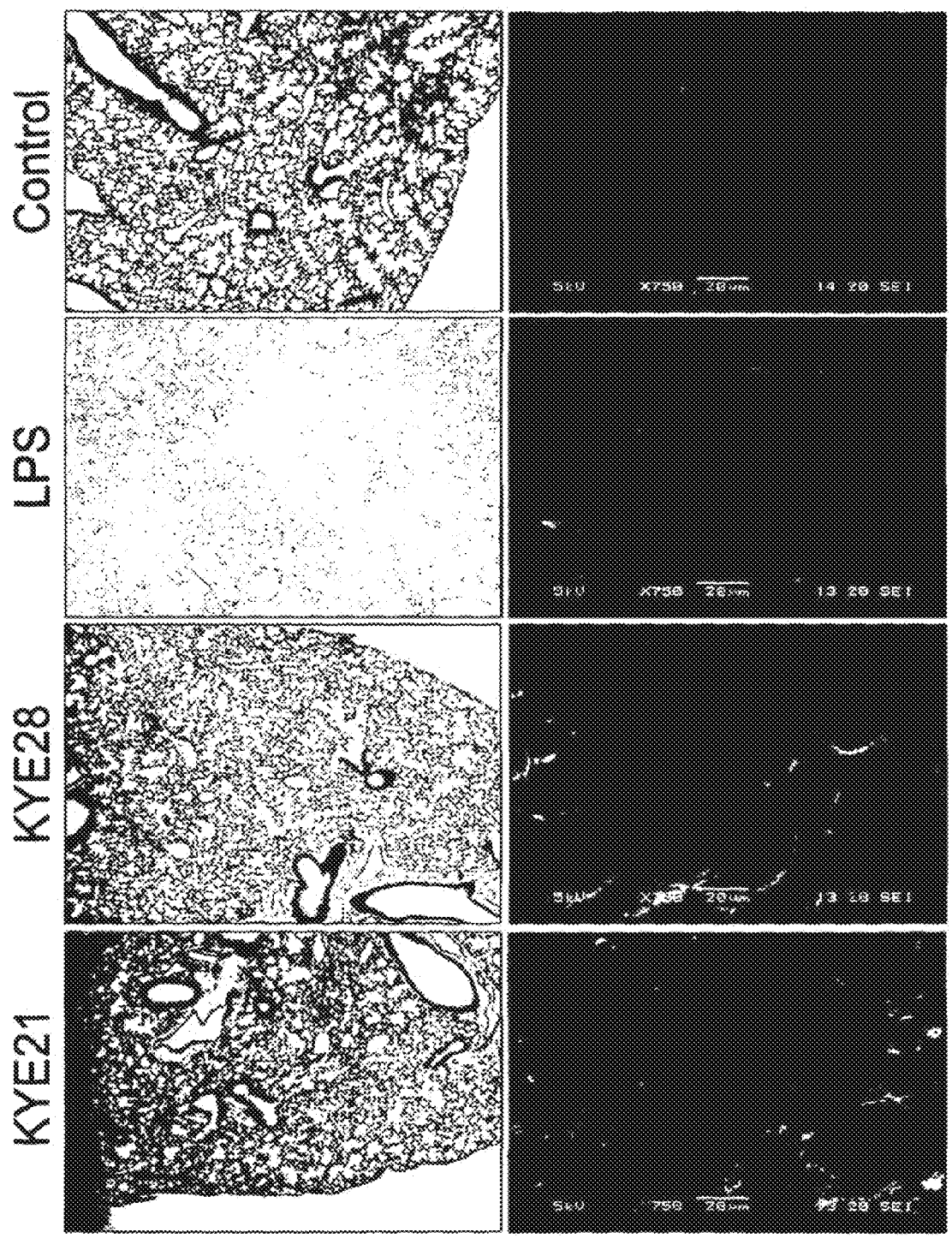

FIG. 37. Activities on eukaryotic cells (A) Hemolytic effects of the indicated peptides. The cells were incubated with different concentrations of the peptides, 2% Triton X-100 (Sigma-Aldrich) served as positive control. The absorbance of hemoglobin release was measured at $\lambda$ 540 nm and is expressed as % of Triton X-100 induced hemolysis (note the scale of the y-axis). Effects of LL-37 are shown for comparison. (B) HaCaT keratinocytes were subjected to NLF20 or LL-37. Cell permeabilizing effects were measured by the LDH based TOX-7 kit. LDH release from the cells was monitored at $\lambda$ 490 nm and was plotted as % of total LDH release. (C) The MTT-assay was used to measure viability of HaCaT keratinocytes in the presence of NLF20 or LL-37 (at 60 µM). In the assay, MTT is modified into a dye, blue formazan, by enzymes associated with metabolic activity. The absorbance of the dye was measured at $\lambda$ 550 nm.

Figure 38:
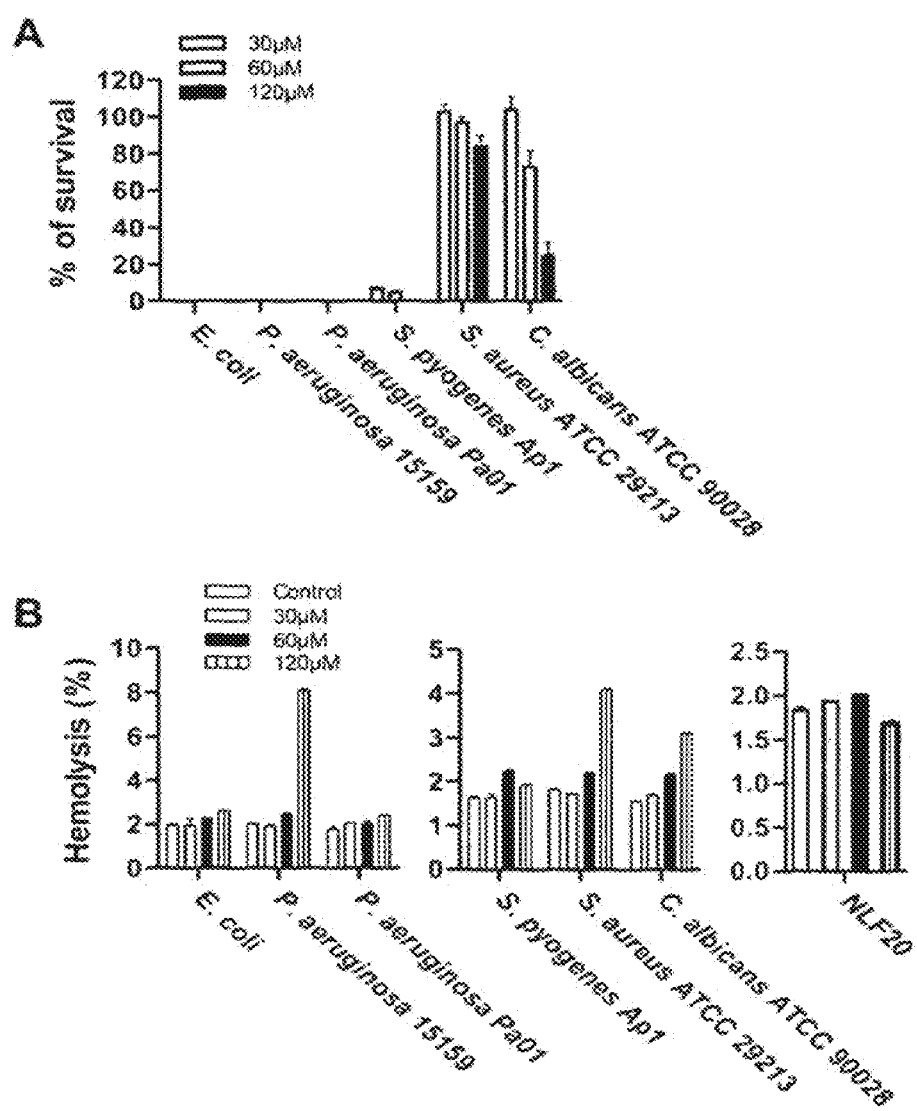

FIG. 38. Activities of NLF20 in human blood infected by bacteria (A) Antibacterial effects of NLF20 in presence of the indicated bacteria in human blood (made 50% in PBS) are presented. The indicated microbes ($2\times10^8$ cfu/ml) were added to 50% citrate blood, followed by addition of peptide at 30, 60 or 120 µM. The number of cfu was determined after an incubation period of 1 h. (B) In an identical setup, hemolysis effects were studied. The bacteria were added to 50% citrate blood, followed by addition of peptide. Hemolysis was assessed after 1 hour. The absorbance of hemoglobin release was measured at $\lambda$ 540 nm and is expressed as % of Triton X-100 induced hemolysis (note the scale of the y-axis. The rightmost panel show effects of NLF20 only incubated with blood.

Figure 39:
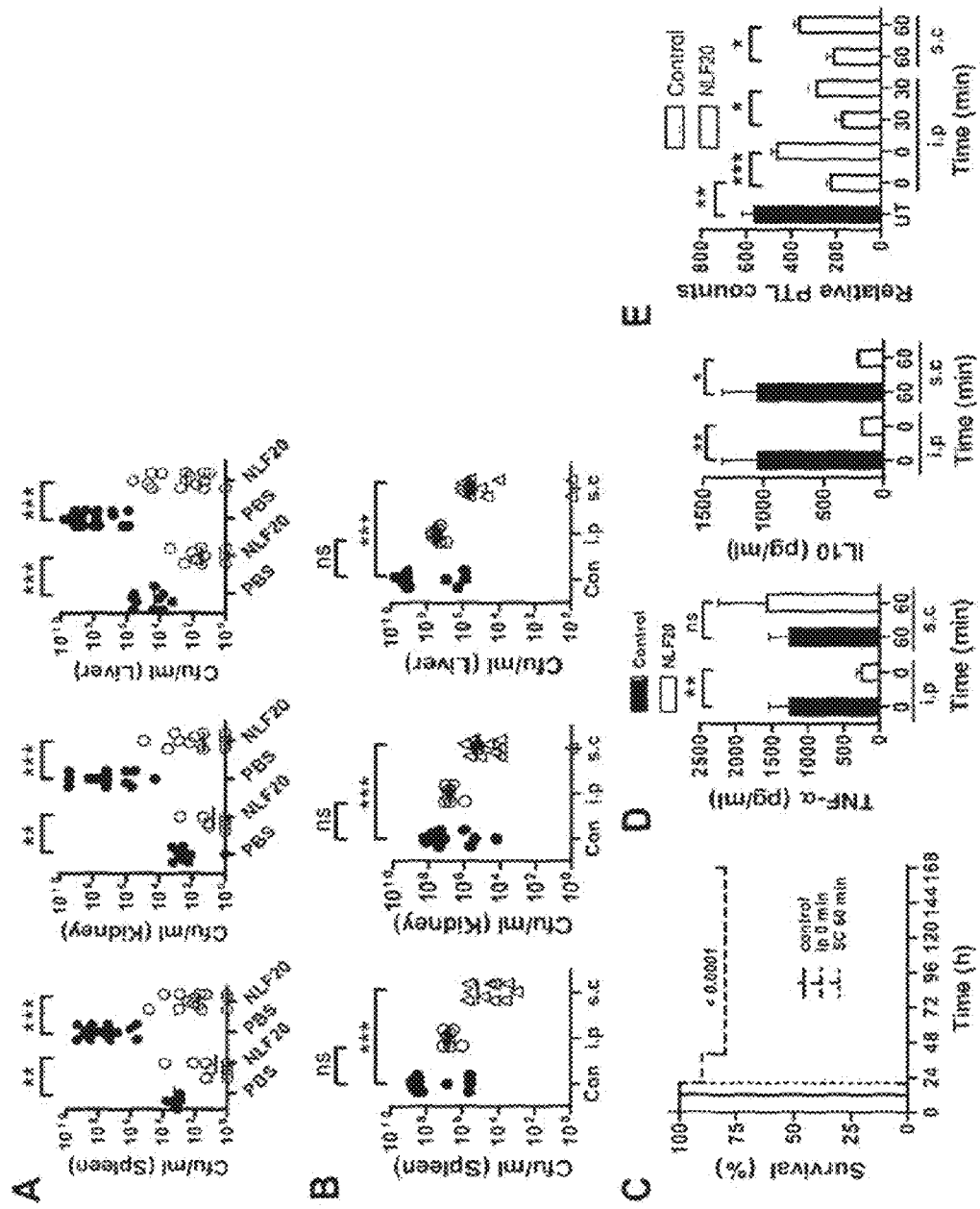

FIG. 39. Treatment of invasive *P. aeruginosa* infection with NLF20

(A) *P. aeruginosa* 15159 bacteria (in PBS, ~$2\times10^4$ or $2\times10^8$ cfu/ml) were kept on ice until injection. Hundred microliter of the bacterial suspension were injected intraperitoneally (ip) into C57/Bl6 mice. At ~10 min after the bacterial injection, 0.5 mg of NLF20 or PBS alone was injected ip into the mice. Liver, spleen and kidney were harvested, placed on ice, homogenized, and colony-forming units (cfu) determined 12 h after infection. (B) In a similar infection model ($2\times10^8$ cfu/ml of *P. aeruginosa*) intraperitoneal (ip) administration after 30 min was compared with subcutaneous injection (sc) after 1 h. 0.5 mg of NLF20 was used. (C) NLF20 significantly increases survival during *P. aeruginosa* sepsis. Mice were injected intraperitoneally with *P. aeruginosa* as above followed by ip or sc administration of NLF20 (500 µg). Survival was followed for 7 days. Whereas sc administration prolonged survival, ip administration significantly reduced mortality (n=for controls, n=for treated animals, P<0.0001 for ip administration). (D) NLF20 effects on TNF-α and IL-10 were analyzed in blood. (E) Thrombocytes were analyzed in blood. Treatment with NLF20 (ip and sc) increased thrombocyte levels.

Figure 40:
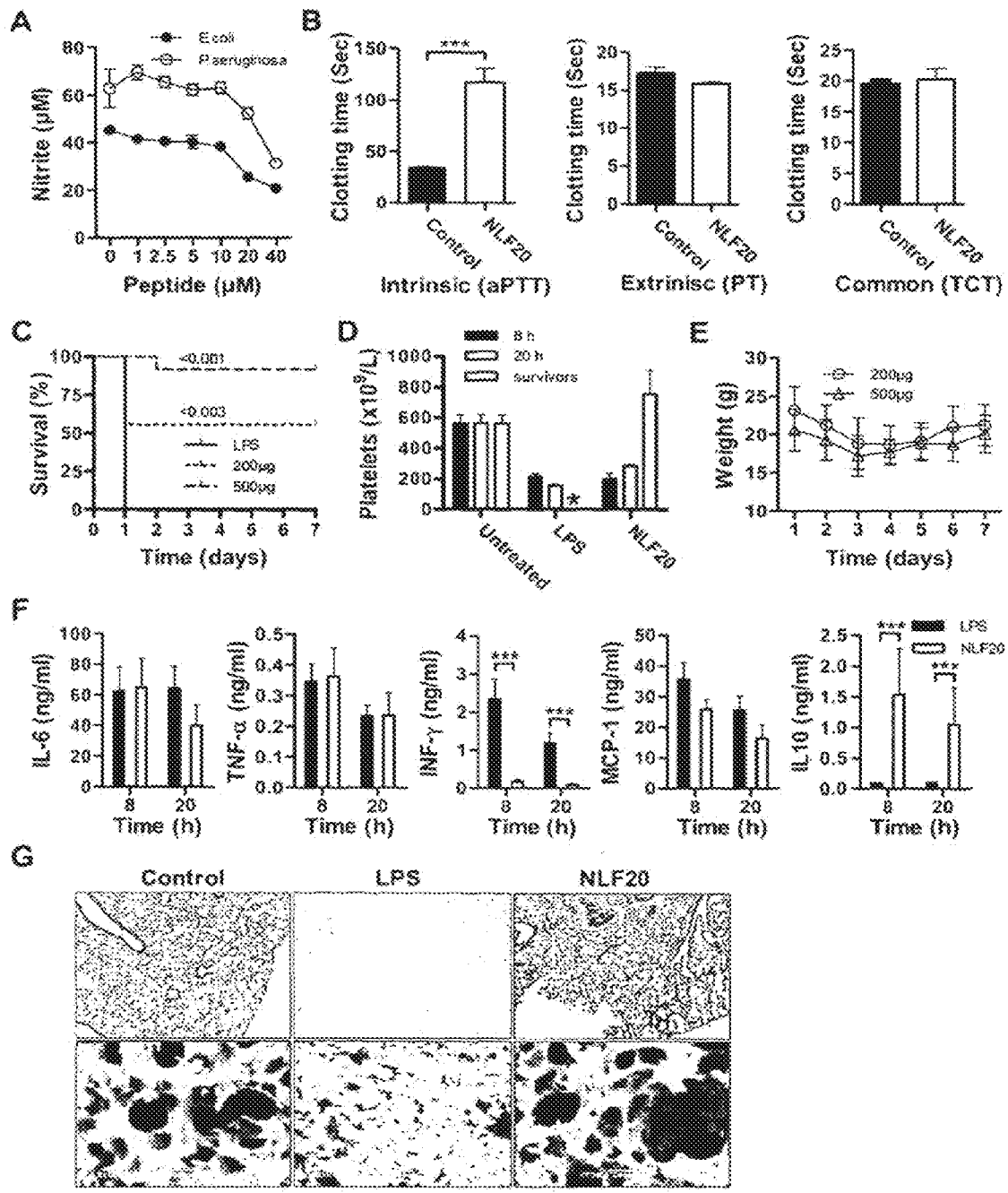

FIG. 40. Anti-inflammatory and anti-coagulative effects of NLF20 in vitro and in vivo (A) NLF20 significantly block nitrite production. RAW 264.7 macrophages were stimulated with 10 ng/ml *E. coli* or *P. aeruginosa* LPS in combination with indicated concentrations NLF20. (B) (B) NLF20 significantly prolongs the activated partial thrombin time (aPTT) in vitro. Clotting times were determined without (control) or with 20 µM of the peptide. Activated partial thromboplastin time (aPTT) was measured by incubating the peptides at the indicated concentrations in citrated human plasma for 1 minute followed by the addition of 100 µl aPTT reagent (aPTT Automate, Diagnostica Stago) for 60 seconds at 37° C. Clotting was initiated by the addition of $CaCl_2$ solution. Results illustrating the prothombin time assay (PT) and thrombin clotting time (TCT) are also presented. (C) Septic shock in C57BL6 mice was induced by intraperitoneal injection of 18 mg/kg *E. coli* LPS. NLF20 (0.2 or 0.5 mg in 10 mM Tris, pH 7.4) or buffer only was administered. NLF20 treatment significantly increases survival when compared to control mice (p<0.001 and 0.003, respectively). (E) Weight was followed for 7 days. (D) Peptide treatment significantly increases the number of platelets in the LPS-induced shock model. In separate experiments mice were injected with LPS followed by administration of 0.5 mg of NLF20, or buffer. Animals were sacrificed at 8 h, 20 h, and survivors after 7 days and the number of platelets in blood counted using the VetScanSystem. (F) Administration of NLF20 (0.5 mg) selectively modulates the cytokine response compared to control mice. Cytokines were measured in blood from animals sacrificed at 8 or 20 h after LPS injection. (G) NLF abrogates inflammation in lungs. Lungs were analyzed by light microscopy after staining with hematoxylin-eosin, or analyzed by scanning electron microscopy 20 h after LPS injection i.p., followed by treatment with NLF20 (0.5 mg) or buffer. Treatment with the peptide blocked leakage of proteins and erythrocytes (n=3 in both groups, and a representative lung section is shown).

FIG. 41. Peptides of heparin-cofactor II block coagulation

KYE28 and NLF20 impair the intrinsic pathway of coagulation in normal human plasma determined by measuring the activated partial thromboplastin time (aPTT). KYE21 shows only minor blocking of the aPTT. Other parts of the coagulation system, as judged by the prothrombin time (PT) monitoring the extrinsic pathway of coagulation, and the thrombin clotting time (TCT), measuring thrombin induced fibrin network formation, were not significantly affected.

EXAMPLES

Example A

Introduction

Heparin Cofactor II

Serpins are a group of proteins with similar structures that were first identified as a set of proteins able to inhibit proteases. The acronym serpin was originally coined because many serpins inhibit chymotrypsin-like serine proteases (serine protease inhibitors). The first members of the serpin superfamily to be extensively studied were the human plasma proteins antithrombin and antitrypsin, which play key roles in controlling blood coagulation and inflammation, respectively.

Structural studies on serpins have revealed that inhibitory members of the family undergo an unusual conformational change, termed the Stressed to Relaxed (S to R) transition. This conformational mobility of serpins provides a key advantage over static lock-and-key protease inhibitors. In particular, the function of inhibitory serpins can be readily controlled by specific cofactors like heparin. The archetypal example of this situation is antithrombin, which circulates in plasma in a relatively inactive state. Upon binding a high-affinity heparin pentasaccharide sequence within long-chain heparin, antithrombin undergoes a conformational change, exposing key residues important for the mechanism. The heparin pentasaccharide-bound form of antithrombin is, thus, a more effective inhibitor of thrombin and factor Xa. Furthermore, both of these coagulation proteases contain binding sites (called exosites) for heparin. Heparin, therefore, also acts as a template for binding of both protease and serpin, further dramatically accelerating the interaction between the two parties. After the initial interaction, the final serpin complex is formed and the heparin moiety is released.

Peptides corresponding to the heparin binding sites in these proteins possess antibacterial, anti-inflammatory and anti-coagulation properties.

Tissue Factor Pathway Inhibitor (TFPI)

Tissue factor pathway inhibitor (or TFPI) is a Kunitz-type protinase inhibitor which reversibely inhibits the tissue factor-factor VII (TF-VII) complex in a factor X (FX) dependent manner, leading to inhibition of both FX and FIX activation. TFPI consists of a highly negatively-charged amino-terminus, three tandemly-linked Kunitz-type domains, and a highly positively-charged carboxy-terminus. In plasma, TFPI exists in both full-length and variably C-terminal truncated forms [28]. The first and second Kunitz domains are involved in binding and inhibition of the TF-VII complex and factor Xa, respectively [29]. The third Kunitz domain may via its cationic residues, including amino acid sequences at the C-terminal end, interact with heparin [30]. This C-terminal region has also been implicated in interaction with plasma lipoproteins, thrombospondin-1, clearance receptors ([31]), lipopolysaccharide [32] and may inhibit cell growth [33] as well as blood coagulation [34], [35]. Since various C-terminally truncated forms exist in vivo, a potential role of proteolysis of the C-terminus has been implicated, and data indicate that TFPI can be cleaved by various proteinases such as thrombin [36], plasmin [37], and matrix metalloptoteinase-8 [38], releasing C-terminal fragments. Upregulators of TFPI expression include endotoxin, IL-1, TNF-α, platelet-derived growth factor, heparin, and basic fibroblast growth factor, all physiological mechanisms involved in infection, inflammation, and growth [31].

The above reported multifunctionality of TFPI, and presence of an exposed cationic and heparin-binding C-terminus made us raise the question whether the C-terminal region of TFPI could exert a direct antimicrobial activity. We here show that C-terminal TFPI peptides may indeed directly kill both Gram-negative and Gram-positive bacteria and fungi. Furthermore, evidence is presented that the peptides may, also exert anticoagulant and antiinflammatory effects.

Materials and Methods

Radioiodination of Heparin and LPS.

The radioiodination of heparin (from porcine intestinal mucosa, Sigma-Aldrich) was performed as described previously [59]. The iodination of LPS was performed as described by Ulevitch [60]. 1 mg *Escherichia coli* 0111:B4 LPS was incubated in 50 mM p-OH benzimidate in borate buffer, pH 8, over night at 4° C., and then dialyzed against PBS, pH 7.4. LPS was then radiolabelled with $^{125}$I using the chloramine T method, and unlabelled $^{125}$I was then removed by dialysis.

Heparin and LPS-Binding Assay.

1, 2 and 5 μg of the synthetic peptides in 100 μl PBS pH 7.4 were applied onto nitrocellulose membranes (Hybond-C, Amersham Biosciences) using a slot-blot apparatus. Membranes were blocked for 1 h at room temperature with 2% bovine serum albumin in PBS pH 7.4 and then incubated with radiolabelled LPS (~40 μg·mL$^{-1}$, 0.13×10$^6$ cpm·μg$^{-1}$) or radiolabelled heparin (~10 μg·mL$^{-1}$, 0.4×10$^6$ cpm·μg$^{-1}$) for 1 h at room temperature in PBS, pH 7.4. Unlabeled heparin (6 mg/ml) was added for competition of binding. The membranes were washed 3 times in PBS, pH 7.4. A Bas 2000 radio-imaging system (Fuji Film, Tokyo, Japan) was used to visualize radioactivity.

Cell Culture.

Murine macrophage cell line, RAW 264.7 (kindly provided by Dr. H Björkbacka) were grown in Dulbeccos Modified Eagle Medium (DMEM) (Gibco) supplemented with 10% fetal calf serum (FCS). All experiments were performed under serum free conditions.

Nitric Oxide Induction in RAW Macrophages.

Confluent cells were harvested and transferred to 96-wells plate (3.5×10$^5$/well). After adhesion cells were washed with phenol red-free DMEM (Gibco). *E. Coli* LPS (100 ng/ml), LL-37 (2 or 10 μM) or HRG (2 or 10 μM) was preincubated at 37° C. for 30 minutes and then transferred to the cells. For inhibition of NO induction, 5 μg/ml anti mouse TLR4 antibody, 10 or 100 μM GHH25 or 100 g/ml heparin were used. The cells were stimulated for 24 hours and nitric oxide was determined using the Griess chemical method [61].

TNF-α Release from Human Macrophages.

Human monocyte-derived macrophages (hMDMs) were obtained from peripheral blood mononuclear cells (PBMCs) obtained from the blood of healthy donors using a Lymphoprep (Axis-Shield PoC AS) density gradient. PBMCs were seeded at concentrations of 3×10$^6$ cells/well into 24-well plates and cultured in RPMI1640 medium supplemented with 10% heat-inactivated autologous human plasma, 2 mM L-glutamine, and 50 μl/ml Antibiotic-Antimycotic (Gibco) in a humidified atmosphere of 5% $CO_2$. After 24 h, non-adherent cells were removed and adherent monocytes were differentiated to macrophages for 10 days, with fresh medium changes every second day. The cells were stimulated for 24 hours with 10 ng/ml of LPS with or without HRG (2 μM) and GHH25 (100 μM) under serum-free conditions. After stimulation the supernatant was aspirated and TNF-α was measured using the TNF-α human ELISA kit (Invitrogen).

Animal Experiments.

The original knockout mice 129/B6-HRG$^{tm1wja1}$ were crossed with C57BL/6 mice (Taconic) for 14 generations to obtain uniform genetic background. These HRG-deficient mouse strain was called B6-HRG$^{tm1wja1}$ following ILAR (Institute of Laboratory Animal Resources) rules. Wildtype C57BL/6 control mice and C57BL/6 Hrg−/− mice (8-12 weeks, 27+/−4 g) were bred in the animal facility at Lund University. C57BL/6 Hrg$^{-/-}$, lacks the translation start point of exon 1 of the Hrg gene [54]. Animals were housed under standard conditions of light and temperature and had free access to standard laboratory chow and water. In order to induce sepsis, 18 □g/g *Escherichia coli* 0111:B4 LPS were injected intraperitoneally into C57BL/6 or C57BL/6 Hrg−/− mice, divided into weight and sex matched groups. Survival and status was followed during seven days.

For treatment with GHH25 peptide, 1 mg of the peptide (diluted in 10 mM Tris, pH 7.4) or buffer only was injected intraperitoneal 30 minutes after LPS-challenge and survival and status was then followed.

TFPI and Heparin Cofactor II

Peptides.

The TFPI and HCII-derived peptides were synthesized by Biopeptide Co., San Diego, USA, with the exception of LL-37 (LLGDFFRKSKEKIGKEFKRIVQRIKDFL-RNLVPRTES [SEQ ID NO: 4]), which was obtained from Innovagen AB, Lund, Sweden. The purity (>95%) of these peptides was confirmed by mass spectral analysis (MALDI-ToF Voyager).

Microorganisms.

Bacterial isolates *Escherichia coli* ATCC 25922, *Pseudomonas aeruginosa* ATCC 27853, *Staphylococcus aureus* ATCC 29213, *Bacillus subtilis* ATCC 6633, *Candida albicans* ATCC 90028 and *Candida parapsilosis* ATCC 90018 and were obtained from the Department of Bacteriology, Lund University Hospital.

Viable Count Analysis.

*E. coli* ATCC 25922 bacteria were grown to mid-logarithmic phase in Todd-Hewitt (TH) medium. Bacteria were washed and diluted in 10 mM Tris, pH 7.4 containing 5 mM glucose. *E. coli* ATCC 25922 (50 µA; $2\times10^6$ cfu/ml) were incubated, at 37° C. for 2 h with peptides at the indicated concentrations. Other experiments with the TFPI-peptides and LL-37 were performed in 10 mM Tris, pH 7.4, containing also 0.15 M NaCl, with normal or heat inactivated 20% citrate-plasma (PP). Serial dilutions of the incubation mixture were plated on TH agar, followed by incubation at 37° C. overnight and cfu determination.

Radial Diffusion Assay.

Essentially as described earlier [62, 63], bacteria were grown to mid-logarithmic phase in 10 ml of full-strength (3% w/v) trypticase soy broth (TSB) (Becton-Dickinson). The microorganisms were then washed once with 10 mM Tris, pH 7.4. Subsequently, $4\times10^6$ cfu were added to 15 ml of the underlay agarose gel, consisting of 0.03% (w/v) TSB, 1% (w/v) low electroendosmosis type (EEO) agarose (Sigma-Aldrich) and 0.02% (v/v) Tween 20 (Sigma-Aldrich). The underlay was poured into a Ø 144 mm petri dish. After agarose solidification, 4 mm-diameter wells were punched and 6 µl peptide solution of required concentration added to each well. Plates were incubated at 37° C. for 3 h to allow peptide diffusion. The underlay gel was then covered with 15 ml of molten overlay (6% TSB and 1% Low-EEO agarose in distilled $H_2O$). Antimicrobial activity of a peptide was visualized as a zone of clearing around each well after 18-24 h of incubation at 37° C.

Fluorescence Microscopy.

The impermeant probe FITC (Sigma-Aldrich, St. Louis, USA) was used for monitoring of bacterial membrane permeabilization. *S. aureus* ATCC 29213 bacteria were grown to mid-logarithmic phase in TSB medium. Bacteria were washed and resuspended in buffer (10 mM Tris, pH 7.4, 0.15M NaCl, 5 mM glucose) to yield a suspension of $1\times10^7$ CFU/ml. 100 µl of the bacterial suspension was incubated with 30 µM of the respective peptides at 30° C. for 30 min. Microorganisms were then immobilized on poly (L-lysine)-coated glass slides by incubation for 45 min at 30° C., followed by addition onto the slides of 200 µl of FITC (6 µg/ml) in buffer and a final incubation for 30 min at 30° C. The slides were washed and bacteria fixed by incubation, first on ice for 15 min, then in room temperature for 45 min in 4% paraformaldehyde. The glass slides were subsequently mounted on slides using Prolong Gold antifade reagent mounting medium (Invitrogen, Eugene, USA). Bacteria were visualized using a Nikon Eclipse TE300 (Nikon, Melville, USA) inverted fluorescence microscope equipped with a Hamamatsu C4742-95 cooled CCD camera (Hamamatsu, Bridgewater, USA) and a Plan Apochromat ×100 objective (Olympus, Orangeburg, USA). Differential interference contrast (Nomarski) imaging was used for visualization of the microbes themselves.

Hemolysis Assay.

EDTA-blood was centrifuged at 800 g for 10 min, whereafter plasma and buffy coat were removed. The erythrocytes were washed three times and resuspended in PBS, pH 7.4 to get a 5% suspension. The cells were then incubated with end-over-end rotation for 60 min at 37° C. in the presence of peptides (60 µM). 2% Triton X-100 (Sigma-Aldrich) served as positive control. The samples were then centrifuged at 800 g for 10 min and the supernatant was transferred to a 96 well microtiter plate. The absorbance of hemoglobin release was measured at λ 540 nm and is in the plot expressed as % of TritonX-100 induced hemolysis.

Lactate Dehydrogenase (LDH) Assay.

HaCaT keratinocytes were grown to confluency in 96 well plates (3000 cells/well) in serum-free keratinocyte medium (SFM) supplemented with bovine pituitary extract and recombinant EGF (BPE-rEGF) (Invitrogen, Eugene, USA). The medium was then removed, and 100 µl of the peptides investigated (at 60 µM, diluted in SFM/BPE-rEGF or in keratinocyte-SFM supplemented with 20% human serum) were added. The LDH-based TOX-7 kit (Sigma-Aldrich, St. Louis, USA) was used for quantification of LDH release from the cells. Results represent mean values from triplicate measurements, and are given as fractional LDH release compared to the positive control consisting of 1% Triton X-100 (yielding 100% LDH release).

Slot-Blot Assay.

LPS binding ability of the peptides were examined by slot-blot assay. Peptides (2 and 5 µg) were bound to nitrocellulose membrane (Hybond-C, GE Healthcare BioSciences, UK), pre-soaked in PBS, by vacuum. Membranes were then blocked by 2 wt % BSA in PBS, pH 7.4, for 1 h at RT and subsequently incubated with $^{125}$I-labelled LPS (40 µg/mL; $0.13\times10^6$ cpm/µg) or $^{125}$I-labelled heparin (Sigma) for 1 h at RT in 10 mM Tris, pH 7.4, 0.15 M NaCl, or 10 mM MES, pH 5.5, 0.15 M NaCl. After LPS binding, membranes were washed 3 times, 10 min each time in the above buffers and visualized for radioactivity on Bas 2000 radioimaging system (Fuji, Japan).

Liposome Preparation and Leakage Assay.

The liposomes investigated were anionic (DOPE/DOPG 75/25 mol/mol). DOPG (1,2-Dioleoyl-sn-Glycero-3-Phosphoglycerol, monosodium salt), and DOPE (1,2-dioleoyl-sn-Glycero-3-phoshoetanolamine) were all from Avanti Polar Lipids (Alabaster, USA) and of >99% purity. Due to the long, symmetric and unsaturated acyl chains of these phospholipids, several methodological advantages are reached. In particular, membrane cohesion is good, which facilitates very stable, unilamellar, and largely defect-free liposomes (observed from cryo-TEM) and well defined supported lipid bilayers (observed by ellipsometry and AFM), allowing detailed values on leakage and adsorption density to be obtained. The lipid mixtures were dissolved in chloroform, after which solvent was removed by evaporation under vacuum overnight. Subsequently, 10 mM Tris buffer, pH 7.4, was added together with 0.1 M carboxyfluorescein (CF) (Sigma, St. Louis, USA). After hydration, the lipid mixture was subjected to eight freeze-thaw cycles consisting of freezing in liquid nitrogen and heating to 60° C. Unilamellar liposomes of about Ø140 nm were generated by multiple extrusions through polycarbonate filters (pore size 100 nm) mounted in a LipoFast miniextruder (Avestin, Ottawa, Canada) at 22° C. Untrapped CF was removed by two subsequent gel filtrations (Sephadex G-50, GE Healthcare, Uppsala, Sweden) at 22° C., with Tris buffer as eluent. CF release from the liposomes was determined by monitoring the emitted fluorescence at 520 nm from a liposome dispersion (10 mM lipid in 10 mM Tris, pH 7.4). An absolute leakage scale was obtained by disrupting the liposomes at the end of each experiment through addition of 0.8 mM Triton X-100 (Sigma-Aldrich, St. Louis, USA). A SPEX-fluorolog 1650 0.22-m double spectrometer (SPEX Industries, Edison, USA) was used for the liposome leakage assay in Tris buffer in the absence and presence of liposomes under conditions described above. Measurements were performed in triplicate at 37° C.

CD-Spectroscopy.

The CD spectra of the peptides in solution were measured on a Jasco J-810 Spectropolarimeter (Jasco, U.K.). The measurements were performed at 37° C. in a 10 mm quartz cuvet under stirring and the peptide concentration was 10 μM. The effect on peptide secondary structure of liposomes at a lipid concentration of 100 μM was monitored in the range 200-250 nm. The only peptide conformations observed under the conditions investigated were α-helix and random coil. The fraction of the peptide in α-helical conformation, $X_\alpha$, was calculated from $$X_\alpha (A-A_c)/(A_\alpha - A_c)$$

where A is the recorded CD signal at 225 nm, and $A_\square$ and $A_c$ are the CD signal at 225 nm for a reference peptide in 100% α-helix and 100% random coil conformation, respectively. 100% α-helix and 100% random coil references were obtained from 0.133 mM (monomer concentration) poly-L-lysine in 0.1 M NaOH and 0.1 M.HCl, respectively [64, 65]. For determination of effects of lipopolysaccharide on peptide structure, the peptide secondary structure was monitored at a peptide concentration of 10 μM, both in Tris buffer and in the presence of E. coli lipopolysaccharide (0.02 wt %) (Escherichia coli 0111:B4, highly purified, less than 1% protein/RNA, Sigma, UK). To account for instrumental differences between measurements the background value (detected at 250 nm, where no peptide signal is present) was subtracted. Signals from the bulk solution were also corrected for.

Effects of Various Microbial Products on Macrophages In Vitro and Anti-Inflammatory effects by various peptides of HCII and TFPI.

$3.5 \times 10^5$ cells were seeded in 96-well tissue culture plates (Nunc, 167008) in phenol red-free DMEM (Gibco) supplemented with 10% FBS and antibiotics. Following 6 hours of incubation to permit adherence, cells were stimulated with 10 ng/mL E. coli (0111:84) LPS (Sigma), lipoteichoic acid, peptioglycan, or zymosan, with and without peptides at the indicated doses (see figure legends and figures). The levels of NO in culture supernatants were determined after 24 hours from stimulation using the Griess reaction [66]. Briefly, nitrite, a stable product of NO degradation, was measured by mixing 50 μl of culture supernatants with the same volume of Griess reagent (Sigma, G4410) and reading absorbance at 550 nm after 15 min. Phenol-red free DMEM with FBS and antibiotics were used as a blank. A standard curve was prepared using 0-80 μM sodium nitrite solutions in ddH20.

Clotting Assays.

All clotting times were measured using an Amelung coagulometer. Activated partial thromboplastin time (aPTT) was measured by incubating the peptides diluted in sterile water at the indicated concentrations, with 100 μL citrated human plasma for 1 minute followed by the addition of 100 μL aPTT reagent (aPTT Automate, Diagnostica Stago) for 60 seconds at 37° C. Clotting was initiated by the addition of 100 μL of a 25-mM $CaCl_2$ solution. In the prothombrin time assay (PT), clotting was initiated by the addition of 100 μL Thrombomax with calcium (PT reagent; Sigma-Aldrich). For measuring the thrombin clotting time (TCT), clotting was initiated by the addition of 100 μL Accuclot thrombin time reagent (TCT reagent; Sigma-Aldrich).

Results and Conclusions

In summary, peptides reported above corresponding cryptic heparin binding sites in serpins such as HCII, ATIII and TFPI possess antibacterial, anti-inflammatory and anti-coagulative properties (FIG. 1-8, 19-23). Of particular importance was the finding that the HCII peptides blocked TLR-mediated LPS responses as well as the intrinsic pathway of coagulation. Furthermore, the TFPI peptides showed unique and previously undisclosed inhibitory activities on both the intrinsic, as well as extrinsic pathways of coagulation. The results thus illustrate that the peptides not only attenuate bacterial infection and the related inflammatory response involving interference with macrophage activation, but importantly also interfere with coagulation, and therefore, show significant therapeutic potential for sepsis, COPD and other multifactorial diseases involving pathogenetic steps including inflammation and coagulation.

REFERENCES

1. Lehrer, R. I. and T. Ganz, Cathelicidins: a family of endogenous antimicrobial peptides. Curr Opin Hematol, 2002. 9(1): p. 18-22.
2. Harder, J., R. Glaser, and J. M. Schröder, Review: Human antimicrobial proteins effectors of innate immunity. J Endotoxin Res, 2007. 13(6): p. 317-38.
3. Zasloff, M., Antimicrobial peptides of multicellular organisms. Nature, 2002. 415(6870): p. 389-95.
4. Tossi, A., L. Sandri, and A. Giangaspero, Amphipathic, alpha-helical antimicrobial peptides. Biopolymers, 2000. 55(1): p. 4-30.
5. Yount, N. Y., et al., Advances in antimicrobial peptide immunobiology. Biopolymers, 2006.
6. Zanetti, M., Cathelicidins, multifunctional peptides of the innate immunity. J Leukoc Biol, 2004. 75(1): p. 39-48.
7. Elsbach, P., What is the real role of antimicrobial polypeptides that can mediate several other inflammatory responses? J Clin Invest, 2003. 111(11): p. 1643-5.
8. Ganz, T., Defensins: antimicrobial peptides of innate immunity. Nat Rev Immunol, 2003. 3(9): p. 710-20.
9. Cole, A. M., et al., Cutting edge: IFN-inducible ELR-CXC chemokines display defensin-like antimicrobial activity. J Immunol, 2001. 167(2): p. 623-7.
10. Brogden, K. A., Antimicrobial peptides: pore formers or metabolic inhibitors in bacteria? Nat Rev Microbiol, 2005. 3(3): p. 238-50.
11. Kowalska, K., D. B. Carr, and A. W. Lipkowski, Direct antimicrobial properties of substance P. Life Sci, 2002. 71(7): p. 747-50.
12. Mor, A., M. Amiche, and P. Nicolas, Structure, synthesis, and activity of dermaseptin b, a novel vertebrate defensive peptide from frog skin: relationship with adenoregulin. Biochemistry, 1994. 33(21): p. 6642-50.
13. Malmsten, M., et al., Antimicrobial peptides derived from growth factors. Growth Factors, 2007. 25(1): p. 60-70.
14. Nordahl, E. A., et al., Activation of the complement system generates antibacterial peptides. Proc Natl Acad Sci USA, 2004. 101(48): p. 16879-84.
15. Pasupuleti, M., et al., Preservation of antimicrobial properties of complement peptide C3a, from invertebrates to humans. J Biol Chem, 2007. 282(4): p. 2520-8.
16. Frick, I. M., et al., The contact system—a novel branch of innate immunity generating antibacterial peptides. Embo J, 2006. 25(23): p. 5569-78.
17. Nordahl, E. A., et al., Domain 5 of high molecular weight kininogen is antibacterial. J Biol Chem, 2005. 280(41): p. 34832-9.
18. Rydengard, V., E. Andersson Nordahl, and A. Schmidtchen, Zinc potentiates the antibacterial effects of histidine-rich peptides against Enterococcus faecalis. Febs J, 2006. 273(11): p. 2399-406.

19. Davie, E. W. and J. D. Kulman, *An overview of the structure and function of thrombin*. Semin Thromb Hemost, 2006. 32 Suppl 1: p. 3-15.
20. Bode, W., *The structure of thrombin: a janus-headed proteinase*. Semin Thromb Hemost, 2006. 32 Suppl 1: p. 16-31.
21. Chapman, A. P., *PEGylated antibodies and antibody fragments for improved therapy: a review*. Adv Drug Deliv Rev, 2002. 54(4): p. 531-45.
22. Veronese, F. M. and J. M. Harris, *Introduction and overview of peptide and protein pegylation*. Adv Drug Deliv Rev, 2002. 54(4): p. 453-6.
23. Veronese, F. M. and G. Pasut, *PEGylation, successful approach to drug delivery*. Drug Discov Today, 2005. 10(21): p. 1451-8.
24. Wang, Y. S., et al., *Structural and biological characterization of pegylated recombinant interferon alpha-2b and its therapeutic implications*. Adv Drug Deliv Rev, 2002. 54(4): p. 547-70.
25. Sato, H., *Enzymatic procedure for site-specific pegylation of proteins*. Adv Drug Deliv Rev, 2002. 54(4): p. 487-504.
26. Bowen, S., et al., *Relationship between molecular mass and duration of activity of polyethylene glycol conjugated granulocyte colony-stimulating factor mutein*. Exp Hematol, 1999. 27(3): p. 425-32.
27. Chapman, A. P., et al., *Therapeutic antibody fragments with prolonged in vivo half-lives*. Nat Biotechnol, 1999. 17(8): p. 780-3.
28. Lwaleed, B. A. and P. S. Bass, *Tissue factor pathway inhibitor: structure, biology and involvement in disease*. J Pathol, 2006. 208(3): p. 327-39.
29. Girard, T. J., et al., *Functional significance of the Kunitz-type inhibitory domains of lipoprotein-associated coagulation inhibitor*. Nature, 1989. 338(6215): p. 518-20.
30. Mine, S., et al., *Structural mechanism for heparin-binding of the third Kunitz domain of human tissue factor pathway inhibitor*. Biochemistry, 2002. 41(1): p. 78-85.
31. Crawley, J. T. and D. A. Lane, *The haemostatic role of tissue factor pathway inhibitor*. Arterioscler Thromb Vasc Biol, 2008. 28(2): p. 233-42.
32. Park, C. T., A. A. Creasey, and S. D. Wright, *Tissue factor pathway inhibitor blocks cellular effects of endotoxin by binding to endotoxin and interfering with transfer to CD14*. Blood, 1997. 89(12): p. 4268-74.
33. Hembrough, T. A., et al., *Identification and characterization of a very low density lipoprotein receptor-binding peptide from tissue factor pathway inhibitor that has antitumor and antiangiogenic activity*. Blood, 2004. 103(9): p. 3374-80.
34. Wesselschmidt, R., et al., *Tissue factor pathway inhibitor: the carboxy-terminus is required for optimal inhibition of factor Xa*. Blood, 1992. 79(8): p. 2004-10.
35. Ettelaie, C., et al., *The role of the C-terminal domain in the inhibitory functions of tissue factor pathway inhibitor*. FEBS Lett, 1999. 463(3): p. 341-4.
36. Ohkura, N., et al., *A novel degradation pathway of tissue factor pathway inhibitor: incorporation into fibrin clot and degradation by thrombin*. Blood, 1997. 90(5): p. 1883-92.
37. Li, A. and T. C. Wun, *Proteolysis of tissue factor pathway inhibitor (TFPI) by plasmin: effect on TFPI activity*. Thromb Haemost, 1998. 80(3): p. 423-7.
38. Cunningham, A. C., et al., *Structural and functional characterization of tissue factor pathway inhibitor following degradation by matrix metalloproteinase-8*. Biochem J, 2002. 367(Pt 2): p. 451-8.
39. Lu, Y. C., W. C. Yeh, and P. S. Ohashi, *LPS/TLR4 signal transduction pathway*. Cytokine, 2008. 42(2): p. 145-51.
40. Nakatomi, K., et al., *Neutrophils responded to immobilized lipopolysaccharide in the absence of lipopolysaccharide-binding protein*. J Leukoc Biol, 1998. 64(2): p. 177-84.
41. Wurfel, M. M., et al., *Targeted deletion of the lipopolysaccharide (LPS)-binding protein gene leads to profound suppression of LPS responses ex vivo, whereas in vivo responses remain intact*. J Exp Med, 1997. 186(12): p. 2051-6.
42. Kichler, A., et al., *Histidine-rich amphipathic peptide antibiotics promote efficient delivery of DNA into mammalian cells*. Proc Natl Acad Sci USA, 2003. 100(4): p. 1564-8.
43. Karima, R., et al., *The molecular pathogenesis of endotoxic shock and organ failure*. Mol Med Today, 1999. 5(3): p. 123-32.
44. Wei, X. Q., et al., *Altered immune responses in mice lacking inducible nitric oxide synthase*. Nature, 1995. 375 (6530): p. 408-11.
45. Michie, H. R., et al., *Detection of circulating tumor necrosis factor after endotoxin administration*. N Engl J Med, 1988. 318(23): p. 1481-6.
46. Sauter, C. and C. Wolfensberger, *Interferon in human serum after injection of endotoxin*. Lancet, 1980. 2(8199): p. 852-3.
47. Dinges, M. M. and P. M. Schlievert, *Comparative analysis of lipopolysaccharide-induced tumor necrosis factor alpha activity in serum and lethality in mice and rabbits pretreated with the staphylococcal superantigen toxic shock syndrome toxin 1*. Infect Immun, 2001. 69(11): p. 7169-72.
48. Opal, S. M., *The host response to endotoxin, antilipopolysaccharide strategies, and the management of severe sepsis*. Int J Med Microbiol, 2007. 297(5): p. 365-77.
49. Schwartz, D. and R. C. Blantz, *Nitric oxide, sepsis, and the kidney*. Semin Nephrol, 1999. 19(3): p. 272-6.
50. Kirikae, T., et al., *Protective effects of a human 18-kilodalton cationic antimicrobial protein (CAP18)-derived peptide against murine endotoxemia*. Infect Immun, 1998. 66(5): p. 1861-8.
51. Haupt, H. and N. Heimburger, [*Human serum proteins with high affinity for carboxymethylcellulose. I. Isolation of lysozyme, C1q and 2 hitherto unknown-globulins*]. Hoppe Seylers Z Physiol Chem, 1972. 353(7): p. 1125-32.
52. Heimburger, N., et al., [*Human serum proteins with high affinity to carboxymethylcellulose. II. Physico-chemical and immunological characterization of a histidine-rich 3, 8S-2-glycoportein (CM-protein I)*]. Hoppe Seylers Z Physiol Chem, 1972. 353(7): p. 1133-40.
53. Jones, A. L., M. D. Hulett, and C. R. Parish, *Histidine-rich glycoprotein: A novel adaptor protein in plasma that modulates the immune, vascular and coagulation systems*. Immunol Cell Biol, 2005. 83(2): p. 106-18.
54. Tsuchida-Straeten, N., et al., *Enhanced blood coagulation and fibrinolysis in mice lacking histidine-rich glycoprotein (HRG)*. J Thromb Haemost, 2005. 3(5): p. 865-72.
55. Olsson, A. K., et al., *A fragment of histidine-rich glycoprotein is a potent inhibitor of tumor vascularization*. Cancer Res, 2004. 64(2): p. 599-605.
56. Rydengård, V., et al., *Histidine-rich glycoprotein protects from systemic Candida infection*. PLoS Pathog, 2008. 4(8): p. e1000116.
57. Rydengård, V., et al., *Histidine-rich glycoprotein exerts antibacterial activity*. Febs J, 2007. 274(2): p. 377-89.

58. Bradford, M. M., *A rapid and sensitive method for the quantitation of microgram quantities of protein utilizing the principle of protein-dye binding.* Anal Biochem, 1976. 72: p. 248-54.
59. Cheng, F., et al., *A new method for sequence analysis of glycosaminoglycans from heavily substituted proteoglycans reveals non-random positioning of 4-and 6-O-sulphated N-acetylgalactosamine in aggrecan-derived chondroitin sulphate.* Glycobiology, 1992. 2(6): p. 553-61.
60. Ulevitch, R. J., *The preparation and characterization of a radioiodinated bacterial lipopolysaccharide.* Immunochemistry, 1978. 15(3): p. 157-64.
61. Park, E., et al., *Taurine chloramine inhibits the synthesis of nitric oxide and the release of tumor necrosis factor in activated RAW 264.7 cells.* J Leukoc Biol, 1993. 54(2): p. 119-24.
62. Andersson, E., et al., *Antimicrobial activities of heparin-binding peptides.* Eur Biochem, 2004. 271(6): p. 1219-26.
63. Lehrer, R. I., et al., *Ultrasensitive assays for endogenous antimicrobial polypeptides.* J Immunol Methods, 1991. 137(2): p. 167-73.
64. Greenfield, N. and G. D. Fasman, *Computed circular dichroism spectra for the evaluation of protein conformation.* Biochemistry, 1969. 8(10): p. 4108-16.
65. Sjogren, H. and S. Ulvenlund, *Comparison of the helix-coil transition of a titrating polypeptide in aqueous solutions and at the air-water interface.* Biophys Chem, 2005. 116(1): p. 11-21.
66. Pollock, J. S., et al., *Purification and characterization of particulate endothelium-derived relaxing factor synthase from cultured and native bovine aortic endothelial cells.* Proc Natl Acad Sci USA, 1991. 88(23): p. 10480-4.

Example B

Novel Host Defense Peptides of Heparin Cofactor II have Therapeutic Effects in Endotoxin-Mediated Shock and Invasive *Pseudomonas aeruginosa* Infection Abstract Background:

Heparin cofactor II is a serine proteinase inhibitor that inhibits, e.g., thrombin. However, the absence of thrombophilia in HCII deficiency in humans suggest additional roles for this serpin. Considering the presence of a cationic, heparin binding, and amphipathic region in the D-helix of HCII, a feature characterizing many host defense peptides, we therefore examined whether peptides of this region of HCII may exert host defense functions.

Methodology and Principal Findings:

Heparin binding peptides of HCII efficiently killed the Gram-negative bacteria *Escherichia coli* and *Pseudomonas aeruginosa*, the Gram-positive *Bacillus subtilis* and *Staphylococcus aureus*, as well as the fungus *Candida albicans*. Fluorescence and electron microscopy studies of peptide-treated bacteria, paired with analysis of peptide effects on liposomes, showed that the peptides exerted membrane-breaking effects similar to those seen after treatment with the "classical" human antimicrobial peptide LL-37. Similarly to LL-37, a marked helix induction was detected for the HCII peptides in presence of negatively charged (bacteria-mimicking) liposomes as well as lipopolysaccharide. The peptides abrogated endotoxin effects in vitro and in vivo, and were shown to reduce mortality during invasive *P. aeruginosa* infection, effects shown to depend on modulation and attenuation of inflammation.

Conclusions:

The results demonstrate for the first time novel host defense peptides of HCII showing potential for treatment of endotoxin mediated shock as well as *P. aeruginosa*

Summary

Infectious diseases account for millions of deaths worldwide each year and incur tremendous health care costs. The disease spectrum is broad and includes acute disease, such as erysipelas, sepsis, pneumonia and numerous other infections, having a direct association to a given pathogen, as well as chronic diseases, where microbes often cause a long-standing inflammatory state. The human pathogen *Pseudomonas aeruginosa* cause, and/or aggravate, a spectrum of diseases including bacterial conjunctivitis and keratitis, otitis, postoperative and burn wound infections, chronic leg ulcers, pneumonia, and cystic fibrosis. New bactericidal agents potent against both *P. aeruginosa* are therefore needed, and there is significant interest in the potential use of AMPs as novel treatment modalities (Marr, Gooderham et al. 2006). Considering the increasing resistance problems against conventional antibiotics, antimicrobial peptides have recently emerged as potential therapeutic candidates. AMPs provides a first line of defense against invading microbes in almost all organisms (Tossi, Sandri et al. 2000; Lehrer and Ganz 2002; Zasloff 2002; Yount, Bayer et al. 2006; Harder, Glaser et al. 2007). During recent years it has become increasingly evident that many cationic and amphipathic antimicrobial peptides (AMP), such as defensins and cathelicidins, are multifunctional, also mediating immunomodulatory roles and angiogenesis (Elsbach 2003; Ganz 2003; Zanetti 2004), thus motivating the recent and broader definition host defense peptides (HDP) for these members of the innate immune system. Ideally, AMP should display high bactericidal potency, but low toxicity against (human) eukaryotic cells. Various strategies, such as use of combinational library approaches (Blondelle and Lohner 2000), stereoisomers composed of D-amino acids (Sajjan, Tran et al. 2001) or cyclic D,L-α-peptides (Fernandez-Lopez, Kim et al. 2001), high-throughput based screening assays (Hilpert, Volkmer-Engert et al. 2005; Taboureau, Olsen et al. 2006), quantitative structure-activity relationship (QSAR) approaches (Hilpert, Volkmer-Engert et al. 2005; Marr, Gooderham et al. 2006; Jenssen, Lejon et al. 2007; Pasupuleti, Walse et al. 2008), and identification of endogenous peptides (Papareddy, Rydengard et al.; Nordahl, Rydengard et al. 2004; Nordahl, Rydengard et al. 2005; Malmsten, Davoudi et al. 2006; Malmsten, Davoudi et al. 2007; Pasupuleti, Walse et al. 2007) are currently employed for identifying selective and therapeutically interesting AMPs (Hancock and Sahl 2006; Marr, Gooderham et al. 2006). Despite the potential of these approaches, naturally occurring peptide epitopes may show some advantages in a therapeutic setting considering low immunogenecity as well as inherent additional biological functions, such as immunomodulatory activities.

Heparin cofactor II is a 66.5 kDa, 480 amino acid glycoprotein present in plasma at ~80 ug/ml. However, although HCII blocks free and clot-associated thrombin, its exact physiological role is not fully understood. Similar to antithrombin III, the inhibition of thrombin by HCII is accelerated by glycosaminoglycans, such as heparin (Tollefsen, 1995). While ATIII deficiency is clearly linked to thrombosis, HCII homozygous deficient mice do not suffer from thrombophilia under normal conditions. Plasma concentrations of HCII are significantly decreased during inflammation and infection (REF). Indeed, recent evidence suggest that the primary physiological function of HCII is to inhibit thrombin's non-hemostatic roles such as in the development of atherosclerosis (Rau, Beaulieu et al. 2007). It has also been shown that HCII could function as an extravascular thrombin inhibitor and may play a role in the regulation of wound healing (Hoffman, Loh et al. 2003), and furthermore, chemotactic products have been described upon proteoloysis of HCII (Hoffman, Pratt et al. 1990), further illustrating the potential latent biological activities of this antiproteinase. Structural studies on HCII have revealed that the molecule undergoes an unusual conformational change, termed the Stressed to Relaxed (S to R) transition. Previous work has identified that HCII, when in the R state, exerts potent antimicrobial activities. We here report on the identification of novel host defense peptides derived from the D-helix of HCII, with potent antibacterial and anti-inflammatory activities.

Material and Methods

Peptides

KYE28 and KYE21 peptides ($NH_2$-KYEIT-TIHNLFRKLTHRLFRRNFGYTLR-COOH [SEQ ID NO: 1] and $NH_2$-KYEITTIHNLFRKLTHRLFRR-COOH, [SEQ ID NO: 2] respectively) were synthesized by Biopeptide Co., San Diego, USA, while LL-37 (LLGDFFRK-SKEKIGKEFKRIVQRIKDFLRNLVPRTES [SEQ ID NO: 4]) was obtained from Innovagen AB, Lund, Sweden. The purity (>95%) of these peptides was confirmed by mass spectral analysis (MALDI-ToF Voyager).

Microorganisms

Bacterial isolates *Escherichia coli* ATCC 25922, *Pseudomonas aeruginosa* ATCC 27853, *Staphylococcus aureus* ATCC 29213, *Bacillus subtilis* ATCC 6633, *Candida albicans* ATCC 90028 and *Candida parapsilosis* ATCC 90018 and were obtained from the Department of Bacteriology, Lund University Hospital.

Radial Diffusion Assay

Essentially as described earlier (Lehrer, Rosenman et al. 1991; Andersson, Rydengård et al. 2004), bacteria were grown to mid-logarithmic phase in 10 ml of full-strength (3% w/v) trypticase soy broth. (TSB) (Becton-Dickinson). The microorganisms were then washed once with 10 mM Tris, pH 7.4. Subsequently, $4 \times 10^6$ cfu were added to 15 ml of the underlay agarose gel, consisting of 0.03% (w/v) TSB, 1% (w/v) low electroendosmosis type (EEO) agarose (Sigma-Aldrich) and 0.02% (v/v) Tween 20 (Sigma-Aldrich). The underlay was poured into a Ø 144 mm petri dish. After agarose solidification, 4 mm-diameter wells were punched and 6 µl peptide solution of required concentration added to each well. Plates were incubated at 37° C. for 3 h to allow peptide diffusion. The underlay gel was then covered with 15 ml of molten overlay (6% TSB and 1% Low-EEO agarose in distilled $H_2O$). Antimicrobial activity of a peptide was visualized as a zone of clearing around each well after 18-24 h of incubation at 37° C.

Viable-Count Analysis

*E. coli* ATCC 25922, *P. aeruginosa* 15159, or *S. aureus* ATCC 29213 bacteria were grown to mid-logarithmic phase in Todd-Hewitt (TH) medium (Becton and Dickinson, Maryland, USA). The microorganisms were then washed and diluted in 10 mM Tris, pH 7.4 containing 5 mM glucose. Following this, bacteria (50 µl; $2 \times 10^6$ cfu/ml) were incubated, at 37° C. for 2 hours, with KYE28, KYE21 or LL-37 (at 0.03, 0.06, 0.3, 0.6, 3, 6, 30, 60 µM) in 10 mM Tris, 0.15 M NaCl, with or without 20% human citrate-plasma. To quantify the bactericidal activity, serial dilutions of the incubation mixtures were plated on TH agar, followed by incubation at 37° C. overnight and the number of colony-forming units was determined. 100% survival was defined as total survival of bacteria in the same buffer and under the same condition in the absence of peptide. Significance was determined using the statistical software SigmaStat (SPSS Inc., Chicago, Ill., USA).

Minimal Inhibitory Concentration (MIC) Determination

MIC assay was carried out by a microtiter broth dilution method as previously described in the NCSLA guidelines (Wiegand, I., Hilpert, K. & Hancock, R. E. Agar and broth dilution methods to determine the minimal inhibitory concentration (MIC) of antimicrobial substances. *Nat Protoc* 3, 163-175 (2008)). In brief, fresh overnight colonies were suspended to a turbidity of 0.5 units and further diluted in Mueller-Hinton broth (Becton Dickinson). For determination of MIC, peptides were dissolved in water at concentration 10 times higher than the required range by serial dilutions from a stock solution. Ten µl of each concentration was added to each corresponding well of a 96-well microtiter plate (polypropylene, Costar Corp.) and 90 µl of bacteria ($1 \times 10^5$) in MH medium added. The plate was incubated at 37° C. for 16-18 h. MIC was taken as the lowest concentration where no visual growth of bacteria was detected.

Fluorescence Microscopy

The impermeant probe FITC (Sigma-Aldrich, St. Louis, USA) was used for monitoring of bacterial membrane permeabilization. *S. aureus* ATCC 29213 bacteria were grown to mid-logarithmic phase in TSB medium. Bacteria were washed and resuspended in buffer (10 mM Tris, pH 7.4, 0.15M NaCl, 5 mM glucose) to yield a suspension of $1 \times 10^7$ CFU/ml. 100 µl of the bacterial suspension was incubated with 30 µM of the respective peptides at 30° C. for 30 min. Microorganisms were then immobilized on poly (L-lysine)-coated glass slides by incubation for 45 min at 30° C., followed by addition onto the slides of 200 µl of FITC (6 µg/ml) in buffer and a final incubation for 30 min at 30° C. The slides were washed and bacteria fixed by incubation, first on ice for 15 min, then in room temperature for 45 min in 4% paraformaldehyde. The glass slides were subsequently mounted on slides using Prolong Gold antifade reagent mounting medium (Invitrogen, Eugene, USA). Bacteria were visualized using a Nikon Eclipse TE300 (Nikon, Melville, USA) inverted fluorescence microscope equipped with a Hamamatsu C4742-95 cooled CCD camera (Hamamatsu, Bridgewater, USA) and a Plan Apochromat ×100 objective (Olympus, Orangeburg, USA). Differential interference contrast (Nomarski) imaging was used for visualization of the microbes themselves.

Hemolysis Assay

EDTA-blood was centrifuged at 800 g for 10 min, whereafter plasma and buffy coat were removed. The erythrocytes were washed three times and resuspended in PBS, pH 7.4 to get a 5% suspension. The cells were then incubated with end-over-end rotation for 60 min at 37° C. in the presence of peptides (60 µM). 2% Triton X-100 (Sigma-Aldrich) served as positive control. The samples were then centrifuged at 800 g for 10 min and the supernatant was transferred to a 96 well microtiter plate.

Lactate Dehydrogenase (LDH) Assay

HaCaT keratinocytes were grown to confluency in 96 well plates (3000 cells/well) in serum-free keratinocyte medium (SFM) supplemented with bovine pituitary extract and recombinant EGF (BPE-rEGF) (Invitrogen, Eugene, USA). The medium was then removed, and 100 µl of the peptides investigated (at 60 µM, diluted in SFM/BPE-rEGF or in keratinocyte-SFM supplemented with 20% human serum) were added. The LDH-based TOX-7 kit (Sigma-Aldrich, St. Louis, USA) was used for quantification of LDH release from the cells. Results represent mean values from triplicate measurements, and are given as fractional LDH release compared to the positive control consisting of 1% Triton X-100 (yielding 100% LDH release).

MTT Assay

Sterile filtered MTT (3-(4,5-dimethylthiazolyl)-2,5-diphenyl-tetrazolium bromide; Sigma-Aldrich) solution (5 mg/ml in PBS) was stored protected from light at −20° C. until usage. HaCaT keratinocytes, 3000 cells/well, were seeded in 96 well plates and grown in serum free keratinocyte-SFM/BPE-rEGF medium to confluency. Peptides investigated were then added at 60 μM and 120 μM. After incubation over night, 20 μl of the MTT solution was added to each well and the plates incubated for 1 h in $CO_2$ at 37° C. The MTT containing medium was then removed by aspiration. The blue formazan product generated was dissolved by the addition of 100 μl of 100% DMSO per well. The plates were then gently swirled for 10 min at room temperature to dissolve the precipitate. The absorbance was monitored at 550 nm, and results given represent mean values from triplicate measurements.

LPS Effects on Macrophages In Vitro $3.5 \times 10^5$ cells were seeded in 96-well tissue culture plates (Nunc, 167008) in phenol red-free DMEM (Gibco) supplemented with 10% FBS and antibiotics. Following 6 hours of incubation to permit adherence, cells were stimulated with 10 ng/mL *E. coli* LPS (0111:B4) with and without peptide of various doses. The levels of NO in culture supernatants were determined after 24 hours from stimulation using the Griess reaction (Pollock, Forstermann et al. 1991). Briefly, nitrite, a stable product of NO degradation, was measured by mixing 50 μl of culture supernatants with the same volume of Griess reagent (Sigma, G4410) and reading absorbance at 550 nm after 15 min. Phenol-red free DMEM with FBS and antibiotics were used as a blank. A standard curve was prepared using 0-80 μM sodium nitrite solutions in ddH20.

Liposome Preparation and Leakage Assay

The liposomes investigated were either zwitterionic (DOPC/cholesterol 60/40 mol/mol or DOPC without cholesterol) or anionic (DOPE/DOPG 75/25 mol/mol). DOPG (1,2-Dioleoyl-sn-Glycero-3-Phosphoglycerol, monosodium salt), DOPC (1,2-dioleoyl-sn-Glycero-3-phoshocholine), and DOPE (1,2-dioleoyl-sn-Glycero-3-phoshoetanolamine) were all from Avanti Polar Lipids (Alabaster, USA) and of >99% purity, while cholesterol (>99% purity), was from Sigma-Aldrich (St. Louis, USA). Due to the long, symmetric and unsaturated acyl chains of these phospholipids, several methodological advantages are reached. In particular, membrane cohesion is good, which facilitates very stable, unilamellar, and largely defect-free liposomes (observed from cryo-TEM) and well defined supported lipid bilayers (observed by ellipsometry and AFM), allowing detailed values on leakage and adsorption density to be obtained. The lipid mixtures were dissolved in chloroform, after which solvent was removed by evaporation under vacuum overnight. Subsequently, 10 mM Tris buffer, pH 7.4, was added together with 0.1 M carboxyfluorescein (CF) (Sigma, St. Louis, USA). After hydration, the lipid mixture was subjected to eight freeze-thaw cycles consisting of freezing in liquid nitrogen and heating to 60° C. Unilamellar liposomes of about Ø140 nm were generated by multiple extrusions through polycarbonate filters (pore size 100 nm) mounted in a LipoFast miniextruder (Avestin, Ottawa, Canada) at 22° C. Untrapped CF was removed by two subsequent gel filtrations (Sephadex G-50, GE Healthcare, Uppsala, Sweden) at 22° C., with Tris buffer as eluent. CF release from the liposomes was determined by monitoring the emitted fluorescence at 520 nm from a liposome dispersion (10 mM lipid in 10 mM Tris, pH 7.4). An absolute leakage scale was obtained by disrupting the liposomes at the end of each experiment through addition of 0.8 mM Triton X-100 (Sigma-Aldrich, St. Louis, USA). A SPEX-fluorolog 1650 0.22-m double spectrometer (SPEX Industries, Edison, USA) was used for the liposome leakage assay in Tris buffer in the absence and presence of liposomes under conditions described above. Measurements were performed in triplicate at 37° C.

CD-Spectroscopy

The CD spectra of the peptides in solution were measured on a Jasco J-810 Spectropolarimeter (Jasco, U.K.). The measurements were performed at 37° C. in a 10 mm quartz cuvet under stirring and the peptide concentration was 10 μM. The effect on peptide secondary structure of liposomes at a lipid concentration of 100 μM was monitored in the range 200-250 nm. The only peptide conformations observed under the conditions investigated were α-helix and random coil. The fraction of the peptide in α-helical conformation was calculated from the CD signal at 225 nm. 100% α-helix and 100% random coil references were obtained from 0.133 mM (monomer concentration) poly-L-lysine in 0.1 M NaOH and 0.1 M HCl, respectively. For determination of effects of lipopolysaccharide on peptide structure, the peptide secondary structure was monitored at a peptide concentration of 10 μM, both in Tris buffer and in the presence of *E. coli* lipopolysaccharide (0.02 wt %) (*Escherichia coli* 0111:B4, highly purified, less than 1% protein/RNA, Sigma, UK). To account for instrumental differences between measurements the background value (detected at 250 nm, where no peptide signal is present) was subtracted. Signals from the bulk solution were also corrected for. Measurements were performed in triplicate at 37° C.

Clinical Parameters

Mouse blood (anti-coagulated with EDTA) was taken by cardiac puncture and analysed with the VetScan HM5 System (TRIOLAB). The number of white blood cells, percentages of lymphocytes, neutrophils, monocytes and platelets were determined.

Cytokine Assay

The cytokines IL-6, IL-10, MCP-1, INF-γ, and TNF-α were measured in cell culture supernatants from RAW264.7 cells and plasma from mice injected with LPS or *P. aeruginosa* (with or without peptide treatment) using the Cytometric bead array; Mouse Inflammation Kit (Becton Dickinson AB) according to the manufacturer's instructions. All plasma samples were stored at −20° C. before the analysis.

LPS Model In Vivo

Male C57BL/6 mice (8-10 weeks, 22+/−5 g), were injected intraperitoneally with 18 mg *E. coli* 0111:B4 LPS (Sigma) per kg of body weight. Thirty minutes after LPS injection, 0.5 mg KYE28, KYE21 or buffer alone was injected intraperitoneally into the mice. Survival and status was followed during seven days. For blood collection and histochemistry, mice were sacrificed 20 h after LPS challenge, and lungs were removed and fixed. These experiments were approved by the Laboratory Animal Ethics Committee of Malmö/Lund.

P. Aeruginosa Infection Model

Animals were Housed Under Standard Conditions of Light and Temperature and Had free access to standard laboratory chow and water. *P. aeruginosa* 15159 bacteria were grown to logarithmic phase ($OD_{620}$~0.5), harvested, washed in PBS, diluted in the same buffer to $2 \times 10^8$ cfu/ml, and kept on ice until injection. Hundred microliter of the bacterial suspension was injected intraperitoneally (i.p.) into female bl6 mice. 1 h or 1 and 7 h after the bacterial injection, 0.5 mg KYE28 or buffer alone was injected sc into the mice. In order to study bacterial dissemination to target organs spleen, liver and kidney were harvested, placed on ice, homogenized, and colony-forming units determined. The P-value was determined using the Mann-Whitney U-test. Data from three independent experiments were pooled.

Histochemistry

Organs collected 20 h after LPS injection were immediately fixed in 4% paraformaldehyde before they were embedded in paraffin and sectioned. Sections were stained 10 min with Mayers Hematoxilin (Histolab AB) and 7 min with Eosin (Merck). Sectioning and staining was done at Histocenter, Gothenburg, Sweden.

Scanning Electron Microscopy

For scanning electron microscopy lungs were taken 20 h after LPS injection. Samples were fixed in 2.5% glutaraldehyde in 0.15 M sodium cacodylate buffer, pH 7.4, over night at room temperature. Specimens were washed with cacodylate buffer, and dehydrated with an ascending ethanol series from 50% (v/v) to absolute ethanol. The specimens were then subjected to critical-point drying in carbon dioxide, with absolute ethanol as intermediate solvent, mounted on aluminium holders, sputtered with 30 nm palladium/gold and examined in a JEOL JSM-350 scanning electron microscope.

Results

To elucidate whether KYE28 and KYE21, derived from a heparin binding epitope of HCII (FIG. 24) exert antimicrobial activity, we investigated the effects in radial diffusion assays (RDA) against Gram-negative *Escherichia coli* and *Pseudomonas aeruginosa*, Gram-positive *Bacillus subtilis* and *Staphylococcus aureus*, as well as the fungi *Candida albicans* and *Candida parapsilosis* (FIG. 25A). It is of note that the activities were similar to those observed for the "classical" human cathelicidin LL-37. The antibacterial results above were further substantiated by matrix-free viable count assays. The results from these dose-response experiments utilizing *E. coli, P. aeruginosa* and *S. aureus* confirmed that the two HCII-derived peptides, and particularly the longer form KYE28 display significant antibacterial activity in buffer containing 0.15 M NaCl as well as in presence of human plasma (FIG. 25B). Particularly for KYE28, kinetic studies demonstrated that the bacterial killing, evaluated in the presence of human plasma, occurred within 5-20 min indicating a fast direct action compatible with many antimicrobial peptides (FIG. 25C). Studies employing the impermeant probe FITC showed that KYE21, here used as a model peptide representing the heparin binding helical epitope, permeabilized bacterial membranes of *E. coli* (FIG. 26). It is noteworthy that this epitope displayed a notable increase in helical content upon binding to liposomes (FIG. 27A) and a significant conformational change together with *E. coli* LPS (FIG. 27B). KYE21 also caused CF release (FIG. 27C), thus indicating a direct effect on lipid membranes. Kinetic analysis showed that ~80% of the maximal release occurred within 5-10 minutes, comparable to results obtained with LL-37 (not shown). AMPs that kill bacteria may also exhibit hemolytic and membrane permeabilizing activities against eukaryotic cells. The results showed that particularly KYE28 exerted significant hemolytic activities at higher doses (30-60 µM) (FIG. 28A). However, the peptides exhibited similar permeabilizing activities as KYE21 and LL-37 with respect to HaCaT cells (FIG. 28B), as well as effects on viability (FIG. 28B). In order to explore hemolytic and cell-toxic effects under physiological conditions, of importance for subsequent in vivo studies, the peptides were added to human blood (made 50% in PBS) as well as studied on HaCaT cells in the presence of human serum. Overall, the results showed that the peptides yielded little permeabilizing effects in these conditions (FIGS. 28)C and D. The MIC-levels of KYE28, according to standard NCSLA-protocols, were comparable to those observed for LL-37 and omiganan (Table 1). Since the latter is a highly active and broad-spectrum designed antimicrobial peptide presently in Phase III clinical studies, the data on KYE28 also implied a possible therapeutic role for this peptide. Taken together, these results demonstrate that KYE28 constitute a previously undisclosed antimicrobial structure of HCII, with membrane breaking capability, and exerting significant antimicrobial activities in vitro under physiological conditions.

As mentioned above, recent evidence shows that antimicrobial peptides trigger a range of immunomodulatory responses. The observation of LPS-binding of KYE21 (FIG. 27B), prompted us to investigate possible endotoxin-neutralizing effects KYE28 and KYE21. In a mouse macrophage model, the two peptides significantly inhibited NO-release of macrophages stimulated by either *E. coli* or *P. aeruginosa* LPS (FIG. 29A). KYE28 reduced TNF-α, MCP-1, as well as IL-10 (FIG. 29), and similar findings were observed for KYE21 (not shown).

In a mouse model of LPS-induced shock (FIG. 30A), both KYE28 and KYE21 displayed a dramatic improvement on survival (FIG. 30A). The treated animals also showed full recovery of weight (FIG. 30B). Analyses of platelet counts after 8 and 20 h showed that particularly KYE28 increased platelet levels after 20 h, suggesting a reduced consumption in this particular LPS-model (FIG. 30C). The levels were completely normalized in the survivors (FIG. 30C). Analyses of cytokines 8 and 20 h after LPS injection showed significant reductions of proinflammatory IL-6, IFN-γ, TNF-α, and MCP-1, whereas an increase in IL-10 was observed after 8 h for both peptides (FIG. 30D). It was noted that KYE28 was particularly effective in reducing IL-6, TNF-α, as well as MCP-1 levels. Similar reductions after treatment with KYE28 were seen in a similar chock model using *P. aeruginosa* LPS, suggesting limited strain variability between Gram-negative bacteria in regards to the effects of KYE28. Correspondingly, while histological and SEM analyses of the lungs from LPS-treated animals demonstrated pulmonary leakage of protein and red blood cells (FIG. 31), lungs of KYE28- and KYE21-treated animals, in contrast to those treated with LPS, showed marked reductions of these LPS-induced effects. The results thus demonstrate a marked antiinflammatory effect of particularly KYE28 and KYE21 in this animal model of LPS-shock.

In order to further explore a potential therapeutic effect of the latter peptide in bacterial sepsis, a model employing *P. aeruginosa* was used. Initial studies showed that bacterial levels increased between 4-12 h in the organs analysed (spleen, kidney, and liver). Treatment with the peptide did not significantly reduce bacterial levels, although a tendency bacterial reduction among the peptide treated animals was observed (FIG. 32A). It was notable however, that a concomitant reduction of cytokine levels was observed, particularly after 12 h, and noted for proinflammatory IL-6, IFN-γ, TNF-α, and MCP-1. For IL-10, the increase after 12 h was not significantly modulated by the peptide. (FIG. 32B). Based on these initial results, the effects of one vs. two administrations of GKY25 was evaluated in the *P. aeruginosa* sepsis model. As seen in FIG. 30A, treatment with one dose did not significantly reduce bacterial cfu, however repeated treatment yielded a moderate reduction of cfu numbers in the organs evaluated. Notably, a slight, but significant increase in platelets was observed (FIG. 33B). This was paralleled by a dramatic and highly significant reduction of cytokines in blood (FIG. 33C). Treatment with one dose of KYE28 did not increase survival. However, a two-dose regime as above, resulted in a significant delay of septic symptoms as well as delayed mortality, and eventually also increase in survival (FIG. 33D).

TABLE 1

Minimal inhibitory concentrations (MIC) of KYE28 and KYE21 against various bacterial species and isolates. LL-37 and omiganan were used as positive controls.

| Bacterial strains | | MIC (mM) | | | |
|---|---|---|---|---|---|
| | | KYE28 | KYE21 | LL-37 | Omiganan |
| E. coli | ATCC 25922 | 10 | 20 | 20 | 20 |
| | Clinical isolate 37.4 | 5 | 40 | 5 | 20 |
| | Clinical isolate 47.1 | 2.5 | 40 | 5 | 20 |
| | Clinical isolate 49.1 | 40 | 160 | 10 | 10 |
| P. aeruginosa | ATCC 27853 | 10 | 10 | 10 | 160 |
| | Clinical isolate 15159 | 20 | 10 | 20 | 20 |
| | Clinical isolate 13.2 | ND | ND | 10 | 40 |
| | Clinical isolate 27.1 | ND | ND | 10 | >160 |
| | Clinical isolate 23.1 | ND | ND | 20 | 40 |
| | Clinical isolate 10.5 | 10 | 10 | 10 | 40 |
| | Clinical isolate 51.1 | 20 | 40 | 40 | 80 |
| | Clinical isolate 62.1 | 10 | 20 | 20 | 20 |
| | Clinical isolate 18488 | 10 | 10 | 20 | 20 |
| S. aureus | ATCC 29213 | 5 | 5 | 40 | 10 |
| | FDA 486 | ND | ND | 10 | 20 |
| | Clinical isolate 1088 | ND | ND | 160 | 20 |
| | Clinical isolate 1090 | ND | ND | 160 | 80 |
| | Clinical isolate 1086 | ND | ND | 20 | 10 |
| | Clinical isolate 16065 | 2.5 | 5 | 10 | 5 |
| | Clinical isolate 13430 | 5 | 5 | 20 | 10 |
| | Clinical isolate 14312 | 5 | 5-10 | 10 | 20 |
| | Clinical isolate 18800 | 5 | 5 | 5 | 2.5 |
| | Clinical isolate 18319 | 5 | 5 | 10 | 20 |
| E. faecalis | Clinical isolate 2374 | ND | ND | >160 | 160 |
| S. pyogenes | AP1 | 10 | 2.5 | 1.2 | 5 |
| S. pneumoniae | TIGR4 | 5 | 5 | 10 | 2.5 |
| | D39 | 5 | 5 | | 5 |
| | Clinical isolate PJ1354 | 20 | 20 | 5 | 10 |
| | Clinical isolate I-104 | 20 | 20 | 20 | 160 |
| | Clinical isolate I-95 | 5 | 40 | 5 | 1.25 |

REFERENCES

Andersson, E., V. Rydengård, et al. (2004). "Antimicrobial activities of heparin-binding peptides." *Eur J Biochem* 271(6): 1219-26.

Blondelle, S. E. and K. Lohner (2000). "Combinatorial libraries: a tool to design antimicrobial and antifungal peptide analogues having lytic specificities for structure-activity relationship studies." *Biopolymers* 55(1): 74-87.

Elsbach, P. (2003). "What is the real role of antimicrobial polypeptides that can mediate several other inflammatory responses?" *J Clin Invest* 111(11): 1643-5.

Fernandez-Lopez, S., H. S. Kim, et al. (2001). "Antibacterial agents based on the cyclic D,L-alpha-peptide architecture." *Nature* 412(6845): 452-5.

Ganz, T. (2003). "Defensins: antimicrobial peptides of innate immunity." *Nat Rev Immunol* 3(9): 710-20.

Hancock, R. E. and H. G. Sahl (2006). "Antimicrobial and host-defense peptides as new anti-infective therapeutic strategies." *Nat Biotechnol* 24(12): 1551-7.

Harder, J., R. Glaser, et al. (2007). "Review: Human antimicrobial proteins effectors of innate immunity." *J Endotoxin Res* 13(6): 317-38.

Hilpert, K., R. Volkmer-Engert, et al. (2005). "High-throughput generation of small antibacterial peptides with improved activity." *Nat Biotechnol* 23(8): 1008-12.

Hoffman, M., K. L. Loh, et al. (2003). "Localization of heparin cofactor II in injured human skin: a potential role in wound healing." *Exp Mol Pathol* 75(2): 109-18.

Hoffman, M., C. W. Pratt, et al. (1990). "Characteristics of the chemotactic activity of heparin cofactor II proteolysis products." *J Leukoc Biol* 48(2): 156-62.

Jenssen, H., T. Lejon, et al. (2007). "Evaluating different descriptors for model design of antimicrobial peptides with enhanced activity toward *P. aeruginosa*." *Chem Biol Drug Des* 70(2): 134-42.

Lehrer, R. I. and T. Ganz (2002). "Cathelicidins: a family of endogenous antimicrobial peptides." *Curr Opin Hematol* 9(1): 18-22.

Lehrer, R. I., M. Rosenman, et al. (1991). "Ultrasensitive assays for endogenous antimicrobial polypeptides." *J Immunol Methods* 137(2): 167-73.

Malmsten, M., M. Davoudi, et al. (2006). "Bacterial killing by heparin-binding peptides from PRELP and thrombospondin." *Matrix Biol* 25(5): 294-300.

Malmsten, M., M. Davoudi, et al. (2007). "Antimicrobial peptides derived from growth factors." *Growth Factors* 25(1): 60-70.

Marr, A. K., W. J. Gooderham, et al. (2006). "Antibacterial peptides for therapeutic use: obstacles and realistic outlook." *Curr Opin Pharmacol*.

Marr, A. K., W. J. Gooderham, et al. (2006). "Antibacterial peptides for therapeutic use: obstacles and realistic outlook." *Curr Opin Pharmacol* 6(5): 468-472.

Nordahl, E. A., V. Rydengard, et al. (2005). "Domain 5 of high molecular weight kininogen is antibacterial." *J Biol Chem* 280(41): 34832-9.

Nordahl, E. A., V. Rydengard, et al. (2004). "Activation of the complement system generates antibacterial peptides." *Proc Natl Acad Sci USA* 101(48): 16879-84.

Papareddy, P., V. Rydengard, et al. "Proteolysis of human thrombin generates novel host defense peptides." *PLoS Pathog* 6(4): e1000857.

Pasupuleti, M., B. Walse, et al. (2007). "Preservation of antimicrobial properties of complement peptide C3a, from invertebrates to humans." *J Biol Chem* 282(4): 2520-8.

Pasupuleti, M., B. Walse, et al. (2008). "Rational design of antimicrobial C3a analogues with enhanced effects against *Staphylococci* using an integrated structure and function-based approach." *Biochemistry* 47(35): 9057-70.

Pollock, J. S., U. Forstermann, et al. (1991). "Purification and characterization of particulate endothelium-derived relaxing factor synthase from cultured and native bovine aortic endothelial cells." *Proc Natl Acad Sci USA* 88(23): 10480-4.

Rau, J. C., L. M. Beaulieu, et al. (2007). "Serpins in thrombosis, hemostasis and fibrinolysis." *J Thromb Haemost* 5 Suppl 1: 102-15.

Sajjan, U. S., L. T. Tran, et al. (2001). "P-113D, an antimicrobial peptide active against *Pseudomonas aeruginosa*, retains activity in the presence of sputum from cystic fibrosis patients." *Antimicrob Agents Chemother* 45(12): 3437-44.

Taboureau, O., O. H. Olsen, et al. (2006). "Design of novispirin antimicrobial peptides by quantitative structure-activity relationship." *Chem Biol Drug Des* 68(1): 48-57.

Tossi, A., L. Sandri, et al. (2000). "Amphipathic, alpha-helical antimicrobial peptides." *Biopolymers* 55(1): 4-30.

Yount, N. Y., A. S. Bayer, et al. (2006). "Advances in antimicrobial peptide immunobiology." *Biopolymers* 84: 435-458.

Zanetti, M. (2004). "Cathelicidins, multifunctional peptides of the innate immunity." *J Leukoc Biol* 75(1): 39-48.

Zasloff, M. (2002). "Antimicrobial peptides of multicellular organisms." *Nature* 415(6870): 389-95.

Example C

NLF20; a Novel Antibiotic Peptide with Therapeutic Potential Against Invasive *Pseudomonas aeruginosa* Infection Summary In order to control microbial flora, humans as well as virtually all life forms are armoured with a rapidly acting antimicrobial system based on short cationic and amphiphilic antimicrobial peptides (AMP). Considering the increasing resistance problems against conventional antibiotics, AMPs have recently emerged as potential therapeutic candidates. Ideally, AMP should display high bactericidal potency, but low toxicity against (human) eukaryotic cells. Various strategies, such as use of combinational library approaches (Blondelle and Lohner 2000), stereoisomers composed of D-amino acids (Sajjan, Tran et al. 2001) or cyclic D,L-α-peptides (Fernandez-Lopez, Kim et al. 2001), high-throughput based screening assays (Hilpert, Volkmer-Engert et al. 2005; Taboureau, Olsen et al. 2006), quantitative structure-activity relationship (QSAR) approaches (Hilpert, Volkmer-Engert et al. 2005; Marr, Gooderham et al. 2006; Jenssen, Lejon et al. 2007; Pasupuleti, Walse et al. 2008), and identification of endogenous peptides (Papareddy, Rydengard et al.; Nordahl, Rydengard et al. 2004; Nordahl, Rydengard et al. 2005; Malmsten, Davoudi et al. 2006; Malmsten, Davoudi et al. 2007; Pasupuleti, Walse et al. 2007) are currently employed for identifying selective and therapeutically interesting AMPs (Hancock and Sahl 2006; Marr, Gooderham et al. 2006). Infectious diseases account for millions of deaths worldwide each year and incur tremendous health care costs. The disease spectrum is broad and includes acute disease, such as erysipelas, sepsis, pneumonia and numerous other infections, having a direct association to a given pathogen, as well as chronic diseases, where microbes often cause a long-standing inflammatory state. The human pathogen *Pseudomonas aeruginosa* cause, and/or aggravate, a spectrum of diseases, including bacterial conjunctivitis and keratitis, otitis, postoperative and burn wound infections, chronic leg ulcers, pneumonia, and cystic fibrosis. New bactericidal agents potent against *P. aeruginosa* are therefore needed, and there is significant current interest in the potential use of AMPs as novel treatment modalities (Marr, Gooderham et al. 2006). However, the use of AMPs in this context is not trivial, e.g., since these bacteria are able to excrete proteolytic enzymes (Schmidtchen, Holst et al. 2003; Werthen, Davoudi et al. 2004), as well as AMP-scavenging exopolysaccharides, as a defense against AMPs.

Serpins are a group of proteins with similar structures that were first identified as a set of proteins able to inhibit proteases. The acronym serpin was originally coined because many serpins inhibit chymotrypsin-like serine proteases (serine protease inhibitors). The first members of the serpin superfamily to be extensively studied were the human plasma proteins antithrombin and antitrypsin, which play key roles in controlling blood coagulation and inflammation, respectively. Structural studies on serpins have revealed that inhibitory members of the family undergo an unusual conformational change, termed the Stressed to Relaxed (S to R) transition. Previous unpublished work has identified that HCII, when in the R state, exerts potent antimicrobial activities. In an effort to investigate these effects further, we here report on the identification of a novel peptide of HCII, NLF20, with potent antibacterial, anti-inflammatory, and anti-coagulation properties.

Material and Methods

Peptides

NLF20 peptide ($NH_2$-NLFRKLTHRLFRRNFGYTLR-COOH [SEQ ID NO: 3]) was synthesized by Biopeptide Co., San Diego, USA, while LL-37 (LLGDFFRK-SKEKIGKEFKRIVQRIKDFLRNLVPRTES [SEQ ID NO: 4]) was obtained from Innovagen AB, Lund, Sweden. The purity (>95%) of these peptides was confirmed by mass spectral analysis (MALDI-ToF Voyager).

Microorganisms

Bacterial isolates *Escherichia coli* ATCC 25922, *Pseudomonas aeruginosa* ATCC 27853, *Staphylococcus aureus* ATCC 29213, *Bacillus subtilis* ATCC 6633, *Candida albicans* ATCC 90028, and *Candida parapsilosis* ATCC 90018 and were obtained from the Department of Bacteriology, Lund University Hospital.

Viable-Count Analysis

*E. coli* ATCC 25922, *P. aeruginosa* 15159, or *S. aureus* ATCC 29213 bacteria were grown to mid-logarithmic phase in Todd-Hewitt (TH) medium (Becton and Dickinson, Maryland, USA). The microorganisms were then washed and diluted in 10 mM Tris, pH 7.4 containing 5 mM glucose. Following this, bacteria (50 µl; $2 \times 10^6$ cfu/ml) were incubated, at 37° C. for 2 hours, with NLF20 or LL-37 (at 0.03, 0.06, 0.3, 0.6, 3, 6, 30, 60 µM) in 10 mM Tris, 0.15 M NaCl, with or without 20% human citrate-plasma. In the experiments using 50% whole blood, *S. aureus* ATCC 29213 and *P. aeruginosa* ATCC 27853 bacteria (50 µl; $2 \times 10^8$ cfu/ml) were incubated at 37° C. for 1 hour in the presence of peptide at 60 (for *P. aeruginosa*) and 120 µM (*P. aeruginosa* and *S. aureus*). To quantify the bactericidal activity, serial dilutions of the incubation mixtures were plated on TH agar, followed by incubation at 37° C. overnight and the number of colony-forming units was determined. 100% survival was defined as total survival of bacteria in the same buffer and under the same condition in the absence of peptide. Significance was determined using the statistical software SigmaStat (SPSS Inc., Chicago, Ill., USA).

Minimal Inhibitory Concentration (MIC) Determination

MIC assay was carried out by a microtiter broth dilution method as previously described in the NCSLA guidelines (Wiegand, I., Hilpert, K. & Hancock, R. E. Agar and broth dilution methods to determine the minimal inhibitory concentration (MIC) of antimicrobial substances. *Nat Protoc* 3, 163-175 (2008)). In brief, fresh overnight colonies were suspended to a turbidity of 0.5 units and further diluted in Mueller-Hinton broth (Becton Dickinson). For determination of MIC, peptides were dissolved in water at concentration 10 times higher than the required range by serial dilutions from a stock solution. Ten µl of each concentration was added to each corresponding well of a 96-well microtiter plate (polypropylene, Costar Corp.) and 90 µl of bacteria ($1 \times 10^5$) in MH medium added. The plate was incubated at 37° C. for 16-18 h. MIC was taken as the lowest concentration where no visual growth of bacteria was detected.

Radial Diffusion Assay

Essentially as described earlier (Lehrer, Rosenman et al. 1991; Andersson, Rydengård et al. 2004), bacteria were grown to mid-logarithmic phase in 10 ml of full-strength (3% w/v) trypticase soy broth (TSB) (Becton-Dickinson). The microorganisms were then washed once with 10 mM Tris, pH 7.4. Subsequently, $4 \times 10^6$ cfu were added to 15 ml of the underlay agarose gel, consisting of 0.03% (w/v) TSB, 1% (w/v) low electroendosmosis type (EEO) agarose (Sigma-Aldrich) and 0.02% (v/v) Tween 20 (Sigma-Aldrich). The underlay was poured into a Ø 144 mm petri dish. After agarose solidification, 4 mm-diameter wells were punched and 6 µl peptide solution of required concentration added to each well. Plates were incubated at 37° C. for 3 h to allow peptide diffusion. The underlay gel was then covered with 15 ml of molten overlay (6% TSB and 1% Low-EEO agarose in distilled $H_2O$). Antimicrobial activity of a peptide was visualized as a zone of clearing around each well after 18-24 h of incubation at 37° C.

Fluorescence Microscopy

The impermeant probe FITC (Sigma-Aldrich, St. Louis, USA) was used for monitoring of bacterial membrane permeabilization. S. aureus ATCC 29213 bacteria were grown to mid-logarithmic phase in TSB medium. Bacteria were washed and resuspended in buffer (10 mM Tris, pH 7.4, 0.15M NaCl, 5 mM glucose) to yield a suspension of $1 \times 10^7$ CFU/ml. 100 µl of the bacterial suspension was incubated with 30 µM of the respective peptides at 30° C. for 30 min. Microorganisms were then immobilized on poly (L-lysine)-coated glass slides by incubation for 45 min at 30° C., followed by addition onto the slides of 200 µl of FITC (6 µg/ml) in buffer and a final incubation for 30 min at 30° C. The slides were washed and bacteria fixed by incubation, first on ice for 15 min, then in room temperature for 45 min in 4% paraformaldehyde. The glass slides were subsequently mounted on slides using Prolong Gold antifade reagent mounting medium (Invitrogen, Eugene, USA). Bacteria were visualized using a Nikon Eclipse TE300 (Nikon, Melville, USA) inverted fluorescence microscope equipped with a Hamamatsu C4742-95 cooled CCD camera (Hamamatsu, Bridgewater, USA) and a Plan Apochromat ×100 objective (Olympus, Orangeburg, USA). Differential interference contrast (Nomarski) imaging was used for visualization of the microbes themselves.

Hemolysis Assay

EDTA-blood was centrifuged at 800 g for 10 min, whereafter plasma and buffy coat were removed. The erythrocytes were washed three times and resuspended in PBS, pH 7.4 to get a 5% suspension. The cells were then incubated with end-over-end rotation for 60 min at 37° C. in the presence of peptides (60 µM). 2% Triton X-100 (Sigma-Aldrich) served as positive control. Following this, the samples were centrifuged at 800 g for 10 min and the supernatant was transferred to a 96 well microtiter plate. In the experiments with blood infected by bacteria, citrate-blood was diluted (1:1) with PBS. The cells were then incubated with end-over-end rotation for 1 h at 37° C. in the presence of peptides (60 and 120 µM) and S. aureus ($2 \times 10^8$ cfu/ml) or P. aeruginosa ($2 \times 10^8$ cfu/ml) bacteria. The absorbance of hemoglobin release was measured at λ 540 nm and is in the plot expressed as % of TritonX-100 induced hemolysis.

Lactate Dehydrogenase (LDH) Assay

HaCaT keratinocytes were grown to confluency in 96 well plates (3000 cells/well) in serum-free keratinocyte medium (SFM) supplemented with bovine pituitary extract and recombinant EGF (BPE-rEGF) (Invitrogen, Eugene, USA). The medium was then removed, and 100 µl of the peptides investigated (at 60 µM, diluted in SFM/BPE-rEGF or in keratinocyte-SFM supplemented with 20% human serum) were added. The LDH-based TOX-7 kit (Sigma-Aldrich, St. Louis, USA) was used for quantification of LDH release from the cells. Results represent mean values from triplicate measurements, and are given as fractional LDH release compared to the positive control consisting of 1% Triton X-100 (yielding 100% LDH release).

MTT Assay

Sterile filtered MTT (3-(4,5-dimethylthiazolyl)-2,5-diphenyl-tetrazolium bromide; Sigma-Aldrich) solution (5 mg/ml in PBS) was stored protected from light at −20° C. until usage. HaCaT keratinocytes, 3000 cells/well, were seeded in 96 well plates and grown in serum free keratinocyte-SFM/BPE-rEGF medium to confluency. Peptides investigated were then added at 60 µM and 120 µM. After incubation over night, 20 µl of the MTT solution was added to each well and the plates incubated for 1 h in $CO_2$ at 37° C. The MTT containing medium was then removed by aspiration. The blue formazan product generated was dissolved by the addition of 100 µl of 100% DMSO per well. The plates were then gently swirled for 10 min at room temperature to dissolve the precipitate. The absorbance was monitored at 550 nm, and results given represent mean values from triplicate measurements.

LPS Effects on Macrophages In Vitro $3.5 \times 10^5$ cells were seeded in 96-well tissue culture plates (Nunc, 167008) in phenol red-free DMEM (Gibco) supplemented with 10% FBS and antibiotics. Following 6 hours of incubation to permit adherence, cells were stimulated with 10 ng/mL E. coli LPS (0111:B4) with and without peptide of various doses. The levels of NO in culture supernatants were determined after 24 hours from stimulation using the Griess reaction (Pollock, Forstermann et al. 1991). Briefly, nitrite, a stable product of NO degradation, was measured by mixing 50 µl of culture supernatants with the same volume of Griess reagent (Sigma, G4410) and reading absorbance at 550 nm after 15 min. Phenol-red free DMEM with FBS and antibiotics were used as a blank. A standard curve was prepared using 0-80 µM sodium nitrite solutions in ddH20.

Liposome Preparation and Leakage Assay

Anionic DOPE/DOPG (75/25 mol/mol) liposomes were investigated regarding peptide-induced membrane disruption. DOPG (1,2-dioleoyl-sn-Glycero-3-phosphoglycerol, monosodium salt), and DOPE (1,2-dioleoyl-sn-Glycero-3-phoshoetanolamine) were from Avanti Polar Lipids (Alabaster, USA) and of >99% purity, while cholesterol (of >99% purity), was from Sigma-Aldrich (St. Louis, USA). The lipid mixtures were dissolved in chloroform, after which solvent was removed by evaporation under vacuum overnight. Subsequently, 10 mM Tris buffer, pH 7.4, was added together with 0.1 M carboxyfluorescein (CF) (Sigma, St. Louis, USA). After hydration, the lipid mixture was subjected to eight freeze-thaw cycles, consisting of freezing in liquid nitrogen and heating to 60° C. Unilamellar liposomes of about Ø140 nm were generated by multiple extrusions through polycarbonate filters (pore size 100 nm) mounted in a LipoFast miniextruder (Avestin, Ottawa, Canada) at 22° C. Untrapped CF was removed by two subsequent gel filtrations (Sephadex G-50, GE Healthcare, Uppsala, Sweden) at 22° C., with Tris buffer as eluent. CF release from the liposomes was determined by monitoring the emitted fluorescence at 520 nm from a liposome dispersion (10 mM lipid in 10 mM Tris, pH 7.4). An absolute leakage scale was obtained by disrupting the liposomes at the end of each experiment through addition of 0.8 mM Triton X-100 (Sigma-Aldrich, St. Louis, USA). A SPEX-fluorolog 1650 0.22-m double spectrometer (SPEX Industries, Edison, USA) was used for the liposome leakage assay. Measurements were performed in triplicate at 37° C.

CD-Spectroscopy

The CD spectra of the peptides in solution were measured on a Jasco J-810 Spectropolarimeter (Jasco, U.K.). The measurements were performed at 37° C. in a 10 mm quartz cuvet under stirring and the peptide concentration was 10 μM. The effect on peptide secondary structure of liposomes at a lipid concentration of 100 μM was monitored in the range 200-250 nm. The only peptide conformations observed under the conditions investigated were α-helix and random coil. The fraction of the peptide in α-helical conformation was calculated from the CD signal at 225 nm. 100% α-helix and 100% random coil references were obtained from 0.133 mM (monomer concentration) poly-L-lysine in 0.1 M NaOH and 0.1 M HCl, respectively. For determination of effects of lipopolysaccharide on peptide structure, the peptide secondary structure was monitored at a peptide concentration of 10 μM, both in Tris buffer and in the presence of *E. coli* lipopolysaccharide (0.02 wt %) (*Escherichia coli* 0111:B4, highly purified, less than 1% protein/RNA, Sigma, UK). To account for instrumental differences between measurements the background value (detected at 250 nm, where no peptide signal is present) was subtracted. Signals from the bulk solution were also corrected for. Measurements were performed in triplicate at 37° C.

Clinical Parameters

Mouse blood (anti-coagulated with EDTA) was taken by cardiac puncture and analysed with the VetScan HM5 System (TRIOLAB). The number of white blood cells, percentages of lymphocytes, neutrophils, monocytes and platelets were determined.

Cytokine Assay

The cytokines IL-6, IL-10, MCP-1, INF-γ, and TNF-α were measured in cell culture supernatants from RAW264.7 cells and plasma from mice injected with LPS or *P. aeruginosa* (with or without peptide treatment) using the Cytometric bead array; Mouse Inflammation Kit (Becton Dickinson AB) according to the manufacturer's instructions. All plasma samples were stored at −20° C. before the analysis.

Clotting Assays

All clotting times were analyzed using a coagulometer (Amelung, Lemgo, Germany). The prothrombin time (PT) and the Thrombin clotting time (TCT) were measured as followed: Hundred microliter of fresh human citrate plasma together with indicated concentrations of NLF20 were pre-warmed for 60 sec at 37° C. before clot formation was initiated by adding 100 μl a clotting reagent. (PT-thromboplastin reagent (Trinity Biotech), TCT: Thrombin reagent (Technoclone)). To record the activated partial thromboplastin time (aPTT), 100 μl of a kaolin-containing solution (Technoclone) was add to the plasma-peptide mix and incubated for 200 sec before clot formation was initiated by adding 100 μl of 30 mM fresh CaCl$_2$ solution.

LPS Model In Vivo

Male C57BL/6 mice (8-10 weeks, 22+/−5 g), were injected intraperitoneally with 18 mg *E. coli* 0111:B4 LPS (Sigma) per kg of body weight. Thirty minutes after LPS injection, 0.5 mg NLF20 or buffer alone was injected intraperitoneally into the mice. Survival and status was followed during seven days. For blood collection and histochemistry, mice were sacrificed 20 h after LPS challenge, and lungs were removed and fixed. These experiments were approved by the Laboratory Animal Ethics Committee of Malmö/Lund.

*P. Aeruginosa* Infection Model

Animals were housed under standard conditions of light and temperature AND had free access to standard laboratory chow and water. *P. aeruginosa* 15159 bacteria were grown to logarithmic phase (OD$_{620}$~0.5), harvested, washed in PBS, diluted in the same buffer to 2×10$^8$ cfu/ml, and kept on ice until injection. Hundred microliter of the bacterial suspension was injected intraperitoneally (i.p.) into female bl6 mice. Immediately subsequent the bacterial injection, 0.5 mg NLF20 (in 10 mM Tris, pH 7.4) or buffer alone was injected i.p. into the mice. In order to study bacterial dissemination to target organs spleen, liver and kidney were harvested, placed on ice, homogenized, and colony-forming units determined. The P-value was determined using the Mann-Whitney U-test. Data from three independent experiments were pooled.

Histochemistry

Organs collected 20 h after LPS injection were immediately fixed in 4% paraformaldehyde before they were embedded in paraffin and sectioned. Sections were stained 10 min with Mayers Hematoxilin (Histolab AB) and 7 min with Eosin (Merck). Sectioning and staining was done at Histocenter, Gothenburg, Sweden.

Scanning Electron Microscopy

For scanning electron microscopy lungs were taken 20 h after LPS injection. Samples were fixed in 2.5% glutaraldehyde in 0.15 M sodium cacodylate buffer, pH 7.4, over night at room temperature. Specimens were washed with cacodylate buffer, and dehydrated with an ascending ethanol series from 50% (v/v) to absolute ethanol. The specimens were then subjected to critical-point drying in carbon dioxide, with absolute ethanol as intermediate solvent, mounted on aluminium holders, sputtered with 30 nm palladium/gold and examined in a JEOL JSM-350 scanning electron microscope.

Results

To elucidate whether NLF20 exerts antimicrobial activity, we investigated the effects in radial diffusion assays (RDA) against Gram-negative *Escherichia coli* and *Pseudomonas aeruginosa*, Gram-positive *Bacillus subtilis* and *Staphylococcus aureus*, as well as the fungi *Candida albicans* and *Candida parapsilosis* (FIG. 34A). As can be seen, NLF20 activities well exceeded those observed for the "classical" human cathelicidin LL-37. The antibacterial results above were further substantiated by matrix-free viable count assays. The results from these dose-response experiments utilizing *E. coli*, *P. aeruginosa* and *S. aureus* confirmed that NLF20 displays significant antibacterial activity. Notably, the activity was retained, and for *E. coli* and *S. aureus*, even enhanced in presence of human citrated plasma (FIG. 34B). In addition, kinetic studies demonstrated that the bacterial killing NLF20 occurred within 5-20 min indicating a fast direct action compatible with many antimicrobial peptides (FIG. 34C). Studies employing the impermeant probe FITC showed that NLF20 permeabilized bacterial membranes of *E. coli* similarly to those seen after treatment with LL-37 (FIG. 35, upper panel). Electron microscopy utilizing *P. aeruginosa* demonstrated extensive membrane damage, with cell envelopes of *P. aeruginosa* devoid of their cytoplasmic contents, and intracellular material found extracellularly (FIG. 35, lower panel). Again, similar findings were obtained with LL-37. These data indicate that NLF20 acts on bacterial membranes. While NLF20 displayed a relatively minor increase in helical content upon binding to liposomes (FIG. 36A), a significant conformational change was observed in the presence of *E. coli* LPS (FIG. 36B). NLF20 also caused CF release (FIG. 36C), thus indicating a direct effect on lipid membranes. Kinetic analysis showed that ~80% of the maximal release occurred within 5-10 minutes, comparable to results obtained with LL-37 (not shown).

AMPs that kill bacteria may also exhibit hemolytic and membrane permeabilizing activities against eukaryotic cells. The results showed that NLF20 exerted hemolytic activities at higher doses (30-60 μM) (FIG. 37A). However, the hemolytic activity was lower than that observed for endogenous LL-37. Likewise, similar findings were observed with respect to permeabilization of HaCaT cells (FIG. 37B), as well as effects on viability as monitored by MTT assay (FIG. 37C). In order to simultaneously explore hemolytic as well as antimicrobial effects under physiological conditions, of importance for subsequent in vivo studies, NLF20 was added to human blood infected by various Gram-positive and Gram-negative pathogens, as well as fungi. It was observed that NLF20, displayed a significant selectivity, demonstrating almost complete eradication of *P. aeruginosa*, *E. coli*, as well as *S. pyogenes*, with little (~2% or less) accompanying hemolysis, at a peptide dose of 120 μM (FIG. 38). For LL-37, the corresponding number was ~8% (Malmsten et al., in manuscript). Striking in this context was the low hemolysis of NLF20 under these conditions, indicating a very pronounced selectivity of the peptide for bacteria. Of note is also that NLF20 was not active against the Gram-positive *S. aureus*, as well as the fungus *C. albicans*. MIC analyses according to NCSLA against these above, as well as other pathogens are presented in Table 2. Overall, NLF20 showed comparable activities to those observed for omiganan, a designer peptide now in late clinical studies.

In order to explore whether NLF20 could be effective against invasive *P. aeruginosa* infection in vivo, we injected this peptide into mice infected with *P. aeruginosa*. Compared to the controls, treatment with NLF yielded significantly lower bacterial numbers in the spleen, liver, and kidney of the animals infected with both and high dose of bacteria (FIG. 39A). Importantly, the antimicrobial effects, as evidenced by reductions in cfu, were present also after treatment was delayed and given subcutaneously 1 h after infection. It is also notable that treatment with only one dose of NLF20, either given sc or ip, was sufficient to prolong survival and significantly reduce mortality, respectively (FIG. 39C). In relation to this, concomitant changes in TNF-α, where a reduction was noted after ip treatment, and IL-10, showing an increase (both administrations), were observed (FIG. 39D). In parallel, thrombocytes were increased (FIG. 39E).

In order to further delineate possible mechanisms underlying the protective effect of NLF20, and considering the above presented LPS-binding property of NLF20, we investigated whether this peptide could exert anti-endotoxin effects in vitro and in vivo. The anti-inflammatory effect of NLF20 was first studied in a macrophage model. As seen in FIG. 40A, NLF20 eliminated LPS-induced NO-responses at 20-40 μM. Next, effects of NLF20 on coagulation were investigated. From measurements of the activated partial thromboplastin time (aPTT) NLF20 impaired the intrinsic pathway of coagulation in normal human plasma. Other parts of the coagulation system, as judged by the prothrombin time (PT; monitoring the extrinsic pathway of coagulation), and the thrombin clotting time (TCT; measuring thrombin induced fibrin network formation), were not significantly affected (FIG. 40B). In a mouse model of LPS-induced shock (FIG. 40C), NLF20 displayed a dramatic improvement on survival (FIG. 40C). The treated animals also showed full recovery of weight (FIG. 40E). Analyses of platelet counts after 8 and 20 h showed that the peptide significantly increased platelets, indicative of reduced consumption in this particular LPS-model (FIG. 40D). The levels were completely normalized in the survivors. Analyses of cytokines 8 and 20 h after LPS injection showed significant reductions of proinflammatory IFN-γ, whereas an increase in IL-10 was observed after 8 h and 20 h. (FIG. 40F). Correspondingly, while histochemical and SEM analyses of the lungs from LPS-treated animals demonstrated pulmonary leakage of protein and red blood cells (FIG. 40G), lungs of NLF20-treated showed marked reductions of these LPS-induced effects. The results thus demonstrate a marked anti-inflammatory effect of NLF20 in this animal model of LPS-shock.

TABLE 2

MIC values

| Bacterial strains | | MIC (mM) | | |
| --- | --- | --- | --- | --- |
| | | NLF20 | LL-37 | Omiganan |
| *E. coli* | ATCC 25922 | 10 | 20 | 20 |
| | Clinical isolate 37.4 | 20 | 5 | 20 |
| | Clinical isolate 47.1 | 40 | 5 | 20 |
| | Clinical isolate 49.1 | 40 | 10 | 10 |
| *P. aeruginosa* | ATCC 27853 | 10-20 | 10 | 160 |
| | Clinical isolate 15159 | 5 | 20 | 20 |
| | Clinical isolate 13.2 | ND | 10 | 40 |
| | Clinical isolate 27.1 | ND | 10 | >160 |
| | Clinical isolate 23.1 | ND | 20 | 40 |
| | Clinical isolate 10.5 | 20 | 10 | 40 |
| | Clinical isolate 51.1 | 20 | 40 | 80 |
| | Clinical isolate 62.1 | 10 | 20 | 20 |
| | Clinical isolate 18488 | 2.5 | 20 | 20 |
| *S. aureus* | ATCC 29213 | 10-20 | 40 | 10 |
| | FDA 486 | ND | 10 | 20 |
| | Clinical isolate 1088 | ND | 160 | 20 |
| | Clinical isolate 1090 | ND | 160 | 80 |
| | Clinical isolate 1086 | ND | 20 | 10 |
| | Clinical isolate 16065 | 20 | 10 | 5 |
| | Clinical isolate 13430 | 20 | 20 | 10 |
| | Clinical isolate 14312 | 20 | 10 | 20 |
| | Clinical isolate 18800 | 20 | 5 | 2.5 |
| | Clinical isolate 18319 | 10 | 10 | 20 |
| *E. faecalis* | Clinical isolate 2374 | ND | >160 | 160 |
| *S. pyogenes* | AP1 | 2.5 | 1.2 | 5 |
| *S. pneumoniae* | TIGR4 | 5 | 10 | 2.5 |
| | D39 | 160 | | 5 |
| | Clinical isolate PJ1354 | 80 | 5 | 10 |
| | Clinical isolate I-104 | 20 | 20 | 160 |
| | Clinical isolate I-95 | 80 | 5 | 1.25 |

REFERENCES

Andersson, E., V. Rydengård, et al. (2004). "Antimicrobial activities of heparin-binding peptides." *Eur J Biochem* 271 (6): 1219-26.

Blondelle, S. E. and K. Lohner (2000). "Combinatorial libraries: a tool to design antimicrobial and antifungal peptide analogues having lytic specificities for structure-activity relationship studies." *Biopolymers* 55(1): 74-87.

Fernandez-Lopez, S., H. S. Kim, et al. (2001). "Antibacterial agents based on the cyclic D,L-alpha-peptide architecture." *Nature* 412(6845): 452-5.

Hancock, R. E. and H. G. Sahl (2006). "Antimicrobial and host-defense peptides as new anti-infective therapeutic strategies." *Nat Biotechnol* 24(12): 1551-7.

Hilpert, K., R. Volkmer-Engert, et al. (2005). "High-throughput generation of small antibacterial peptides with improved activity." *Nat Biotechnol* 23(8): 1008-12.

Jenssen, H., T. Lejon, et al. (2007). "Evaluating different descriptors for model design of antimicrobial peptides with enhanced activity toward *P. aeruginosa*." *Chem Biol Drug Des* 70(2): 134-42.

Lehrer, R. I., M. Rosenman, et al. (1991). "Ultrasensitive assays for endogenous antimicrobial polypeptides." *J Immunol Methods* 137(2): 167-73.

Malmsten, M., M. Davoudi, et al. (2006). "Bacterial killing by heparin-binding peptides from PRELP and thrombospondin." *Matrix Biol* 25(5): 294-300.

Malmsten, M., M. Davoudi, et al. (2007). "Antimicrobial peptides derived from growth factors." *Growth Factors* 25(1): 60-70.

Marr, A. K., W. J. Gooderham, et al. (2006). "Antibacterial peptides for therapeutic use: obstacles and realistic outlook." *Curr Opin Pharmacol.*

Marr, A. K., W. J. Gooderham, et al. (2006). "Antibacterial peptides for therapeutic use: obstacles and realistic outlook." *Curr Opin Pharmacol* 6(5): 468-472.

Nordahl, E. A., V. Rydengard, et al. (2005). "Domain 5 of high molecular weight kininogen is antibacterial." *J Biol Chem* 280(41): 34832-9.

Nordahl, E. A., V. Rydengard, et al. (2004). "Activation of the complement system generates antibacterial peptides." *Proc Natl Acad Sci USA* 101(48): 16879-84.

Papareddy, P., V. Rydengard, et al. "Proteolysis of human thrombin generates novel host defense peptides." *PLoS Pathog* 6(4): e1000857.

Pasupuleti, M., B. Walse, et al. (2007). "Preservation of antimicrobial properties of complement peptide C3a, from invertebrates to humans." *J Biol Chem* 282(4): 2520-8.

Pasupuleti, M., B. Walse, et al. (2008). "Rational design of antimicrobial C3a analogues with enhanced effects against *Staphylococci* using an integrated structure and function-based approach." *Biochemistry* 47(35): 9057-70.

Pollock, J. S., U. Forstermann, et al. (1991). "Purification and characterization of particulate endothelium-derived relaxing factor synthase from cultured and native bovine aortic endothelial cells." *Proc Natl Acad Sci USA* 88(23): 10480-4.

Sajjan, U. S., L. T. Tran, et al. (2001). "P-113D, an antimicrobial peptide active against *Pseudomonas aeruginosa*, retains activity in the presence of sputum from cystic fibrosis patients." *Antimicrob Agents Chemother* 45(12): 3437-44.

Schmidtchen, A., E. Hoist, et al. (2003). "Elastase-producing *Pseudomonas aeruginosa* degrade plasma proteins and extracellular products of human skin and fibroblasts, and inhibit fibroblast growth." *Microb Pathoq* 34(1): 47-55.

Taboureau, O., O. H. Olsen, et al. (2006). "Design of novispirin antimicrobial peptides by quantitative structure-activity relationship." *Chem Biol Drug Des* 68(1): 48-57.

Werthen, M., M. Davoudi, et al. (2004). "*Pseudomonas aeruginosa-induced* infection and degradation of human wound fluid and skin proteins ex vivo are eradicated by a synthetic cationic polymer." *J Antimicrob Chemother* 54(4): 772-9.

Example D

Material and Methods

Clotting Assays

All clotting times were analyzed using a coagulometer (Amelung, Lemgo, Germany). The prothrombin time (PT) and the Thrombin clotting time (TCT) were measured as followed: Hundred microliter of fresh human citrate plasma together with indicated concentrations of NLF20 were pre-warmed for 60 sec at 37° C. before clot formation was initiated by adding 100 µl a clotting reagent. (PT-thromboplastin reagent (Trinity Biotech), TCT: Thrombin reagent (Technoclone)). To record the activated partial thromboplastin time (aPTT), 100 µl of a kaolin-containing solution (Technoclone) was add to the plasma-peptide mix and incubated for 200 sec before clot formation was initiated by adding 100 µl of 30 mM fresh $CaCl_2$ solution.

Results

KYE28 and NLF20 impair the intrinsic pathway of coagulation in normal human plasma determined by measuring the activated partial thromboplastin time (aPTT). KYE21 shows only minor blocking of the aPTT (FIG. 41). Other parts of the coagulation system, as judged by the prothrombin time (PT) monitoring the extrinsic pathway of coagulation, and the thrombin clotting time (TCT), measuring thrombin induced fibrin network formation, were not significantly affected.

The invention claimed is:

1. A method for treating inflammation and/or excessive coagulation of the blood in a patient, the method comprising administering to the patient a therapeutically effective amount of polypeptide, wherein the polypeptide consists of the amino acid sequence of SEQ ID NO:1 or 2:

```
"KYE28":
                                          [SEQ ID NO: 1]
KYEITTIHNLFRKLTHRLFRRNFGYTLR

"KYE21":
                                          [SEQ ID NO: 2]
KYEITTIHNLFRKLTHRLFRR.
```

2. The method according to claim 1, wherein said inflammation and/or or excessive coagulation of the blood in a patient is associated with a disease, condition or indication selected from the following:
   i) Acute systemic inflammatory disease, with or without an infective component, such as systemic inflammatory response syndrome (SIRS), ARDS, sepsis, severe sepsis, and septic shock. Other generalized or localized invasive infective and inflammatory disease, including erysipelas, meningitis, arthritis, toxic shock syndrome, diverticulitis, appendicitis, pancreatitis, cholecystitis, colitis, cellulitis, burn wound infections, pneumonia, urinary tract infections, postoperative infections, and peritonitis;
   ii) Chronic inflammatory and or infective diseases, including cystic fibrosis, COPD and other pulmonary diseases, gastrointestinal disease including chronic skin and stomach ulcerations, other epithelial inflammatory and or infective disease such as atopic dermatitis, oral ulcerations (aphtous ulcers), genital ulcerations and inflammatory changes, parodontitis, eye inflammations including conjunctivitis and keratitis, external otitis, mediaotitis, genitourinary inflammations;
   iii) Postoperative inflammation. Inflammatory and coagulative disorders including thrombosis, DIC, postoperative coagulation disorders, and coagulative disorders related to contact with foreign material, including extracorporeal circulation, and use of biomaterials. Furthermore, vasculitis related inflammatory disease, as well as allergy, including allergic rhinitis and asthma;
   iv) Excessive contact activation and/or coagulation in relation to, but not limited to, stroke; or
   v) Excessive inflammation in combination with antimicrobial treatment.

3. The method according to claim 1, wherein said inflammation and/or or excessive coagulation of the blood in a patient is associated with acute inflammation, sepsis, acute respiratory distress syndrome (ARDS), chronic obstructive pulmonary disease (COPD), cystic fibrosis, asthma, allergic and other types of rhinitis, cutaneous and systemic vasculitis, thrombosis and disseminated intravascular coagulation (DIC).

4. The method according to claim 1, wherein the polypeptide is administered in combination with one or more additional therapeutic agent.

5. The method according to claim 1, wherein the patient is human.

6. A pharmaceutical composition comprising a polypeptide, wherein the polypeptide consists of the amino acid sequence of SEQ ID NO:1 or 2.

7. The pharmaceutical composition according to claim 6, wherein said composition is suitable for administration via a route selected from the group consisting of topical, ocular, nasal, pulmonar, buccal, parenteral (intravenous, subcutaneous, intrathecal and intramuscular), oral, vaginal and rectal.

8. The pharmaceutical composition according to claim 6, wherein said composition is suitable for administration via an implant.

9. The pharmaceutical composition according to claim 6, wherein the pharmaceutical composition is associated with a device or material to be used in medicine.

10. The pharmaceutical composition according to claim 9, wherein the pharmaceutical composition is coated, painted, sprayed or otherwise applied to a suture, prosthesis, implant, wound dressing, catheter, lens, skin graft, skin substitute, fibrin glue or bandage.

11. The pharmaceutical composition according to claim 9, wherein the device or material comprises of a polymer, metal, metal oxide and/or ceramic.

* * * * *

SEQUENCE LISTING

```
<160> NUMBER OF SEQ ID NOS: 7

<210> SEQ ID NO 1
<211> LENGTH: 28
<212> TYPE: PRT
<213> ORGANISM: Homo sapiens

<400> SEQUENCE: 1

Lys Tyr Glu Ile Thr Thr Ile His Asn Leu Phe Arg Lys Leu Thr His
1               5                   10                  15

Arg Leu Phe Arg Arg Asn Phe Gly Tyr Thr Leu Arg
            20                  25

<210> SEQ ID NO 2
<211> LENGTH: 21
<212> TYPE: PRT
<213> ORGANISM: Homo sapiens

<400> SEQUENCE: 2

Lys Tyr Glu Ile Thr Thr Ile His Asn Leu Phe Arg Lys Leu Thr His
1               5                   10                  15

Arg Leu Phe Arg Arg
            20
```

```
<210> SEQ ID NO 3
<211> LENGTH: 20
<212> TYPE: PRT
<213> ORGANISM: Homo sapiens

<400> SEQUENCE: 3

Asn Leu Phe Arg Lys Leu Thr His Arg Leu Phe Arg Arg Asn Phe Gly
1               5                   10                  15

Tyr Thr Leu Arg
            20

<210> SEQ ID NO 4
<211> LENGTH: 37
<212> TYPE: PRT
<213> ORGANISM: Artificial Sequence
<220> FEATURE:
<223> OTHER INFORMATION: Anti-microbial peptide LL-37

<400> SEQUENCE: 4

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser
        35

<210> SEQ ID NO 5
<211> LENGTH: 27
<212> TYPE: PRT
<213> ORGANISM: Homo sapiens

<400> SEQUENCE: 5

Gly Gly Leu Ile Lys Thr Lys Arg Lys Arg Lys Lys Gln Arg Val Lys
1               5                   10                  15

Ile Ala Tyr Glu Glu Ile Phe Val Lys Asn Met
            20                  25

<210> SEQ ID NO 6
<211> LENGTH: 22
<212> TYPE: PRT
<213> ORGANISM: Homo sapiens

<400> SEQUENCE: 6

Thr Lys Arg Lys Arg Lys Lys Gln Arg Val Lys Ile Ala Tyr Glu Glu
1               5                   10                  15

Ile Phe Val Lys Asn Met
            20

<210> SEQ ID NO 7
<211> LENGTH: 17
<212> TYPE: PRT
<213> ORGANISM: Homo sapiens

<400> SEQUENCE: 7

Leu Ile Lys Thr Lys Arg Lys Arg Lys Lys Gln Arg Val Lys Ile Ala
1               5                   10                  15

Tyr
```